United States Patent
Coleman et al.

(10) Patent No.: US 11,383,058 B2
(45) Date of Patent: Jul. 12, 2022

(54) APPARATUS AND METHOD FOR DELIVERING FLUIDS AND/OR GASES TO THE LUNGS

(71) Applicant: Suspended Animation, Inc., Rancho Santa Margarita, CA (US)

(72) Inventors: Nathan John Coleman, Murrieta, CA (US); Philip P. Morello, Costa Mesa, CA (US)

(73) Assignee: SUSPENDED ANIMATION, INC., Lake Forest, CA (US)

( * ) Notice: Subject to any disclaimer, the term of this patent is extended or adjusted under 35 U.S.C. 154(b) by 1009 days.

(21) Appl. No.: 16/031,668

(22) Filed: Jul. 10, 2018

(65) Prior Publication Data
US 2018/0318543 A1    Nov. 8, 2018

Related U.S. Application Data

(63) Continuation-in-part of application No. 15/498,429, filed on Apr. 26, 2017, now Pat. No. 10,046,126.

(60) Provisional application No. 62/328,526, filed on Apr. 27, 2016.

(51) Int. Cl.
| A61M 16/10 | (2006.01) |
| A61M 16/04 | (2006.01) |
| A61M 16/00 | (2006.01) |
| A61M 16/20 | (2006.01) |
| A61M 16/16 | (2006.01) |

(Continued)

(52) U.S. Cl.
CPC ......... *A61M 16/109* (2014.02); *A61F 5/3776* (2013.01); *A61M 16/0003* (2014.02); *A61M 16/0009* (2014.02); *A61M 16/0054* (2013.01); *A61M 16/0066* (2013.01); *A61M 16/04* (2013.01); *A61M 16/0463* (2013.01); *A61M 16/14* (2013.01); *A61M 16/162* (2013.01); *A61M 16/165* (2014.02); *A61M 16/202* (2014.02); *A61F 7/12* (2013.01); *A61F 2007/0019* (2013.01); *A61F 2007/0069* (2013.01); *A61F 2007/126* (2013.01); *A61M 16/0891* (2014.02); *A61M 16/1045* (2013.01); *A61M 16/22* (2013.01); *A61M 2016/0027* (2013.01); *A61M 2205/3368* (2013.01); *A61M 2205/366* (2013.01);

(Continued)

(58) Field of Classification Search
CPC ............ A61M 16/0054; A61M 16/109; A61M 16/14–147; A61M 16/201; A61M 2205/3606; A61M 2205/366; F28D 1/0472

See application file for complete search history.

(56) References Cited

U.S. PATENT DOCUMENTS

| 4,676,232 A | 6/1987 | Olsson et al. |
| 5,335,650 A * | 8/1994 | Shaffer ............. A61M 16/0054 128/200.24 |

(Continued)

FOREIGN PATENT DOCUMENTS

| CN | 1428177 A | 7/2003 |
| WO | 2012062266 A1 | 5/2012 |

*Primary Examiner* — Valerie L Woodward
(74) *Attorney, Agent, or Firm* — Buchalter

(57) ABSTRACT

An apparatus and method for providing heat exchange in the lungs of the mammal during partial liquid ventilation are provided. The apparatus and method can control delivery and removal of partial liquid ventilation to the lungs of a mammal by responding to pressure change in the lungs to minimize danger of causing barotrauma to the patient.

22 Claims, 30 Drawing Sheets

(51) Int. Cl.
*A61M 16/14* (2006.01)
*A61F 5/37* (2006.01)
*A61M 16/22* (2006.01)
*A61M 16/08* (2006.01)
*A61F 7/12* (2006.01)
*A61F 7/00* (2006.01)

(52) U.S. Cl.
CPC ............... *A61M 2205/3606* (2013.01); *A61M 2205/583* (2013.01); *A61M 2230/20* (2013.01)

(56) References Cited

U.S. PATENT DOCUMENTS

| | | | |
|---|---|---|---|
| 5,437,272 A * | 8/1995 | Fuhrman | A61M 16/0841 128/203.12 |
| 5,540,225 A * | 7/1996 | Schutt | A61K 9/0026 128/207.15 |
| 5,706,830 A * | 1/1998 | Parker | A61M 16/0054 128/203.12 |
| 6,041,777 A * | 3/2000 | Faithfull | A61M 16/0054 128/200.24 |
| 6,694,977 B1 | 2/2004 | Federowicz et al. | |
| 7,726,311 B2 * | 6/2010 | Robert | A61M 16/0054 128/205.19 |
| 10,046,126 B2 * | 8/2018 | Coleman | A61F 5/37 |
| 2003/0131844 A1 * | 7/2003 | Kumar | A61P 9/10 128/200.24 |
| 2005/0039892 A1 * | 2/2005 | Calton | F28D 1/0472 165/122 |
| 2010/0012122 A1 * | 1/2010 | Shaffer | A61M 16/0054 128/204.18 |
| 2012/0226337 A1 * | 9/2012 | Tissier | A61F 7/12 607/105 |
| 2014/0350648 A1 * | 11/2014 | Ericson | A61F 7/10 607/105 |

\* cited by examiner

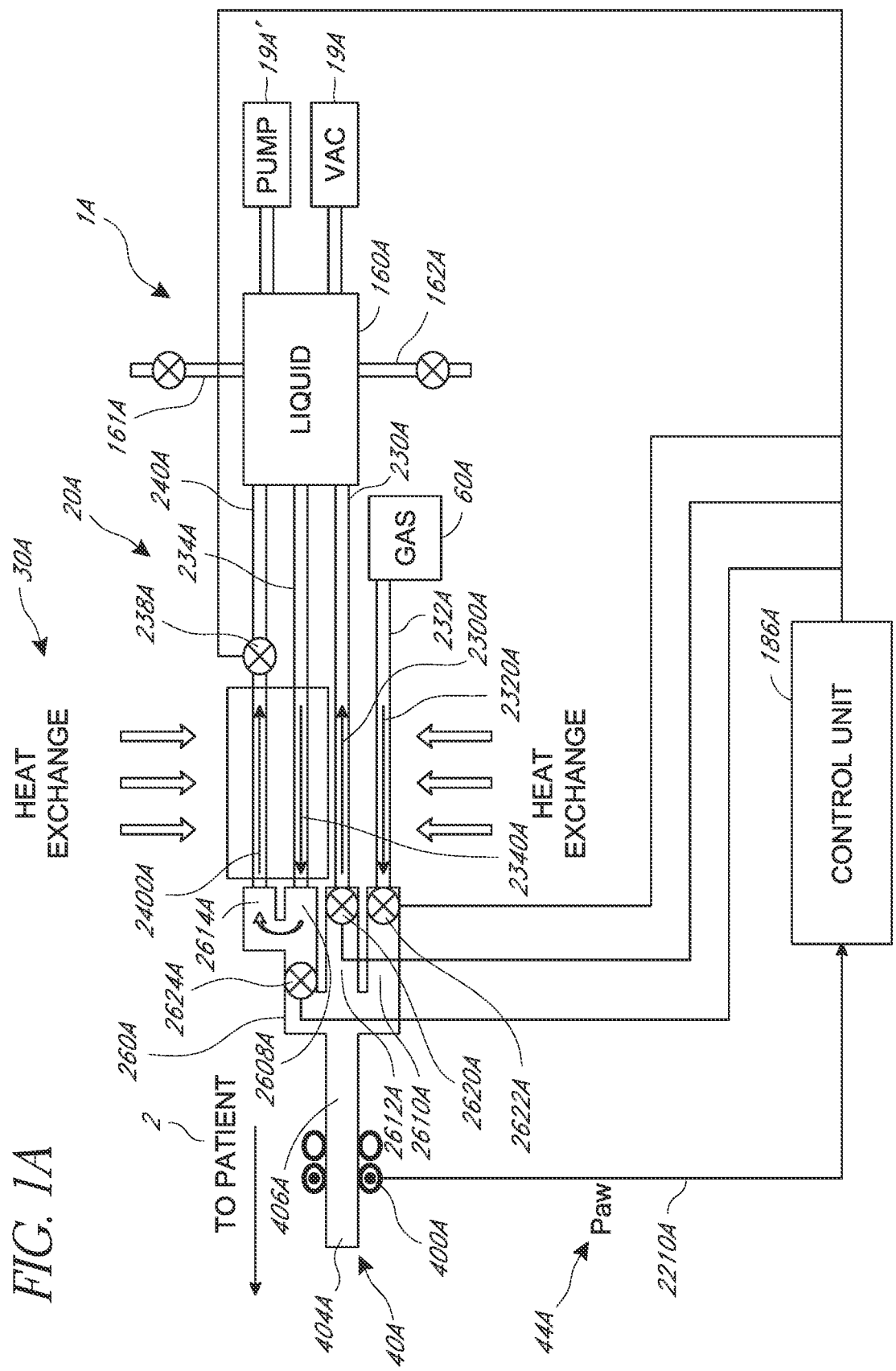

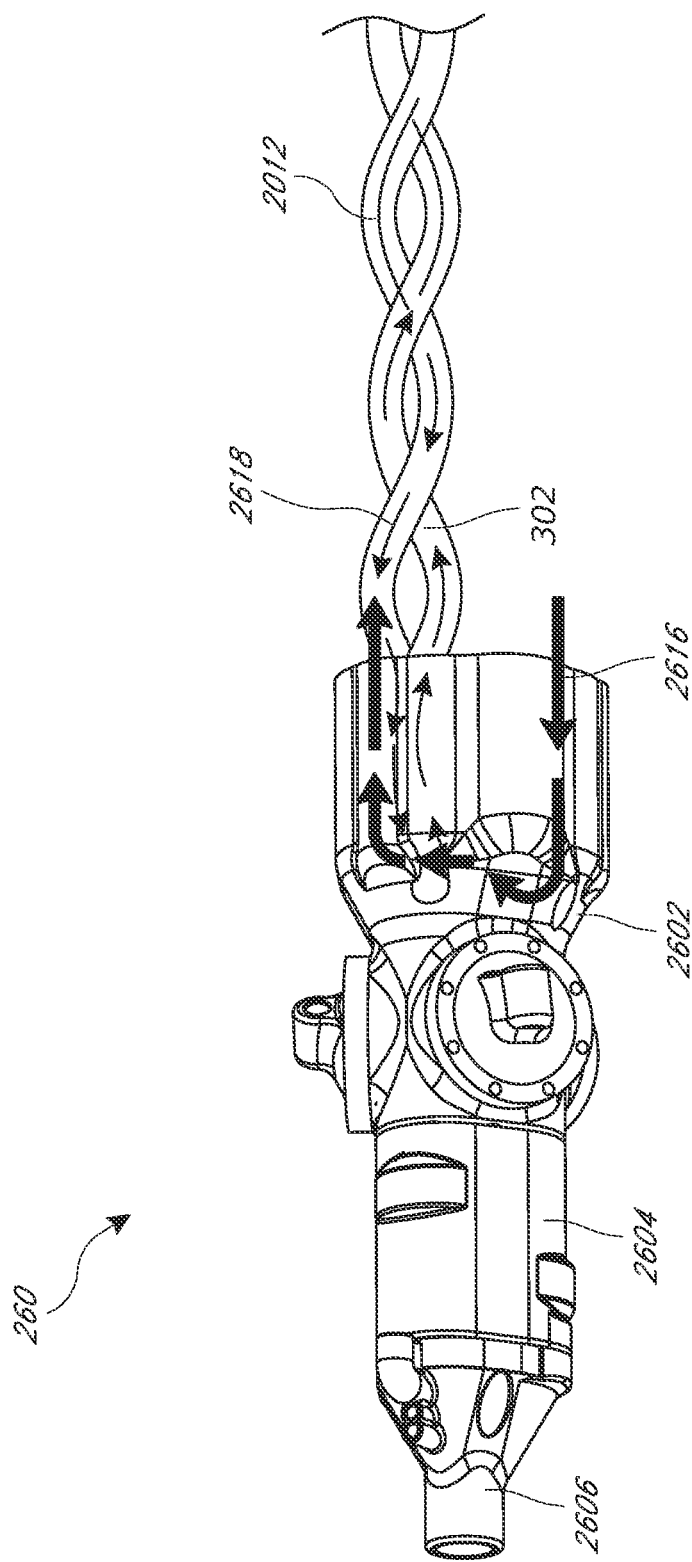

APPARATUS AND METHOD FOR DELIVERING FLUIDS AND/OR GASES TO THE LUNGS

PRIORITY

This application claims priority as a continuation in part to U.S. application Ser. No. 15/498,429, filed Apr. 26, 2017, which claims priority to U.S. Provisional Application No. 62/328,526, filed Apr. 27, 2016, titled "Apparatus and Method for Delivering Fluids and/or Gases to the Lungs," each of which is incorporated by reference in its entirety herein.

BACKGROUND

Ventilators are machines that support breathing by providing air or oxygen into the lungs. Some ventilators may supply an oxygen-rich liquid, such as a perfluorocarbon (PFC), to an air-breathing organism. Partial liquid ventilation ("PLV") can involve infusing the lungs with a liquid, such as a perfluorocarbon (PFC) and/or gases while mechanical ventilation is provided with a standard ventilator.

There are situations in both human and veterinary medicine where it is desirable to rapidly reverse hyperthermia. Specifically, there are clinical situations where it can be important to be able to rapidly reduce dangerously elevated body temperature of the patient to near normal to reverse hyperthermia from heat stroke, drug or surgical anesthetic reaction, and febrile illness secondary to stroke, infection or other illness. Temperature reduction following events such as trauma, stroke, and heart attack can prolong patient viability by a reduction in metabolic rate. There are situations in both human and veterinary medicine where it is desirable to preserve the life of living tissue, organs or the entire mammal body by reduction in temperature and thus metabolic rate. Liquid ventilation can use the lungs as heat exchangers by pumping a chilled liquid and gas mixture into the lungs and, in turn cooling the blood as it flows through the lung tissue. The lungs have a very large surface area and have many blood vessels spread through them, making them very effective for both gas exchange and heat exchange.

SUMMARY

This following disclosure relates to methods and apparatuses for providing heat exchange to the lungs and/or support of life via ventilation. Some embodiments of the disclosure relate to methods and apparatuses of providing heat exchange to the lungs of a mammal during partial liquid ventilation.

U.S. Pat. No. 8,465,535 to Harris, et al discloses a PLV apparatus that can be used for the heat exchange in the lungs of a mammal. However, one aspect of certain embodiments of the disclosure is the recognition that the disclosed device of U.S. Pat. No. 8,465,535 is bulky and heavy, requiring an assembly of pumps for various parts of the flow of the liquid and multiple reservoirs for volume-measured delivery of the liquid. In addition, one aspect of certain embodiments of the disclosure is the recognition that although the liquid in the device disclosed in U.S. Pat. No. 8,465,535 is cooled before leaving the reservoirs, the liquid may warm up again by the ambient air during its travel in the tube assembly before entering an endotracheal tube, leading to less efficient heat exchange.

Another aspect of certain embodiments of the disclosure is the recognition that PLV devices are not adaptive to pressure change in a patient's lungs due to a cardiopulmonary resuscitation (CPR) procedure or to the patient's own breathing which can make them dangerous to use. In other words, Applicant has recognized that prior PLV devices can continue filling the lungs of the patient even when pressure in the patient's airway has reached a threshold level, which can cause physical damage to the airway due to excessively high pressure, and that volumetric extraction may create excessive negative pressure in the thoracic cavity either by accumulation of small fluid accounting error during the procedure, or the common leakage of breathing fluid past the endotracheal tube cuff for which the volumetric ventilator is not equipped to account. Such excessive negative pressure can result in patient harm. Another aspect of certain embodiments of the disclosure is the recognition that volumetric ventilation devices also cannot exploit the "deep breath" cycle that is available in automated CPR and taught to practitioners of manual CPR.

Another aspect of certain embodiments of the disclosure is the recognition that pressure based PLV or LV when used as a heating or cooling device adapts to the individual patient and situation to maximize heat transfer while preventing potential patient harm. Another aspect of certain embodiments of the disclosure is the recognition that pressure based PLV or LV when used in resuscitation can be configured to enhance blood flow from chest compressions by momentarily delaying the extraction phase thereby increasing compression/contraction force on the heart muscle.

One aspect of certain embodiments of the disclosure is to provide a more compact and lighter PLV apparatus that provides more efficient heat exchange to the lungs and/or that can also respond to pressure change due to a CPR procedure or to a patient's own breathing to reduce likelihood of barotrauma to the patient.

In accordance with certain embodiments disclosed herein, an apparatus for providing partial liquid ventilation to lungs of a mammal provides heat exchange in the lungs of the mammal without or reduced danger of causing barotrauma to the patient.

Certain embodiments comprise an apparatus for providing fluid to a lung. The apparatus can include a delivery device configured to deliver liquid and/or gas to the lung; a liquid delivery passage, a gas delivery passage and a suction passage, the liquid delivery, the gas delivery and the suction passages in fluid communication with the delivery device, a fluid reservoir in fluid communication with the liquid delivery passage; a vacuum source in communication with the suction passage; a gas source in communication with the gas delivery passage; and one or more pressure sensors. The apparatus can include one or more valves configured to control flow through the liquid delivery, the gas delivery and/or the suction passages when the apparatus switches between an inhale phase and an exhale phase. A control unit can be operatively connected to the patient's airway pressure sensor(s) or optionally other non-patient airway connected sensors, switches or a manual switch(es) and one or more valves, the control unit configured to, in response to a signal from the pressure sensor(s), to switch the apparatus between an inhale phase in which the liquid from the fluid reservoir is delivered through the liquid delivery passage and to the delivery device to the patient and/or gas can be delivered from the gas source to the gas delivery passage to the delivery device to the patient and an exhale phase in which liquid and/or gas can be withdrawn from the patient through the delivery device into the suction passage.

Certain embodiments can comprise a method for partial liquid ventilation of lungs, comprising detecting a pressure in the lungs; when upon conclusion of the patient's exhalation breath, the airway pressure reaches an initial value, which initiates the delivery of gas into the lungs and subsequent delivery of a liquid to the lungs during an inhale phase; and when the pressure reaches a second value, switching back to the exhale phase and withdrawing liquid and/or gas from the lungs until the pressure reaches the previous initial value or a third value repeating the breathing cycle. In lieu of patient airway pressure sensing, optionally, manual control or other sensor means could be employed to switch between inhale and exhale breathing cycles.

Certain embodiments can comprise a method for partial liquid ventilation of lungs, comprising, in response to detecting a patient's breathing, delivering gas into the lungs and subsequently delivering a liquid to the lungs during an inhale phase; detecting a pressure in the lungs; and when the pressure reaches a first value, switching to an exhale phase and withdrawing liquid and/or gas from the lungs until the pressure reaches a second value.

Certain embodiments can comprise a method for partial liquid ventilation of lungs, comprising in response to an application of pressure to a patient's lungs during a cardiopulmonary resuscitation, delivering gas into the lungs and subsequently delivering a liquid to the lungs during an inhale phase; detecting a pressure in the lungs; and when the pressure reaches a first value, switching to an exhale phase and withdrawing liquid and/or gas from the lungs until the pressure reaches a second value.

Certain embodiments can comprise a method for liquid ventilation of lungs, comprising aerating a liquid with a turbine pump; and delivering the aerated liquid to the lungs.

Certain embodiments can comprise a method for liquid ventilation of lungs, comprising with a turbine pump mixing a first liquid with a second fluid to create an emulsification of the first liquid and second fluid, wherein the second fluid is at a different temperature and/or may have different properties including being a gas than the first liquid; and delivering the emulsification or aerated liquid to the lungs.

Certain embodiments can comprise an apparatus for providing liquid and/or gas to a lung that includes a delivery device configured to deliver liquid and/or gas to the lung; a liquid delivery passage, a gas delivery passage and a suction passage, the liquid delivery, the gas delivery and the suction passages in fluid communication with the delivery device, a fluid reservoir in fluid communication with the liquid delivery passage; a vacuum source in communication with the suction passage; a gas source in communication with the gas delivery passage; and a one or more valves configured to control flow through the liquid delivery, the gas delivery and/or the suction passages when the apparatus switches between an inhale phase and an exhale phase. The apparatus can switch between a gas ventilation mode, and partial liquid ventilation mode and/or a total liquid ventilation mode.

Certain embodiments can comprise an apparatus for providing liquid and/or gas to a lung that includes one or more magnetic or non-mechanical contact switches configured to prevent arcing.

Certain embodiments can include an apparatus for providing liquid and/or gas to a lung that includes a fluid containment and/or filter for containing and/or filtering gas and/or liquid removed from the lung.

Certain embodiments can include a method for ventilating of a lung of a patient that includes applying a band configured to limit stretching of a patient's lungs; and supplying ventilation to the patient.

Certain embodiments may be improved as configured to use a more compact and thermally efficient fluid delivery device which can use a simplified ventilator and be able to use an earlier ventilator without modification. The simplified ventilator would no longer need to accommodate a return loop for the breathable liquid for the purpose of heat exchange other than that returning from the patient. The set of solenoids 1024 may be eliminated or re-purposed to provide pressure/vacuum signal to a pressure switch to interrupt other elements which will no longer need to operate constantly.

Certain embodiments may incorporate and improve additional heat exchangers in the return line to remove heat from the returning warm fluid to increase heat removal rate and/or extend liquid pump (also referred to non-limiting as "turbine" where appropriate, particularly where it is used to assist mixing of gasses with liquids) operation life. The coolant supply may be branched off from the primary supply of coolant to the fluid delivery device or may use the cooling liquid exiting the fluid delivery device.

Certain embodiments may incorporate a secondary or primary cooler within the fluid reservoir or within an additional fluid reservoir, these may be constructed as a disposable, using corrugated tube as the heat transfer surface.

Certain embodiments may incorporate a pressure switch to interrupt or terminate electrical power to the main turbine during the exhale phase as a means to extent turbine use life and reduce power consumption.

Certain embodiments may include an access port in the breathable liquid line to allow filling or topping off of breathable liquid during the inhale phase and/or removal or emptying of breathable fluid during the exhale phase. This may include use of a reversible filling tool which incorporates a one-way or check valve.

Certain embodiments may include a back flow preventer built into the pressure/vacuum inlet port of the reservoir to prevent aspirating breathable liquid into the system.

Certain embodiments may use a temperature enhancing additive to an ice bath such as Calcium Chloride to reduce temperature of any of the heat exchangers described herein for greater heat transfer. Exemplary embodiments may include an ice bath for cooling the turbine to improve its reliability and service life.

Certain embodiments may be improved with a temperature sensor placed distally (relative to the device) to sense temperature of the breathable liquid immediately before entering the patient. This may further be used to modulate liquid temperature to prevent frostbite damage of the patient's trachea. Further, the temperature may be modulated by interrupting or terminating flow of cooling liquid.

Owing to the poor uptake of $CO_2$ by some current breathable liquids, and the reduced cooling when the breathable liquid is replaced by gasses, certain embodiments may include a pulse oximeter or other photoplethysmic and/or gas sensor device to ensure enough gasses are used in the cycle to enhance gas exchange in the lungs while minimizing any slowing of cooling rate to accomplish this.

Some embodiments may include a manually operated setting to control duration of the initial gas and part of the fluid delivery phase, which may override any automated feedback from a sensing device such as a photoplethysmic sensor.

Some embodiments may include a sparging device in the vicinity of the turbine to admit gasses for medication, oxygenation, or removal of other species such as $CO_2$ or toxins more effectively or in addition to the function performed by the breathable liquid.

Some embodiments of the fluid delivery device may be improved for portability, maintainability, reduction of size in close proximity to the patient, and ease of service via use of gas pressure operated two state valves placed into the fluid delivery and fluid extraction lines in concert with one way or check valves placed also in said fluid delivery and extraction lines.

Certain embodiments may include chemically resistant and/or biocompatible coatings applied to polymer or 3D printed components.

Some embodiments may include a float ball in the reservoir to prevent liquid from egressing or being sucked into the manifold during the exhale phase.

Some embodiments may be constructed with some components produced by additive methods such as "stereolithography" and "3D Printing" in addition to the more common molding and machining techniques. Due to biocompatibility, materials compatibility, cost reductions, serviceability, maintainability particularly as relates to the well-known phenomenon of stress cracking in polymers, and techniques for imparting a smooth and or transparent surface economically, certain components may be coated with an epoxy or urethane or other material coatings.

Some embodiments may be constructed with the reservoir or canister having, for the purpose of measurement, graduated markings indicating liquid volume measurements or amounts and are transparent or have a transparent window to observe liquid level. The reservoir or canister being optionally disposable. The reservoir or canister being in fluid communication with and mounted above a lower reservoir or canister also optionally disposable. The upper reservoir or canister being in fluid connection to the breathable liquid/air return line at the top and connected to a breathable liquid/air exhaust line at the bottom. The bottom breathable liquid/air exhaust line being in fluid connection to the top of the lower reservoir or canister. The lower reservoir or canister connected at the bottom to a breathable liquid exhaust line being in fluid connection to the liquid pump or turbine intake port of breathable liquid intended for cooling and re-delivery to the patient.

Further, modified and additional embodiments, features and advantages of the disclosure will become apparent from the detailed description taken in conjunction with the accompanying figures showing illustrative embodiments of the disclosure and the claims.

BRIEF DESCRIPTION OF THE DRAWINGS

The drawings and following associated descriptions are provided to illustrate embodiments of the present disclosure and do not limit the scope of the claims. Corresponding numerals indicate corresponding parts.

FIG. 6B illustrates a perspective view of a proximal part of an example distal flow connector connected to a liquid delivery tube and a liquid recirculation tube arranged in a double helix configuration in accordance with an example embodiment of the present disclosure.

DETAILED DESCRIPTION

Figure 1B:
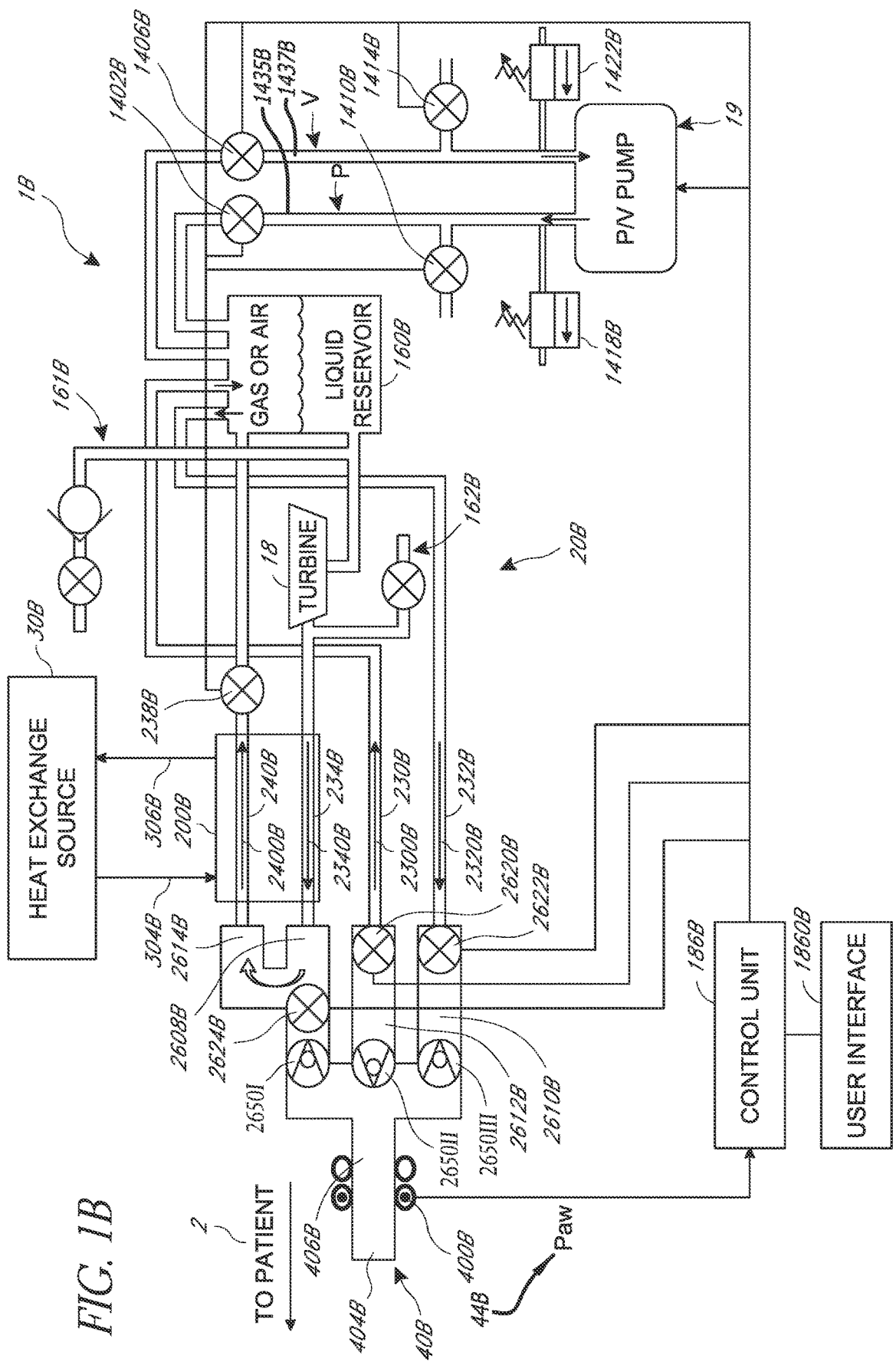
FIG. 1B illustrates a schematic diaphragm of an apparatus in accordance with another example embodiment of the present disclosure.

Embodiments of systems, components and methods of assembly and manufacture will now be described with reference to the accompanying figures, wherein like numerals refer to like or similar elements throughout. Although several embodiments, examples and illustrations are disclosed below, it will be understood by those of ordinary skill in the art that the inventions described herein extends beyond the specifically disclosed embodiments, examples and illustrations, and can include other uses of the inventions and obvious modifications and equivalents thereof. The terminology used in the description presented herein is not intended to be interpreted in any limited or restrictive manner simply because it is being used in conjunction with a detailed description of certain specific embodiments. In addition, embodiments of the inventions can comprise several novel features and no single feature is solely responsible for its desirable attributes or is essential to practicing the inventions herein described.

Although certain aspects, advantages, and features are described herein, it is not necessary that any particular embodiment include or achieve any or all of those aspects, advantages, and features. Some embodiments may not achieve the advantages described herein, but may achieve other advantages instead. Any structure, feature, or step in any embodiment can be used in place of, or in addition to, any structure, feature, or step in any other embodiment, or omitted. This disclosure contemplates all combinations of features from the various disclosed embodiments. No feature, structure, or step is essential or indispensable. Features may also be integrated or subdivided as necessary, such that the any combination of features, whether integrated, separated, removed, added, duplicated, or otherwise recombined fall within the scope of the instant disclosure.

Certain terminology may be used in the following description for the purpose of reference only, and thus are not intended to be limiting. For example, terms such as "above" and "below" refer to directions in the drawings to which reference is made. Terms such as "front," "back," "left," "right," "rear," and "side" describe the orientation and/or location of portions of the components or elements within a consistent but arbitrary frame of reference which is made clear by reference to the text and the associated drawings describing the components or elements under discussion. Moreover, terms such as "first," "second," "third," and so on may be used to describe separate components. Such terminology may include the words specifically mentioned above, derivatives thereof, and words of similar import.

FIG. 1A illustrates schematically an example embodiment of a fluid ventilation apparatus 1A (also referred to as an "apparatus" herein). As will be described below, the apparatus 1A can be used to deliver liquid and/or gas ventilation to the lungs of a mammal, such as a human patient 2 (see FIG. 11). In some embodiments, the apparatus 1A can provide a heated and/or cooled liquid to the lungs. In some embodiments, the apparatus 1A can also provide gas ventilation to the lungs of a patient. For example, in some embodiments, the apparatus 1A provides cooled partial liquid ventilation (PLV) to the lungs. As will be explained below, in certain embodiments, the apparatus described herein can operate in gas ventilation mode, partial liquid ventilation (PLV) mode and/or a total liquid ventilation mode (PLV) and in certain embodiments the apparatus can be configured to switch between such modes. In addition, certain features and aspects of the embodiments described herein can find utility and/or advantages in a device that is configured only for gas ventilation mode, only for partial liquid ventilation (PLV) mode and/or only for total liquid ventilation mode (PLV) or sub-combinations thereof.

The liquid used in the apparatus 1A can be any liquid suitable for being delivered into the lungs of a mammal, for example, any biocompatible fluid, water, saline, and/or perfluorocarbon (PFC). In certain embodiments, the liquid can be an oxygen carrying liquid such as, for example perfluorocarbon (PFC). In certain embodiments, the liquid may or may not be oxygenated prior to the delivery to the lungs. In addition, as noted above, in certain embodiments the liquid can be heated and/or cooled. Gas used in the apparatus 1A can be oxygen, atmospheric air, and/or an anesthetic gas or combinations thereof. In certain embodiments, the gas can be also heated and/or cooled.

The terms "cold", "cooled", "hot," "warm" and their equivalents in this disclosure are relative to the body temperature of a mammal before administration of heat exchange as understood by an artisan. "Cold," "cooled" and their equivalents refer to temperatures below the body temperature of a mammal before administration of heat exchange. "Hot," "warm" and their equivalents refer to temperatures above the body temperature of a mammal before administration of heat exchange.

With continued reference to FIG. 1A, the apparatus 1A can include a delivery device, which in the illustrated embodiment comprises an endotracheal tube 40A having a proximal end 406A and a distal end 404A. In certain embodiments, the delivery device can comprise other devices configured to aid in interfacing with a patient to deliver fluid to a patient's lungs such as a mask and/or nasal cannula and/or a tracheostomy tube and/or device allowing for immersion of the patient in a breathing liquid. The proximal end 406A of the endotracheal tube can be connected to a hub 260A. The hub 260A can have one or more passages for delivering and/or removing fluid to and/or from the delivery device, which as noted above in the illustrated arrangement is an endotracheal tube 40A. In the illustrated embodiment, the hub 260A can include a liquid delivery passage 2608A, a suction passage 2612A, a gas delivery passage 2610A and a recirculation tube passage 2614A. As will be described below, the liquid and/or gas flowing through these passages can be controlled by one or more valves, which can be placed in these passages 2608A, 2612A, 2610A, 2614A.

As shown in FIG. 1A, the hub 260A can be connected to a tube assembly 20A. In one embodiment, the tube assembly 20A can include one or more tubes that correspond to the passages in the hub 260A. In one embodiment, the tube assembly 20A is generally flexible and can have various lengths, and in one example embodiment, the tube assembly 20A can have a length between about 2 to 12 feet. In one arrangement, the tube assembly 20A includes a suction tube 230A that can be in fluid communication with the suction passage 2612A of the hub 260A. The tube assembly 20A can also include a gas delivery tube 232A that can be in fluid communication with the gas delivery passage 2610A of the hub 260A. The tube assembly 20A can also include a liquid delivery tube 234A that can be in fluid communication with the liquid delivery passage 2608A of the hub 20A. The tube assembly 20A can also include a liquid recirculation tube 240A in fluid communication with the recirculation tube passage 2614A of the hub 260A.

The gas delivery tube 232A can be connected to a gas source 60A which can provide pressurized and/or unpressurized air and/or gas to the gas delivery tube 232A. The term "gas source" is a broad term that is intended to comprise any source for pressurized and/or unpressurized air and/or gas such that the gas source 60A can comprise any of a wide variety of sources of pressurized and/or unpressurized air and/or gas such as, for example, a pressurized air and/or gas tank and/or a pump and/or compressor and/or an opening and/or connection to atmospheric air. In a similar manner, the liquid delivery tube 234A can be connected to the fluid reservoir 160A which can comprise a reservoir of liquid and/or a pump for delivering the liquid from the fluid reservoir 160A to the liquid delivery tube 234A. The reservoir can include a gas outlet 162A which can be coupled to a scrubber or similar device configured to remove $CO_2$ from the liquid in the reservoir 160A. The fluid reservoir 160A can also include an inlet 161A through which air, $O_2$ and/or another gas can be introduced into the fluid reservoir 160A. As described herein, in certain embodiments, the patient or subject will be consuming oxygen and throwing off $CO_2$ during a treatment process. The $CO_2$ can be removed from the liquid via the outlet 162A and additional $O_2$ can be added to the liquid via the inlet 161A. The suction tube 230A can be placed in communication with a vacuum source 19A. The fluid reservoir 160A can include a pump 19A' for delivering liquid from the fluid reservoir 160A through the liquid delivery tube 234A and the liquid delivery passage 2608A and to the delivery device 40A. The vacuum source 19A can be used to apply suction or vacuum through the suction tube 230A, the suction passage 2612A and the delivery device 40A. In the illustrated embodiment, the suction tube 240 can also be in fluid communication with the fluid reservoir such that any liquid withdrawn through the suction tube 240 can be returned to the fluid reservoir 160A. As will be explained below, in certain embodiments, a single pump can be used to alternatively replace or with the fluid reservoir 160A under pressure or under vacuum such that the fluid reservoir can function as the vacuum source in communication with the suction tube 230A and/or the pressure source in communication with 234A.

In the illustrated embodiments, the suction tube 230A, the gas delivery tube 232A, the liquid delivery tube 234A and the liquid recirculation tube 240A are shown as separate components from the hub 260A and the associated passages 2612A, 2601A, 2608A, 2614A within the hub 260A. In certain embodiments, these components can be combined such that the passages and tubes form a single component and/or additional components can be provided between these tubes and passages.

The distal end 404A of the endotracheal tube 40A can be configured to be inserted into the human patient 2's airway (trachea). The distal end 404A of the endotracheal tube 40A can also include a pressure sensor 400A that can measure a human patient's airway pressure $P_{aw}$ 44A when the endotracheal tube 40A is positioned within the patient 2. As used herein the term "pressure sensor" is intended to include any of a variety of sensors that can provide a signal and/or other indication that is directly and/or indirectly indicative of pressure at a desired location. Accordingly, the pressure sensor 400A can comprise any of a variety of sensors that are indicative of pressure at a desired location such as, for example, conventional electric pressure sensors that measure or sense strain or deflection due to pressure and/or Micro-Electro-Mechanical Systems (MEMS) and/or an optic based systems and/or the pressure sensing apparatuses and fiber optic pressure sensors described in U.S. Pat. Nos. 8,022,835; 7,284,436; 7,096,737; and/or 6,604,427, which are incorporated by reference herein in their entirety for all purposes. In the illustrated embodiment, the pressure sensor 400A is illustrated as positioned on the endotracheal tube 40A. In certain embodiments, the pressure sensor 400A can be positioned at a location remote from the endotracheal tube 40A but connected through a pilot tube or similar apparatus with an opening on or near the endotracheal tube 40A and/or a connection of the endotracheal tube 40A to the hub 260A. In one embodiment, the pressure sensor 400A can be part of a balloon cuff, the details of certain embodiments will be provided below. The pressure sensor 400A advantageously can be configured to sense pressure change when only gas is delivered, when a mixture of gas and liquid is delivered, and/or when only liquid is delivered by the apparatus 1A. The endotracheal tube 40A can optionally feature a lumen in the wall, in addition to any lumen(s) used for cuff inflation, which ends at or near the distal end of the tube. The pressure sensor 400A can be incorporated into this lumen.

As shown in FIG. 1A, the pressure sensor 400A can be operatively connected to a control unit 186A. The control unit 186A can use the information from the pressure sensor 400A to output electrical signals and/or instructions (as described below) to control the flow of the liquid and gas between the tube assembly 20A and the endotracheal tube 40A by controlling opening and closing of one or more two-way valves (described below) that can be provided in the hub 260A and/or in other parts of the apparatus 1A, such as a manifold as described in a later illustrated embodiment. Accordingly, in the illustrated arrangement, the control unit 186A can be operatively connected to a suction valve 2620A, a gas delivery valve 2622A and/or a liquid delivery valve 2624A. The control unit 186A can also be operatively connected to a recirculation valve 238A. These valves 2620A, 2622A, 2624A, 238A can be two-way valves selected from a variety of types of valves. In one embodiment, the two-way valves are pneumatically piloted valves. Opening and closing of the two-way valves 2620A, 2622A, 2624A, 238A according to the signals sent by the control unit 186A can be done by any conventional actuators, such as electrical, hydraulic or pneumatic actuation. In one embodiment, the two-way valves comprise piloted valves, which are controlled by smaller pilot solenoid valves, which in turn can be three way valves or triple ported valves. The apparatus 1A can include additional sensors and/or switches such as adjustable pressure switches, vacuum sensors, adjustable vacuum switches, pressure meters, vacuum meters and/or thermometers.

Figure 12:
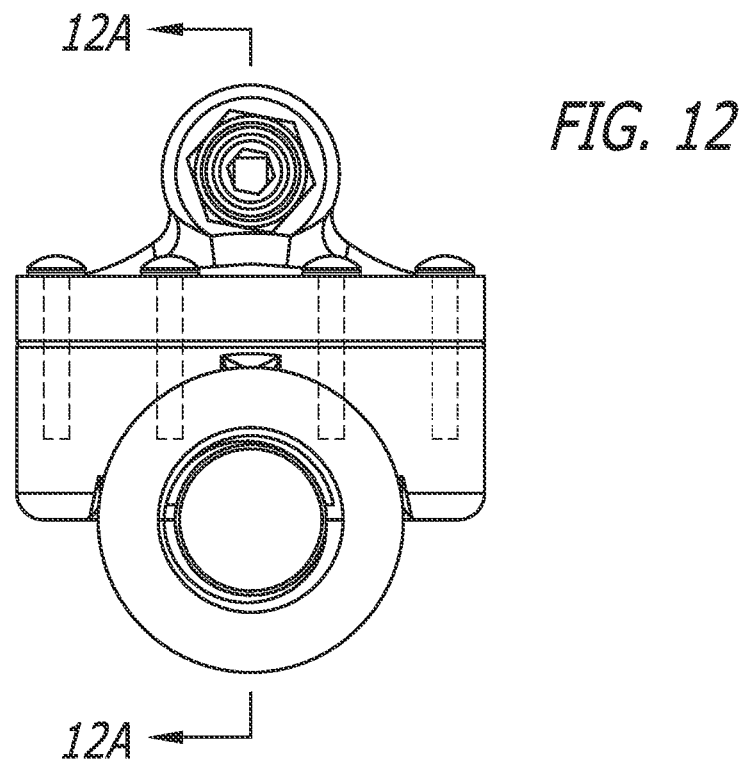
FIG. 12 illustrates an exemplary contoured diaphragm to create a sealing surface for valves according to embodiments described herein.
Figure 12A:
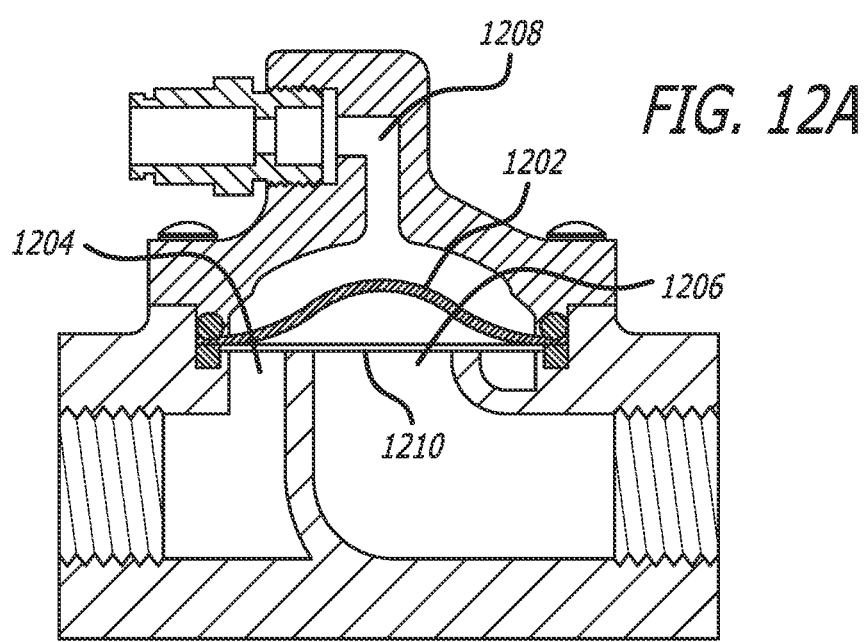
FIG. 12A illustrates an exemplary cross section of FIG. 12.

In an exemplary embodiment, valves described herein may include a diaphragm. FIG. 12 illustrates an exemplary contoured diaphragm to create a sealing surface for the valve. As shown, the valve is normally open, and closes with the application of pressure. However, the valve may be normally closed. The valve may also be opened with pressure and/or opened or closed with a vacuum. As shown, having a normally open valve that opens with a change in pressure permits one of the pressure sources to be removed from the system. For instance, the vacuum pump may be removed, and a single pump used to control the valves. In this case, the valve may be controlled by applying a greater than atmospheric pressure to close the valve, and applying atmospheric pressure or simply opening the line to atmosphere to open the valve. As illustrated in the cross section of FIG. 12A, the valve includes a diaphragm 1202 in a normally open configuration that permits to and from flow between a first opening 1204 and a second opening 1206. As shown, the first and second openings are in a common plane 1210 and positioned on the same side of the diaphragm. The valve diaphragm in a relaxed or normal configuration is in contact with the plane containing the first and second opening at an outer perimeter of the diaphragm and out of contact with the plane on an interior region of the diaphragm. For example, the diaphragm may be curved or dome shaped. The valve may include a control opening 1208 on an opposite side of the diaphragm from the first and second opening. The control opening configured to supply pressure or vacuum or remove pressure or vacuum to control the position of the diaphragm, such as in either a closed or open configuration. There may be a spring element incorporated into the valve to cause or assist closure, or the diaphragm may be configured such that it returns to some shape with removal of the controlling pressure or controlling vacuum.

In this disclosure, various components are described as being "operatively connected" to the control unit. It should be appreciated that this is a broad term that includes physical connections (e.g., electrical wires) and non-physical connections (e.g., radio or infrared signals). It should also be appreciated that "operatively connected" includes direct connections and indirect connections (e.g., through an additional intermediate device, control unit or processor). In various embodiments, the control unit 186A may include one or more processors, one or more memories, and one or more communication mechanisms. In some embodiments, more than one control unit may be used to execute the modules, methods, and processes discussed herein. Additionally, the modules and processes herein may each run on one or multiple processors, on one or more control units or processes; or the modules herein may run on dedicated electrical hardware and may have non-dedicated peripherals, data storage, data sharing, diagnostics, virtually real time monitoring and post data processing and analysis such as with cloud communications. The control unit 186A may include an input device such as one or more keyboards (one-handed or two-handed), a mouse, touch screens, voice commands and associated hardware, gesture recognition, or any other device or method of providing communication between an operator and the control unit 186A.

The hub 260A can connect the proximal end 406A of the endotracheal tube 40A to the tube assembly 20A. In the illustrated embodiment, the suction valve 2620A, the gas delivery valve 2622A, and the liquid delivery valve 2624A can be located in the hub 260A. In other words, in the illustrated embodiment, these three valves 2620A, 2622A, 2624A can be located near a distal end of the tube assembly 20A. In the illustrated embodiment, the recirculation valve 238A can be located at a location nearer to a proximal end of the tube assembly 20A and closer to the fluid reservoir 160A than the other three valves 2620A, 2622A, 2624A. In modified embodiments, the location of these valves 2620A, 2622A, 2624A, 238A can be modified. In the illustrated embodiment, having the suction valve 2620A, the gas delivery valve 2622A and the liquid delivery valve 2624A located on the hub 260A can advantageously reduce an overall size of the tube assembly 20A. In certain embodiments, these valves 2620A, 2622A, 2624A can be located at other parts of the apparatus 1A. In the illustrated embodiment, the liquid delivery tube 234A, the liquid recirculation tube 240A and the suction tube 230A can also be connected on a proximal end to the single fluid reservoir 160A. In some embodiments, the liquid recirculation tube 240A and the suction tube 230A can be connected to a top of the fluid reservoir 160A to return the liquid to the fluid reservoir 160A and the liquid delivery tube 234A can be connected a bottom of the fluid reservoir 160A to collect the liquid. One of the advantages of having a single fluid reservoir is to reduce the size and weight of the apparatus 1A and to reduce the need for refilling the reservoir with fresh liquid because at least a portion of the liquid leaving the fluid reservoir 160A is recycled back to the fluid reservoir 160A via the liquid recirculation tube 240A and the suction tube 230A. Other advantages of the single fluid reservoir will be discussed below.

While a single fluid reservoir has certain advantages, in certain arrangements, the apparatus 1A can be provided with more than one fluid reservoir. For example, one or more of the liquid delivery tube 234A, the liquid recirculation tube 240A and the suction tube 230A can be connected to separate reservoirs. In certain embodiments, one or more of directions of flow 2300A, 2320A, 2340A, and 2400A may additionally be driven by one or more pumps (not shown in FIG. 1A) that are capable of exerting pressure or negative pressure (vacuum) on the liquid or the gas. In the illustrated embodiment, the gas delivery tube 232A can also connected to the gas source 60A, which can be atmospheric air, a source of anesthetic gas, or other types of ventilation gas according to the need of the patient 2. Multiple containers may serve the purpose of preventing liquids from entering certain parts of the machine.

The control unit 186A can be configured to send control signals to open and/or close the suction valve 2620A, the gas delivery valve 2622A, the liquid delivery valve 2624A and/or the recirculation valve 238A based on changes in the human patient's or animal's airway pressure ($P_{aw}$) 44A according to certain protocols and/or control routines as described herein. In certain embodiments, the timing of opening and closing of some of the valves may be synchronized. For example, the liquid delivery valve 2624A and the gas delivery valve 2622A can be closed at the same time as the suction valve 2620A is opened when $P_{aw}$ 44A reaches a predetermined maximum threshold pressure value and the apparatus 1A switches from an inhale phase to an exhale phase. The liquid and the ventilation gas that has been delivered inside the patient's lungs can be vacuumed from the lungs via the suction tube 230A under a vacuum, with the removed liquid returned to the fluid reservoir 160A and the removed gas pumped out of the fluid reservoir 160A and released into the atmosphere or captured in an external capture system in certain embodiments. During the exhale phase, vacuum extraction can additionally aid removal of carbon dioxide from the removed liquid due to lower partial pressure of carbon dioxide in the vacuum than in the liquid. In certain embodiments, the liquid delivery valve 2624A and the gas delivery valve 2622A can be closed independently at different times instead of closing simultaneously. During the exhale phase, the recirculation valve 238A can also be opened at the same time so that the liquid can be recirculated back to the fluid reservoir 160A and thus can receive in the certain embodiment additional heat extraction. The predetermined threshold pressure and/or the preset vacuum can be adjusted and/or set by the user of the apparatus for example by using an input device associated with the control unit 186A.

Reversely, during an inhale phase, the suction valve 2620A can be closed when $P_{aw}$ 44A reaches a predetermined minimum threshold pressure value and the apparatus 1A switches from an exhale phase to an inhale phase. During the inhale phase, the liquid delivery valve 2624A and the gas delivery valve 2622A can open at the same time the suction valve 2620A is closed. Again, the liquid delivery valve 2624A and the gas delivery valve 2622A can be opened simultaneously or independently. The gas and/or the liquid can then be delivered to the endotracheal tube 40A under a pressure. Pressured delivery of the liquid may help oxygenate the liquid delivered to the patient 2 because the partial pressure of oxygen can be higher in the inhaled fresh air or other supplied gas than in the liquid. In certain modified embodiments, the control unit 186A can be configured to open and close the suction valve 2620A, the gas delivery valve 2622A, the liquid delivery valve 2624A and the recirculation valve 238A according to other timing schedules, such as adding a delay to the opening or closing of any of the valves and/or in response to other sensed values. In certain embodiments, the apparatus 1A can be used as a time division multiplexed blender. For example, in certain embodiments, using time division multiplexing, timing schedules can be configured to precisely mix multiple gasses and/or liquids and/or gasses to synthesize a prescribed blend, which can be delivered to the lungs. In certain example arrangements, gasses could be added on a breath by breath basis, for example, trace gasses could be added in defined percentages to perform diagnostics such as the addition of helium or acetylene for the purpose of metabolic rate measurements with the addition of complementary diagnostic devices. In certain embodiments, the apparatus 1A can be configured with a user controlled setting such that Partial Liquid Ventilation ("PLV") and/or Total Liquid Ventilation ("TLV") can be provided to the patient via control of the fluid reservoir 160A, and/or control of the gas delivery tube 232A, and/or control of the gas delivery valve 2622A. Applicant's current understanding based on experiments is that Partial Liquid Ventilation has the advantage of keeping the alveoli open and receptive to subsequent filling with liquid, increasing thermal exchange efficiency, while keeping some normal gas to gas exchange in the presence of the liquid. Nevertheless, in certain embodiments of the apparatuses described herein PLV and/or TLV may be beneficially provided according to the needs of the patient, such as life support, lung lavage and/or needs of the environment, and/or to closely maintain the materials that have been in contact with the patient.

The predetermined threshold pressure can be achieved in a variety of circumstances. For example, the lungs could have filled to their volume available with the fluid and gas by the apparatus. Alternatively, CPR could have been applied, exerting a pressure equal to or exceeding the predetermined threshold pressure in the lungs. Another possibility would be that the patient attempts to breathe on his or her own. An advantage to certain embodiments of the apparatus described herein is that the apparatus can be sensitive to pressure change from a CPR procedure or a patient's own breathing in addition to active filling by the apparatus so that active filling can stop as soon as the pressure in the patient's airway reaches the threshold regardless of how the threshold pressure is achieved, thereby minimizing harm to the patient and/or and acting as a breathing aid to a patient not fully capable of breathing on his/her own.

Also as shown in FIG. 1A, a heat exchanger 30A can be provided to the tube assembly 20A to heat and/or cool the gas and/or liquid flowing through the tube assembly 20A, thereby providing heated and/or cooled liquid and/or heated and/or cooled ventilation gas to the lungs of the patient. In a modified embodiment, the entire apparatus 1A or portions thereof can be heated and/or cooled including the fluid reservoir 160A and/or gas supply 60A. Providing the heat exchanger 30A at the tubing assembly 20A instead of at or close to the fluid reservoir 160A can advantageously eliminate or reduce the need for a bulky heat exchange manifold in connection with the fluid reservoir 160A, which can in certain embodiments reduce the overall size and weight of the apparatus, and also can in certain embodiments reduce the cooled liquid and/or gas warming up or heated liquid and/or gas cooling down in the delivery tubes. In certain embodiments, the already cooled or heated liquid in the liquid recirculation tube 260A returns to the same fluid reservoir 160A, which can provide even more efficient cooling or heating of the liquid.

FIG. 1B illustrates another example embodiment of a fluid ventilation apparatus 1B (also referred to as an "apparatus" herein), which can be used to deliver liquid and/or gas ventilation to the lungs of a mammal, such as a human patient 2. As with the embodiment of FIG. 1A, the apparatus 1B can provide a heated and/or cooled liquid to the lungs. In some embodiments, the apparatus 1B can also provide gas ventilation to the lungs of a patient. For example, in some embodiments, the apparatus 1B provides cooled partial liquid ventilation (PLV) to the lungs. For another example, in some embodiments, or in the same embodiment, the apparatus 1B provides cooled total liquid ventilation (TLV) to the lungs as controlled by a user controlled or automatic setting, or conventional gas ventilation as controlled by a user controlled or automatic setting, or any of PLV, TLV and conventional gas ventilation modes at different times as required. An advantage of certain embodiments is that if no liquid is present in the fluid reservoir 160A, 160B, the apparatus 1A, 1B can function as a dry ventilator. This may be due to the use of the apparatus 1A, 1B as a dry ventilator, and/or in the emergency application, the liquid simply has not been added to the fluid reservoir 160B yet and/or has left the system such as through evaporation, and/or through faults in the system or the patient or animal, and/or the apparatus 1B is being used as a lavage and the liquid in the fluid reservoir 160B is in the process of being cleaned replace, renewed and/or oxygenated. As noted above, the fluid reservoir 160B can include an outlet which can be used to drain liquid from the fluid reservoir 160B such that the apparatus 1B can be used as dry ventilator. Features of the embodiment of FIG. 1B corresponding to those described with reference FIG. 1A are referenced by the same reference numerals but ending with "B" instead of A". Accordingly, the apparatus of FIG. 1B can be similar to the apparatus 1A of FIG. 1A except as described differently below. In certain arrangements, the features of the apparatus 1B can be incorporated into the apparatus 1A and the features of the apparatus 1A can be incorporated into the apparatus 1B. Features of FIGS. 1A and 1B may be combined or substituted as required to achieve the desired objective. The disclosed embodiments are exemplary only and not mutually exclusive.

With continued reference to FIG. 1B, the apparatus 1B can include a delivery device, which in certain embodiments can be an endotracheal tube 40B having a proximal end 406B and a distal end 404B. In certain embodiments, the delivery device can comprise other delivery devices configured to aid in interfacing with a patient to deliver liquid and/or gas to a patient's lungs such as a mask and/or nasal cannula and/or device allowing for immersion of the patient in a breathing liquid. The proximal end 406B of the endotracheal tube can be connected to a hub 260B. The hub 260B can have one or more passages for delivering and/or removing liquid or gas to and/or from the endotracheal tube. In the illustrated embodiment, the hub 260B includes a liquid delivery passage 2608B, a suction passage 2612B, a gas delivery passage 2610B and a recirculation tube passage 2614B. As will be described below, the liquid and/or gas flowing through these passages can be controlled by one or more valves, which are placed in the passages.

As shown in FIG. 1B, the hub 260B can be connected to a proximal end 406B of a tube assembly 20B. In one embodiment, the tube assembly 20B includes one or more tubes that correspond to the passages in the hub 260B. In one embodiment, the tube assembly 20B is generally flexible and can have lengths and in one embodiment can be about 2 to 12 feet in length. Similar to the tube assembly 20A, the tube assembly 20B can comprise a heat exchanger 200B, which can connect to a heat exchange source 30B via a heat exchange inlet 304B and a heat exchange outlet 306B. In one arrangement, the tube assembly 20B includes a suction tube 230B that can be in fluid communication with the suction passage of the hub. The tube assembly 20B can also include a gas delivery tube 232B that can be in fluid communication with the gas delivery passage 2610B of the hub. The tube assembly 20B can also include a liquid delivery tube 234B that can be in fluid communication with the liquid delivery passage 2608B of the hub. The tube assembly can also include a liquid recirculation tube 240B in fluid communication with the recirculation tube passage 2614B of the hub.

The hub 260B can include a plurality of two-way valves 2620B, 2622B, 2624B, which are respectively positioned within the suction, the gas delivery, and the liquid delivery passages of the hub 260B. In addition, the hub 260B can include a plurality of one-way check valves 2650I, 2650II, 2650III within the liquid delivery, the suction, and/or the gas delivery passages respectively. The check valve 2650I in the liquid delivery passage 2608B only allows liquid to flow from the tube assembly 20B to the endotracheal tube 40B and is located distally of the liquid delivery valve 2624B. The check valve 2650III in the gas delivery passage only allows gas to flow from the tube assembly 20B to the endotracheal tube 40B and is located distally of the gas delivery valve 2622B. The check valve 2650II in the suction passage can be configured to only allow liquid and/or gas along with any suspended solids to flow from the endotracheal tube 40B to the tube assembly 20B and is located distally of the suction valve 2620B. More specifically, the check valve 2650I can be configured to only open in the direction 2340B that allows a liquid to flow from a liquid delivery tube 234B to the endotracheal tube 40B. The check valve 2650III can be configured to only open in the direction 2320B that allows the air and/or oxygen and/or other gases to flow from a gas delivery tube 2320B to the endotracheal tube 40B. The check valve 2650II can be configured to only allow flow in the direction 2300B that allows a mixture of liquid(s) and gas(es) that was in the patient's lungs to flow from the endotracheal tube 40B to the suction tube 230B. In certain embodiments, having the check valves advantageously provides additional safety of the apparatus 1B by ensuring that directions of flow in the hub 260B are as intended and also reducing the likelihood of backflow of the gas and/or liquid in the tube assembly 20B. In some embodiments, additional one-way check valves may be places in other tubes of the apparatus 1B. In certain embodiments, the check valves can be used to enable differential timing of fluid with automatic dry ventilation.

The apparatus 1B can also include a turbine pump 18 between a fluid reservoir 160B, which will be described below, and the liquid delivery tube 234B. The turbine pump 18 can be small in size and light in weight, but can be powerful enough to advantageously draw the liquid out of the fluid reservoir 160B and eventually to the endotracheal tube 40B faster than without the turbine pump 18, which in certain embodiments can make the apparatus 1B more efficient. In certain embodiments, the turbine pump 18 advantageously has no seals like in a piston pump or liquid contacting diaphragms, which can make the turbine pump 18 easy to be incorporated into the apparatus 1B. In certain embodiments, the turbine pump 18 can advantageously also run dry of liquid, and can continue to run without damage if there are stoppages of the flow of liquid through it. While the turbine pump 18 has certain advantages as described above, in other embodiments, a different type of pump can be used.

The turbine pump 18 can include an aerator feature 161B as shown in FIG. 1B, which in certain embodiments can advantageously aerate the liquid by withdrawing gases allowed into the aerator feature 161B and causing them to be dissolved into the liquid via agitation and size reduction of the bubbles in the liquid(s) as the liquid(s) passes through the turbine pump 18. The aerator feature 161B also can be advantageously used as a point to fill the system with liquid while it is running and providing gas ventilation to the patient as liquid will be drawn through this aerator feature 161B during the exhale phase. In some embodiments, the aerator feature 161B can comprise a valved connector and a check valve. In some embodiments, the aerator feature 161B can be located at an inlet side of the turbine pump 18. The aerator feature 161B may be one used in a conventional bait pump or other types of aerator features, such as tall bubblers and gas exchange surfaces. Using the aerator feature of the bait pump can advantageously provide a lowered cost and reduce size and weight of the apparatus 1B. Oxygen in the air bubbles that are not absorbed into the liquid due to agitation at evacuation or agitation by a turbine of the turbine pump 18 can be absorbed within the travel in the tube assembly 20B. The turbine pump 18 may also be used to emulsify water or saline, or other liquids or compounds, into the fluid, such as PFC, to improve thermal properties before the heavier PFC separates from water or saline. Thermal capacitance of water is several times higher than PFC and therefore improves the thermal performance of the liquid delivered to the patient when water or saline is emulsified into PFC. Thus, in certain embodiments, the liquid delivered to the patient can be cooled or heated by emulsifying a cooled or heated first liquid (e.g., water or saline, and/or other liquids) in to the second liquid (e.g., PFC) intended to be delivered to the lungs. Accordingly, in one example embodiment, PFC can be cooled by emulsifying water from recently melted ice into the PFC before it is delivered to the lungs. A gas outlet 162B can be located at an outlet side of the turbine pump 18. The gas outlet 162B can be coupled to a scrubber or similar device configured to remove $CO_2$ from the liquid in the reservoir 160B.

With continued reference to FIG. 1B, similar to the tube assembly 20A, the liquid delivery tube 234B, the liquid recirculation tube 240B and the suction tube 230B can be connected to the single fluid reservoir 160B. The liquid recirculation tube 240B and the suction tube 230B are connected to a top portion of the fluid reservoir 160B and the liquid delivery tube 234B is connected to a bottom portion of the fluid reservoir 160B. Unlike the tube assembly 20A, the gas delivery tube 232B can also be connected to the top portion of the fluid reservoir 160B instead of directly to a gas source. Supply of gas to the gas delivery tube 232B will be described in detail below.

Also as shown in FIG. 1B, the apparatus 1B can include a pressure/vacuum ("P/V") pump 19 connected to the fluid reservoir 160B. The P/V pump 19 switches between a pressure state and a vacuum state as the apparatus 1B switches between an inhale phase and an exhale phase, making pressure P on one side and vacuum V on another side of the pump 19. More particularly, in certain embodiments, the P/V pump 19 can apply pressure P via a pressure line 1435B to the fluid reservoir 160B to push the liquid in the fluid reservoir 160B to enter the liquid delivery tube 234B (in addition to the turbine pump 18) when the apparatus 1B is in the inhale phase. The gas delivery tube 230B is in fluid communication with the top portion of the reservoir 160B so that gas from the P/V pump 19 enters into the reservoir 160B in a space not occupied by liquid. Gas in this space is also pushed into the gas delivery tube 232B by the P/V pump 19 in the inhale phase. The same P/V pump 19 can apply vacuum V via a vacuum line 1437B to the top portion of the fluid reservoir 160B to cause the liquid and/or gas from the suction tube 230B to enter the fluid reservoir 160B when the apparatus 1B is in the exhale phase. In one embodiment, the single pump 19 can be a diaphragm pump. In some embodiments, the P/V pump 19 can run continuously. In certain embodiments, having one state-switching pump can advantageously result in fewer components, reduced weight and lower power consumption for the apparatus 1B.

A pressure relief valve 1418B can be located on the pressure side of the P/V pump 19. A vacuum relief valve 1422B can be located on the vacuum side of the P/V pump 19. Any excess pressure or vacuum building up in the apparatus or in the patient's lungs can be released through the relief valves. The relief valves are optional and can protect the safety of the patient when abnormal $P_{aw}$ 44B, as well as protect the reservoir 160B and other components if excessive pressure or vacuum are generated or when the apparatus malfunctions, such as when there is a potential overpressure or excessive vacuum condition. The relief valves can also advantageously provide greater reliability and safety of the apparatus 1B without the need for pressure sensor or controls that are required on a large P/V pump, allowing a smaller, lighter and cheaper pump to be used. In some embodiments, the relief valves comprise adjustable spring-loaded diaphragms. However, exemplary embodiments may not include relief valves 1418B and/or 1422B as the control system may prevent over or under pressure within the system.

Returning to the endotracheal tube 40B, the distal end 404B of the endotracheal tube 40B can be configured to be inserted into the human patient 2's airway (trachea). The distal end 404B of the endotracheal tube 40B can include a pressure sensor 400B that measures a human patient's airway pressure $P_{aw}$ 44B while the apparatus 1B delivers liquid and/or gas ventilation to the lungs of the patient 2. Similar to the apparatus 1A, the pressure sensor 400B can be directly or indirectly coupled to a control unit 186B. The control unit 186B in turn can output instructions controlling the opening and closing of the valves 1402B, 1406B, 1410B, 1414B connected to the P/V pump 19 as well as the valves 238B, 2620B, 2622B, 2624B according to signals from the pressure sensor 400B as described above with respect to apparatus 1A of FIG. 1A, thereby deciding whether the apparatus is in the inhale phase (under P) or the exhale phase (under V). In some embodiments, the control unit 186B can comprise a user interface 1860B for turning the apparatus 1B on and off and/or controlling the operating parameters of the apparatus 1B such as, for example, the duration of an inhale and/or exhale phase and/or the timing and/or delay of such phase and/or the timing and/or delay of the delivery of liquid as compared to gas delivery. In certain embodiments, the user interface 1860B includes one or more magnetic switches. For example, that user interface 1860B can include an "on"/"off" magnetic switch, such as, for example, a vacuum envelop isolated magnetic reed switch construction, which prevent arcing into a flammable atmosphere. Use of such magnetic switches in the apparatus 1B can advantageously decrease fire risk when flammable gases are present.

As with many features and aspects described in this disclosure, the use of a magnetic switch that does not create sparks or arcing can also find utility and be advantageous when used in combination with a conventional gas ventilation device, and/or other apparatuses configured for ventilation, TLV and/or PLV and need not be used in combination with the features of the embodiments described herein. In certain embodiments, the primary pressure and vacuum lines from 19 to 160B can optionally include variable restrictors to control the cadence, or breath rate of the apparatus 1B.

In an exemplary embodiment, the turbine pump 18 can be controlled by the pressure in the fluid reservoir 160B. In this case, the circuitry to control unit 186B associated with the valve 238B can be removed, thereby simplifying the supporting electronics to the system. For example, when a pressure in the fluid reservoir reaches or surpasses a preset or programmable threshold, the turbine may activate, sending liquid to the patient. At the beginning an inhale phase, the suction valve 2620B can be closed when $P_{aw}$ 44B reaches a predetermined threshold pressure value and the apparatus 1B switches from an exhale phase to an inhale phase. During the inhale phase, the liquid delivery valve 2624B and the gas delivery valve 2622B can open at the same time the suction valve 2620B is closed. Again, the liquid delivery valve 2624B and the gas delivery valve 2622B can be opened simultaneously or independently. The gas and/or the liquid can then be delivered to the endotracheal tube 40B under a pressure. The pump 19 may supply pressure to move gas and/or liquid from the reservoir 160B to patient 2. Once the pressure reaches a predetermined value, the turbine 18 may turn on and assist with liquid delivery to the patient.

Turning to state switching of the apparatus 1B, in certain embodiments in which no liquid is delivered, during the inhale phase of the apparatus 1B, the valve 1410B closes and the valve 1402B opens so that air or gas from the P/V pump 19 pressurizes the reservoir 160B. The valve 1414B opens and the valve 1406B closes so that air or gas is taken in at an opening to the valve 1414B. The gas delivery valve 2622B opens to admit air or gas from the top portion of the now pressurized reservoir 160B in the space above the liquid if any is present in this volume. The suction valve 2620B can be kept closed during the inhale phase, aided by the check valve 2650II. Air or gas can continue to flow into the patient until a certain desired pressure is reached. The desired pressure can result from filling the lungs or compression of the lungs via manual or machine driven CPR. The apparatus 1B can switch to the exhale phase at the desired pressure.

During the exhale phase, the valve 1410B opens and the valve 1402B closes so that air or gas from the P/V pump 19 is released as exhaust into the atmosphere, or optionally to an exhaust collection device (not shown). The valve 1414B closes and the valve 1406B opens so that the reservoir 160B is under vacuum (V). The gas delivery valve 2622B also closes. The liquid delivery valve 2624B may be in the closed condition to prevent liquid delivery and/or the reservoir 160B may simply be empty of liquid by intent or circumstance. The suction valve 2620B opens so now the vacuumized reservoir 160B can draw gas/air from the patient until a desired level of vacuum in the lungs is achieved. These embodiments could allow for full gas ventilation for life support of the patient if there is no liquid in the reservoir. A dry snorkel could be substituted for the wet heat exchange snorkel when exclusive use as a dry ventilator is expected. Such scenarios can happen when the reservoir has not yet been filled, when the apparatus is being used as a standard pressure sensitive gas ventilator, or when a user optionally stops liquid delivery or when injury or defect has allowed loss of the available liquid. The apparatus can do so without requiring additional sensors, controls or other types of equipment.

In some embodiments in which liquid is also delivered, in additional to the states of the valves as described above for the embodiments involving no liquid delivery, additional opening and closing of some valves can be involved. For example, during the inhale phase before $P_{aw}$ 44B reaches a predetermined threshold pressure value, the apparatus 1B can provide only gas to the patient 2 via the gas delivery tube 232B of the tube assembly 20B first. After a short delay during which the gas is being delivered, the liquid can overpower the lower pressure gas to close the check valve 2650III. The liquid can then be the dominant or only fluid being delivered to the patient. The short delay can be the amount of time taken for the liquid to reach the hub 260B, and/or approximately 90 milliseconds after the inhaling of gas or air. When liquid is the dominant or only fluid being delivered to the patient, the liquid recirculation valve 238B can close to terminate looping of the liquid through the heat exchanger 200B and the liquid delivery valve 2624B can open to admit liquid into the patient. The suction valve 2620B can be kept closed during the inhale phase, aided by the check valve 2650II. Once the $P_{aw}$ 44B reaches the predetermined maximum threshold pressure value, the liquid delivery valve 2624B can be closed and the liquid recirculation valve 238B can open, allowing the liquid to "short circuit" into the reservoir 160B without entering the patient. The suction valve 2620B can open so now the vacuumized reservoir 160B can draw fluid (a mix of gas/air and the volume of liquid beyond the reserve volume of the lungs) from the patient until a desired level of vacuum in the lungs is achieved. The desired level of vacuum in the lungs can be associated with the desired removal of fluid but should be below any level of vacuum that would cause injury or airway collapse of a patient. The reserve volume of the lungs is the part of the lung volume that cannot be exhaled and is approximately 1 liter in humans.

Figure 1C:
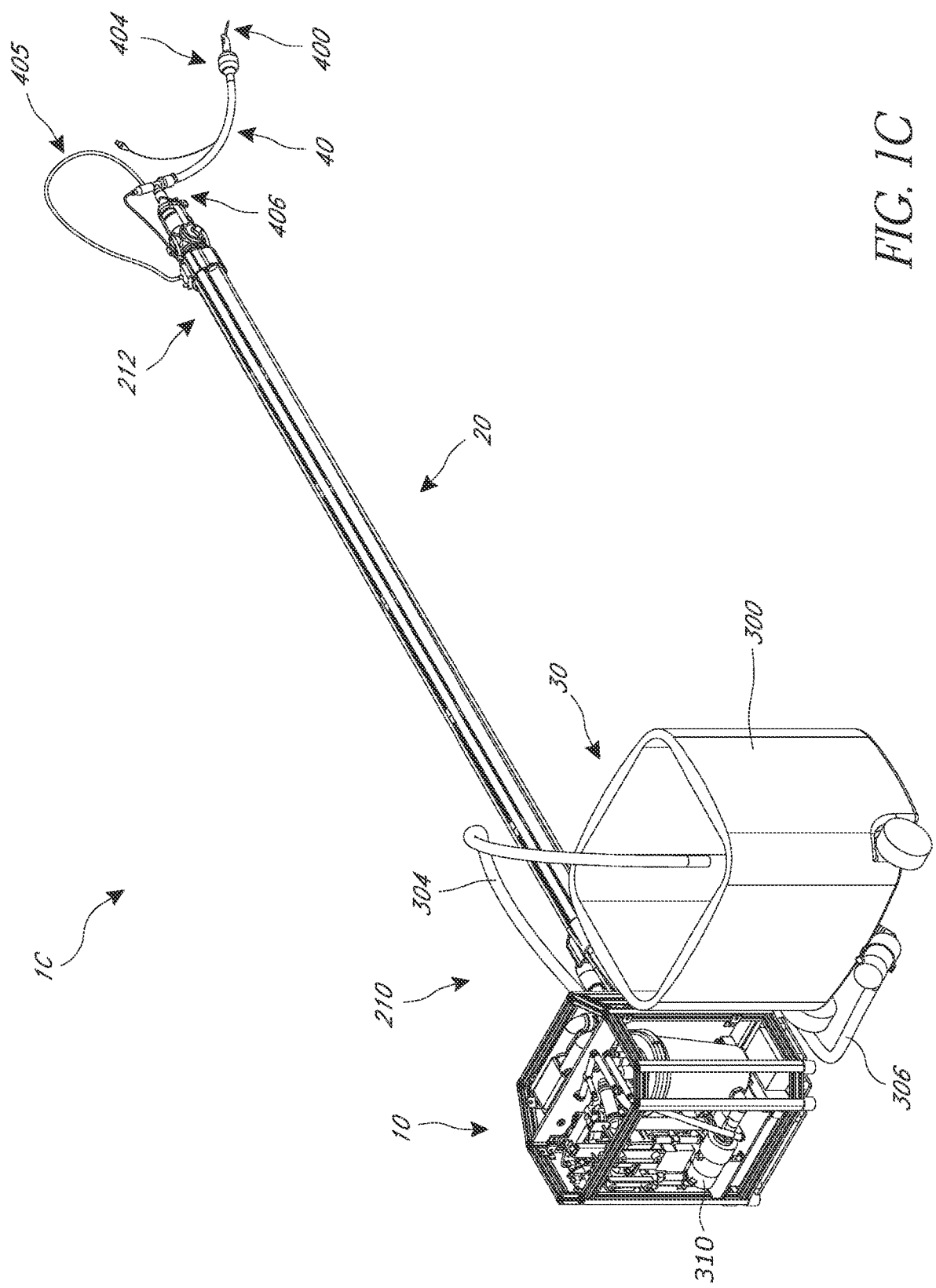
FIG. 1C illustrates a perspective view of an apparatus in accordance with yet another example embodiment of the present disclosure.
Figure 1D:
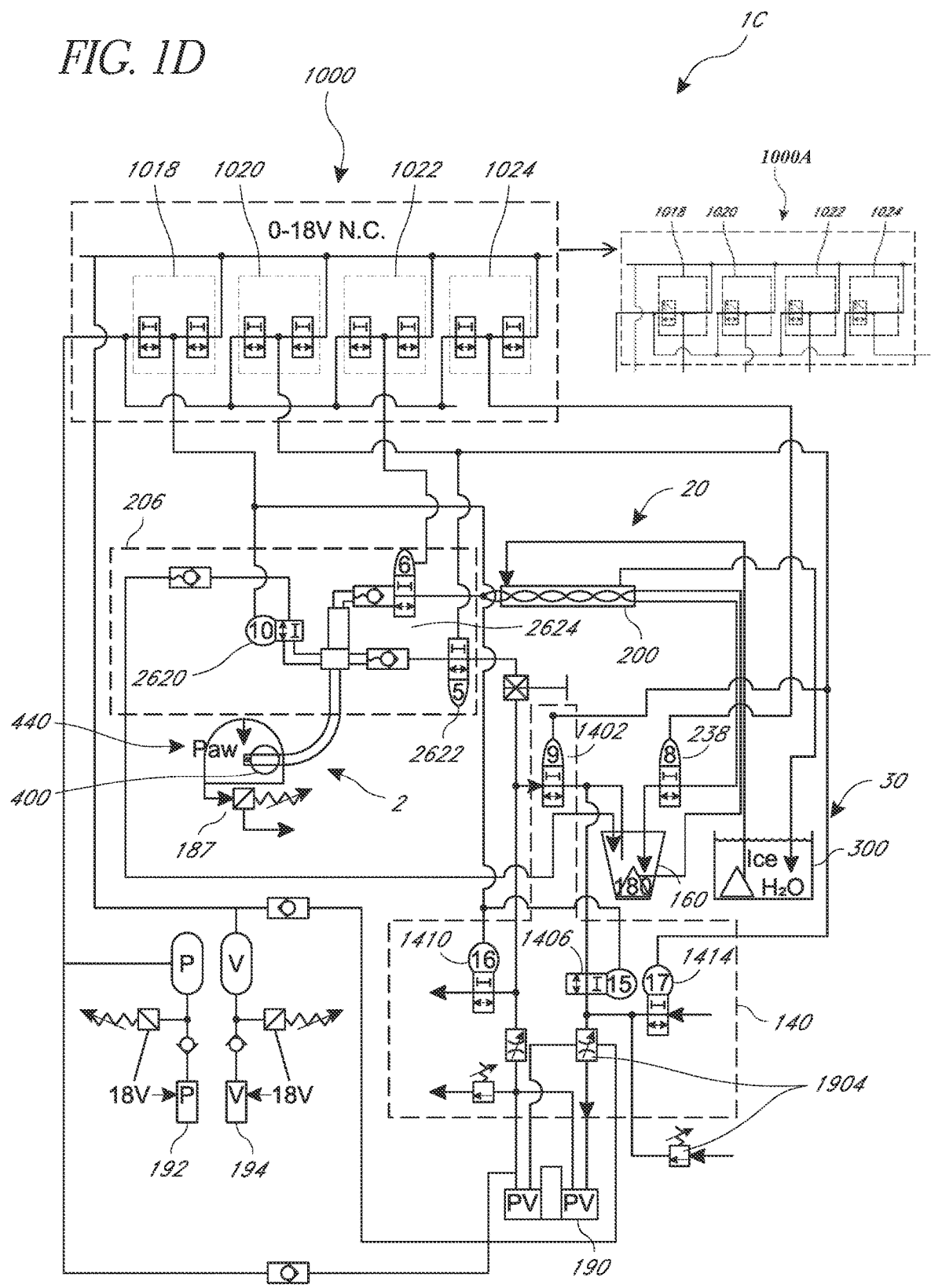
FIG. 1D is a block diaphragm illustrating operation of an apparatus in accordance with the example embodiment of the present disclosure shown in FIG. 1C.

FIGS. 1C-D illustrate another example embodiment of a liquid ventilation apparatus 1C (also referred to as an "apparatus" herein), which can be used to deliver liquid ventilation to the lungs of a mammal, such as a human patient. As with the embodiments of FIGS. 1A-B, the apparatus 1C can provide a heated and/or cooled liquid to the lungs. In some embodiments, the apparatus 1C can also provide gas ventilation to the lungs of a patient. For example, in some embodiments, the apparatus 1C provides cooled partial liquid ventilation (PLV) to the lungs. Features of the embodiment of FIG. 1C corresponding to those described with reference FIG. 1A or 1B are referenced by the same reference numerals but ending with no letters instead of "A" or "B". Accordingly, the apparatus of FIG. 1C can be similar to the apparatus 1A, 1B of FIGS. 1A and 1B except as described differently below. In certain arrangements, the features of the apparatus 1C can be incorporated into the apparatus 1A of FIG. 1A and the apparatus 1B of FIG. 1B and the features of the apparatus 1A of FIG. 1A and the apparatus 1B of FIG. 1B can be incorporated into the apparatus 1C. Therefore, any combination of features between those described in FIGS. 1A, 1B, and 1C are within the scope of the instant disclosure.

With continued reference to FIG. 1C, the apparatus 1C can include a delivery device, which in the illustrated embodiment can be an endotracheal tube 40 having a distal end 404 and a proximal end 406. As noted above, in certain embodiments, the delivery device can comprise other devices configured to aid in interfacing with a patient to deliver liquid and/or gas to a patient's lungs such as a mask and/or nasal cannula and/or device allowing for immersion of the patient in a breathing liquid. The distal end 404 of the endotracheal tube 40 connects to the airway of the patient 2 for delivering a mixture of the gas and/or the cooled liquid to the patient 2. The distal end 404B of the endotracheal tube 40B can include one or more openings to a lumen(s) in the wall of the endotracheal tube to be connected to a device or switch that measures or reacts to a human or animal patient's airway pressure $P_{aw}$ 44B while the apparatus 1B delivers liquid and/or gas ventilation to the lungs of the patient 2. For example, a pressure sensor 400 an be located near the proximal end 406B of the endotracheal tube 40 for detecting pressure $P_{aw}$ 440 in an airway of the patient 2. The pressure sensor 400 can be optionally operatively connected to a main sensor tube 2210, which can be in turn coupled to a control unit 186 located in a driver assembly 10, which will be described in detail below. In the illustrated embodiment, the pressure sensor 400 can be part of a pair of balloon cuffs circumferentially disposed on the proximal end 406 of the endotracheal tube 40. The volume, or pressure, inside a forward cuff is capable of responding to the change in $P_{aw}$ 440 even when a mixture of liquid and gas is delivered to the patient. In one embodiment, the endotracheal tube 40 may comprise a separate lumen for the balloon cuffs. In one embodiment, the endotracheal tube 40 may comprise a lumen in the wall of the tube, or a separate tube disposed distally to receive pressure/vacuum inside the patient's lungs, and disposed proximally or elsewhere for a pressure sensor(s). In one embodiment, the endotracheal tube 40 may comprise a sensor within to sense pressure/vacuum in the patient's lungs.

Figure 9:
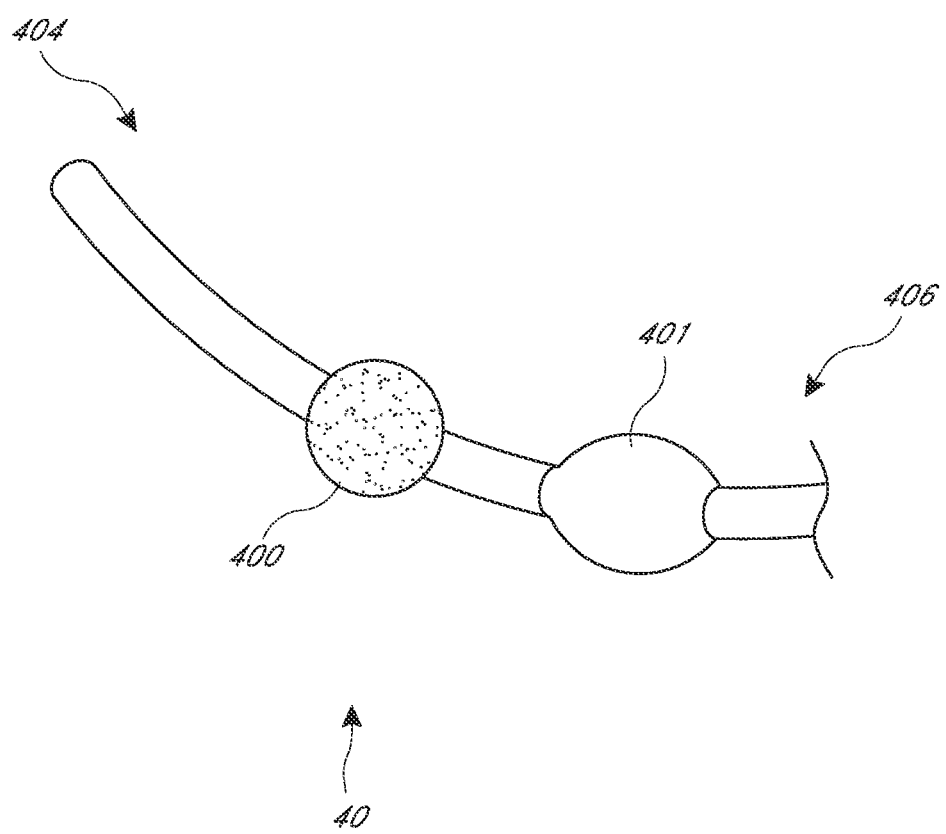
FIG. 9 illustrates an example embodiment of a distal end of an endotracheal tube in accordance with an embodiment of the present disclosure.

More specifically as shown in FIG. 9, in one embodiment, the cuff 401 of the endotracheal tube 40 can comprise an annular balloon like structure surrounding the distal end 404 of the endotracheal tube for the purpose of sealing against the inside of the trachea. An inflatable balloon device can advantageously supports passage through structures in the airway such as the vocal cords in a deflated state while providing a seal against leakage of ventilation fluids out of the airway, or unwanted fluids, solids, or secretions falling into the airway while inflated. While the illustrated cuff is preferred, in certain embodiments, cuffs and sealing structures of different configurations and structures can be used. In certain embodiments, commercially available endotracheal tubes with tapered cuffs, such as the cuff 401 shown in FIG. 9, can be adapted to be used with certain embodiments described herein. For example, a Sheridan Stat-Med tube or a Mallinckrodt™ EMT tube can be used. Also as shown in FIG. 9, a forward cuff 400 can include a pressure sensor capable of detecting pressure change in P$_{aw}$ 440. In some embodiments, the endotracheal tube 40 comprises a second in-wall lumen (not shown) open at the distal end of the tube and a luered or other port at the proximal end of the lumen parallel to a first, inflation lumen. The second lumen can extend between an inflation/deflation port and the cuff. The second lumen can be filled in and plugged distal to the cuff and can contain the pressure sensor. In some embodiments, the endotracheal tube 40 comprises multiple cuffs in tandem (not shown), with a distal seal for additional sealing if the proximal cuff is ruptured during procedures such as tonsillectomy or other in-trachea surgeries. In certain embodiments, the distal cuff is not required as a back-up seal in the trachea. The distal cuff can also be used to sense pressure in the patient's lungs. The distal cuff can also be subject to pressure in use. The pressure sensor 400 can be operatively connected to a main sensor tube (not illustrated), which is in turn can be coupled to a control unit 186 located contained in a driver assembly 10, which will be described in detail below.

The distal end 404B of the endotracheal tube 40B can include one or more openings to a lumen(s) in the wall of the endotracheal tube to be connected to a device or switch that measures or reacts to a human or animal patient's airway pressure P$_{aw}$ 44B while the apparatus 1B delivers liquid and/or gas ventilation to the lungs of the patient 2. FIG. 7B illustrates the endotracheal tube 40 in accordance with another embodiment of the present disclosure. In FIG. 7B, the endotracheal tube 40B can be constructed with a port 402 at or near the proximal end or as part of a connector attached at the proximal end for the purpose of observing pressure, adding medication, or withdrawing samples of fluid. The port may feature locking features, such as a luer or locking luer geometry.

Figure 6A:
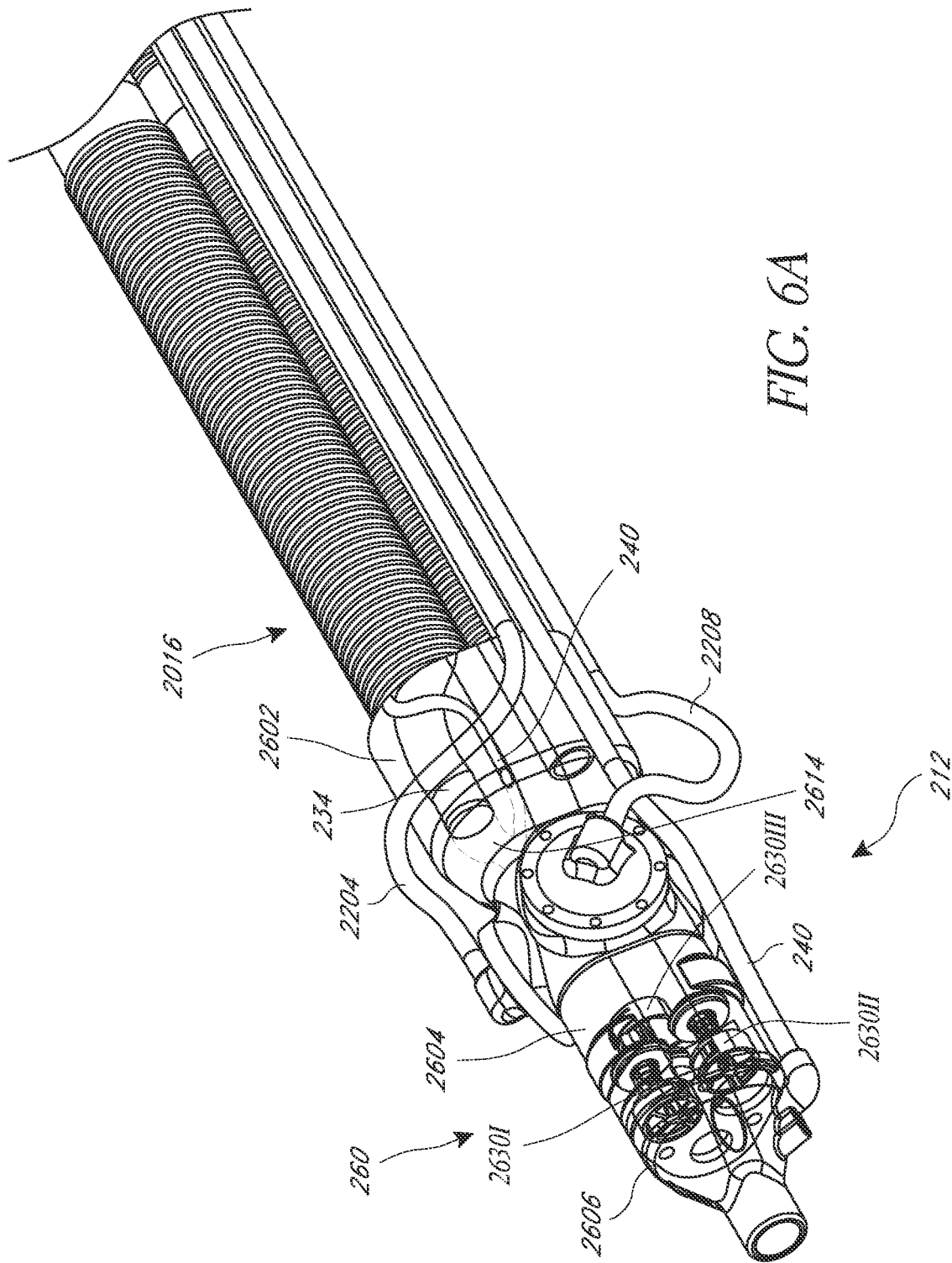
FIG. 6A is a perspective view of a distal end of the tube assembly in accordance with an example embodiment of the present disclosure.

With continued reference to FIGS. 1C and 7B, the proximal end 406 of the endotracheal tube can be connected to a distal nose portion 2606 of a distal flow connector 260 (shown in FIGS. 6B and 7B) directly or via any common commercially available airway connectors as desired. The distal flow connector 260 can have one or more channels for delivering and/or removing liquid or gas to and/or from the endotracheal tube 40 as well as features such as a pop-open device as an additional level of protection against patient over-pressure, or for access in an emergency situation requiring direct manual ventilation. In the illustrated embodiment as shown in FIGS. 6A and 7A, the distal flow connector 260 includes a liquid delivery channel 2608, a suction channel 2612, a gas delivery channel 2610 and a fluid recirculation channel 2614 as will be described below, the liquid and/or gas flowing through these channels can be controlled by one or more valves, which are placed in the channels.

Figure 7A:
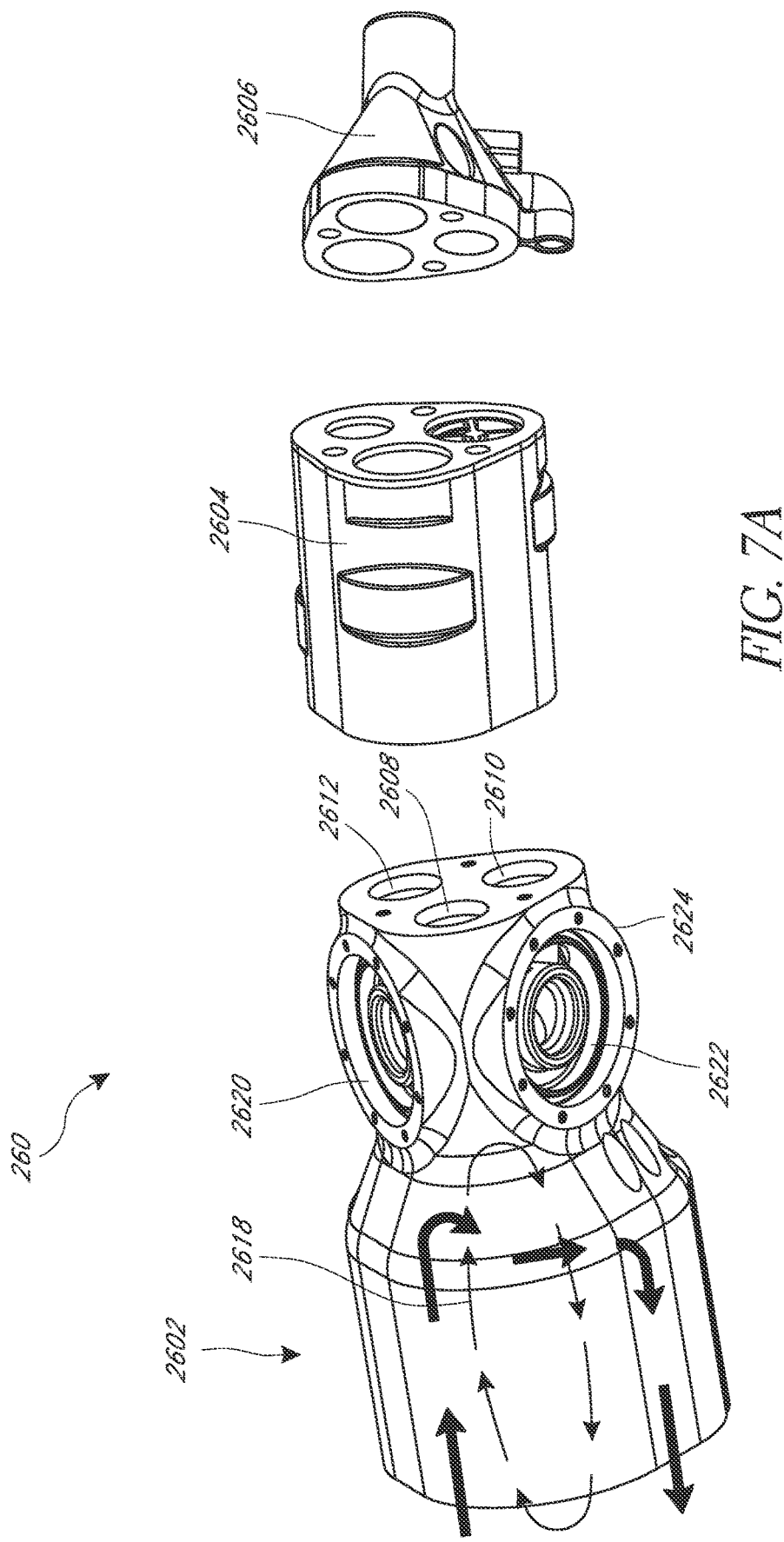
FIG. 7A illustrates an exploded view of a distal flow connector in accordance with an embodiment of the present disclosure.
Figure 7B:
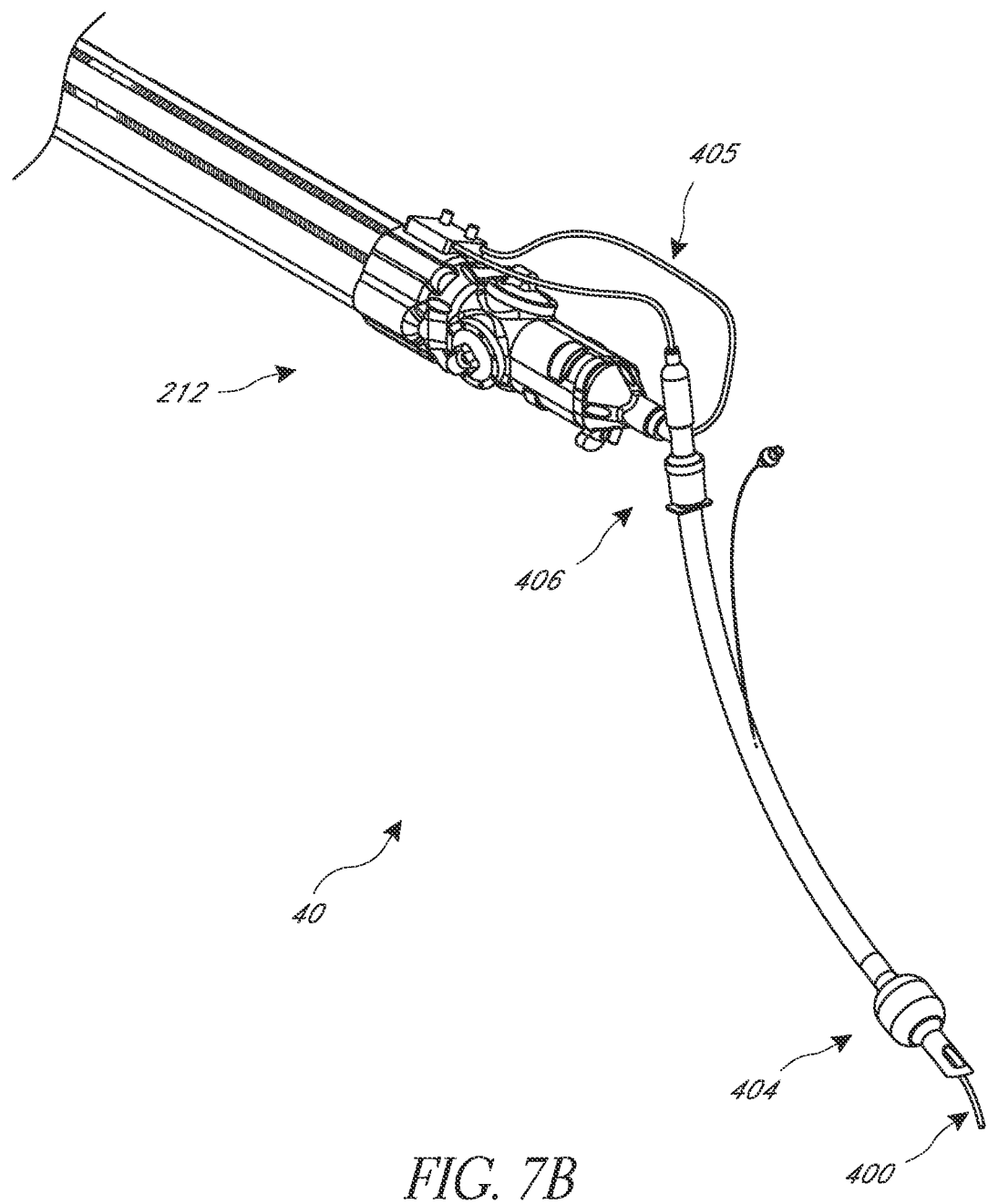
FIG. 7B illustrates a use of a distal flow connector with an endotracheal tube in accordance with an embodiment of the present disclosure.

FIG. 7A illustrates examples of components of the illustrated distal flow connector 260 in an exploded view. In the illustrated embodiment, the distal flow connector 260 can comprise a proximal portion 2602, a middle portion note, and the distal nose portion 2606. The distal nose portion 2606 of the distal flow connector can be suitable for connecting to the endotracheal tube 40, as shown in FIG. 7B. The proximal portion 2602 of the distal flow connector 260 can be an integral plastic part comprising the four channels plus co-axial cooling water flow in accordance with an embodiment of the present disclosure in order to make the distal flow connector more compact and easier to use. It is contemplated that the proximal portion 2602 can be 3D printed, which can be cheaper and faster than conventional machining or molding, and also can allow for easy update of design or adding customized configurations on a CAD model. Furthermore, machining and molding may not be feasible due to the complex structure of the proximal portion 2602 and the resistance to flow that would arise from features so configured as to be producible through means other than 3D printing. The middle portion 2604 of the distal flow connector can house a plurality of one-way check valves 2630I, 2630II, 2630III, also shown in the block diagram in FIG. 1D. The check valves act as additional safety features to ensure that the directions of flow in the distal flow connector 260 are as intended. As described earlier, the check valves can also provide for an automatic shutoff of gas by higher pressure liquid delivery, which can be timed as required to produce the desired mix of gas to liquid by a delay of delivery of the liquid to the proximal portion 2602. The proximal portion 2602 can also comprise a suction valve 2620, a gas delivery valve 2622, and a liquid delivery valve 2624.

In an exemplary embodiment, the gas delivery valve 2622 is located in the gas delivery channel 2610 and connects to a gas delivery pilot tube 2204. The liquid delivery valve 2624 is located in the liquid delivery channel 2608 and connects to a liquid delivery pilot tube 2206. The suction valve 2620 is located in the suction channel 2612 and connects to a suction pilot tube 2202. The distal flow connector 260 can additionally comprise the liquid recirculation (No. 8) valve 238 (not shown in FIG. 7A but shown in FIG. 5B) in the liquid recirculation channel 2614 and connects to a liquid recirculation pilot tube 2208. The suction, gas delivery, liquid delivery and recirculation pilot tubes, 2202, 2204, 2206, 2208, and the main sensor tube 2210 all extend along a tube assembly 20 from a distal end 212 to a proximal end 210. In modified embodiments, the liquid recirculation valve 238 can be located at other locations. For example, the liquid recirculation (No. 8) valve 238 can be located between the liquid recirculation port 130 and the liquid recirculation tube 240. In some embodiments, the valves 2620, 2622, 2624 can be two-way exhalation valves. In the illustrated embodiment, each of the valves 2620, 2622, 2624 on the proximal portion 2602 can comprise a diaphragm 2626 and a cap 2828. The diaphragm 2626 is designed to "oil can" to enhance flow.

With continued reference to FIG. 1C, the distal flow connector 260 can be connected to the distal end 212 of the tube assembly 20. In one embodiment, the tube assembly 20 includes one or more tubes that correspond to the channels in the distal flow connector 260. In the illustrated embodiment, the tube assembly 20 is generally flexible and can have a length of about 6 feet. In one arrangement as shown in FIGS. 4A-6A, the tube assembly 20 includes a suction tube 230 that can be in fluid communication with the suction channel 2612 of the distal flow connector. The tube assembly 20 can also include a gas delivery tube 232 that can be in fluid communication with the gas delivery channel 2610 of the distal flow connector 260. The tube assembly 20 can also include a liquid delivery tube 234 that can be in fluid communication with the liquid delivery channel 2608 of the distal flow connector. The tube assembly can also include a liquid recirculation tube 240 in fluid communication with the liquid recirculation channel 2614 of the distal flow connector.

As shown in FIG. 1C, the tube assembly 20 can include a heat exchange assembly 200 (more clearly shown in FIGS. 1D and 5A) on a distal portion of the tube assembly 20. The heat exchange assembly 200 can comprise an outer tube 2006, a proximal flow connector 250, at least a portion of the liquid delivery tube 234, and at least a portion of the liquid recirculation tube 240. The outer tube 2006 can provide heat insulation (and containment) to the cold water 302, the liquid delivery tube 234, and the liquid recirculation tube 240 inside the outer tube 2006. As shown in FIG. 6A, a distal end 2016 of the heat exchange assembly 200 can fit into the proximal portion 2602 of the distal flow connector 260. A cold water inlet pipe 242 is connected to the proximal portion 2602 of the distal flow connector 260 such that the cold water 302 enters the heat exchange assembly 200 at its distal end 2016. As shown in FIG. 6B, the cold water 302 can flow in the direction 2616. The direction 2616 allows better cooling efficiency. One of ordinary skill in the art may appreciate that the water can also flow in an opposite direction. The cold water 302 cools the liquid in both the liquid delivery tube 234 and the liquid recirculation tube 240 as the cold water 302 flows from the distal end 2016 towards a proximal end 2014 of the heat exchange assembly to return to a cold water bath 300. Furthermore, the liquid delivery tube 234 and the liquid recirculation tube 240 can be twisted into a double helix 2012 inside the outer tube 2006 in accordance with one embodiment of the present disclosure. In some embodiments, the liquid delivery tube 234 and the liquid recirculation tube 240 are also corrugated. As shown in FIGS. 1C and 7B, temperature probe 405 can be connected at the proximal end of the endotracheal tube 40 for readout on a thermometer display or recording device of the measured temperature of the fluids entering and exiting the lungs.

In addition to the advantages described above for providing heat exchange at the tube assembly, another advantage of the heat exchange assembly in accordance with the illustrated embodiment is to maximize and/or increase heat exchange and the resulting cooling and/or heating. Specifically, the illustrated double helix configuration and/or using corrugated tubes can provide more surface area and/or turbulence and thus additional cooling time for the liquid without making the tube assembly excessively long and cumbersome to use. Furthermore, having the liquid recirculation tube 240 as part of the heat exchange assembly 200 can allow additional cooling of the liquid when it is being circulated in a closed loop formed by the liquid delivery tube 234, the liquid recirculation tube 240, and a canister 160 (or fluid reservoir) comprising a reservoir of the liquid located in a driver assembly 10. In certain embodiments, the liquid delivery tube 234 and/or the liquid recirculation tube 240 at a proximal end 210 of the tube assembly (shown in FIG. 4B), that is, before they become part of the heat exchange assembly 200, can be wrapped with an insulating material 270 to help the liquid stay cooled for a longer period of time.

Figure 4A:
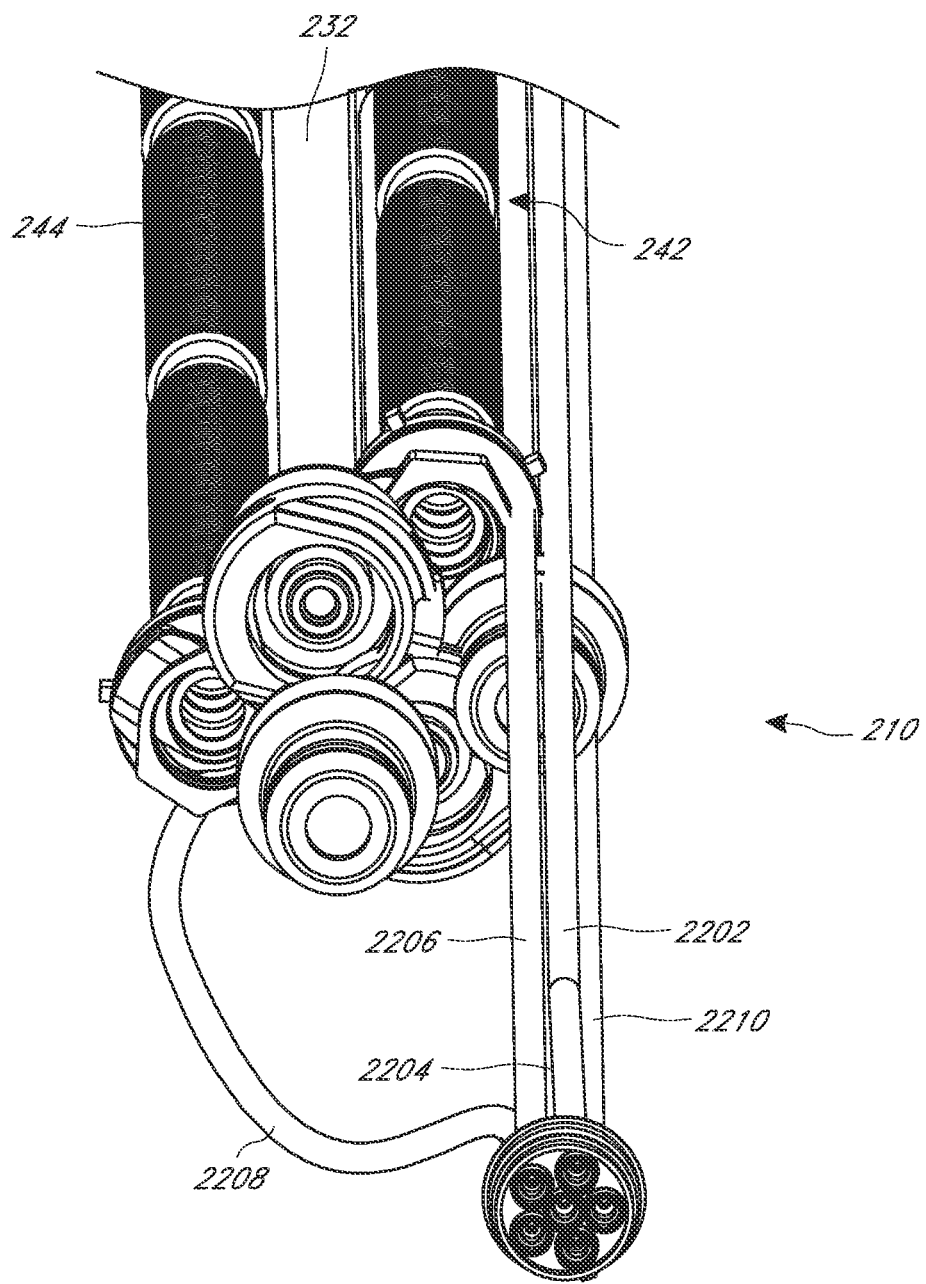
FIG. 4A illustrates a top perspective view of a proximal end of the tube assembly in accordance with an embodiment of the present disclosure.
Figure 5A:
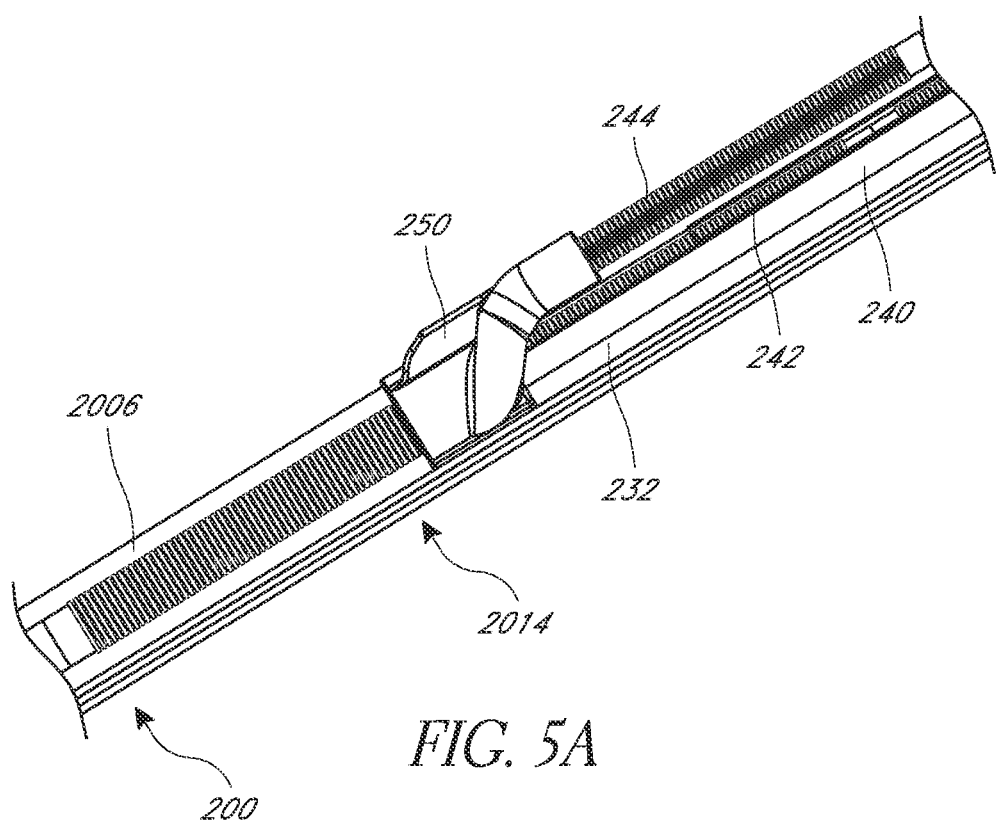
FIG. 5A is a perspective view of a proximal end of a heat exchange assembly of the tube assembly in accordance with an example embodiment of the present disclosure.

FIG. 5A illustrates the proximal end 2014 of the heat exchange assembly 200. The proximal flow connector 250 of the heat exchange assembly 200 can connect to a cold water outlet pipe 244. The cold water inlet pipe 242 and a cold water outlet pipe 244 (shown in FIG. 4A) can be connected to a cold water bath assembly 30 for cooling the liquid 50 and/or the gas. The cold water bath assembly 30 can have a cold water bath 300 containing cold water 302, a water bath outflow tube 304 connected to the tube assembly 20 at the cold water inlet pipe 242, and a water bath inflow tube 306 connected to the tube assembly 20 at the cold water outlet pipe 244, shown in FIG. 1C. In an embodiment as shown in FIGS. 1C-1D, the water bath inflow tube 306, which is in fluid communication with the cold water outlet pipe 244, connects to a lid of the cold water bath 300. The water bath outflow tube 304, which is in fluid communication with the cold water inlet pipe 242, connects to a turbine 310 that can drive the cold water 302 from the cold water bath 300. During operation of the apparatus 1C, cold water 302 flows in a loop from the cold water bath 300 through the cold water inlet pipe 242 and the cold water outlet pipe 244 and back to the cold water bath 300. The cold water bath 300 may contain ice or other materials suitable for cooling the water that is known or obvious to a person of ordinary skill in the art. Instead of having a cold water bath built into a driver assembly for heat exchange, the apparatus 1C reduces an overall size and weight of the driver assembly 10 by having a stand-alone cold water bath, which can be obtained separately at a patient site instead of having to be transported to the patient site as part of the apparatus. In another arrangement, a common ice cooler can be used as the transportation case for the driver and double as the cold water bath. The ice cooler can be a common ice chest of flyable luggage size so that the apparatus 1C can advantageously be transported on a commercial air craft.

Figure 5B:
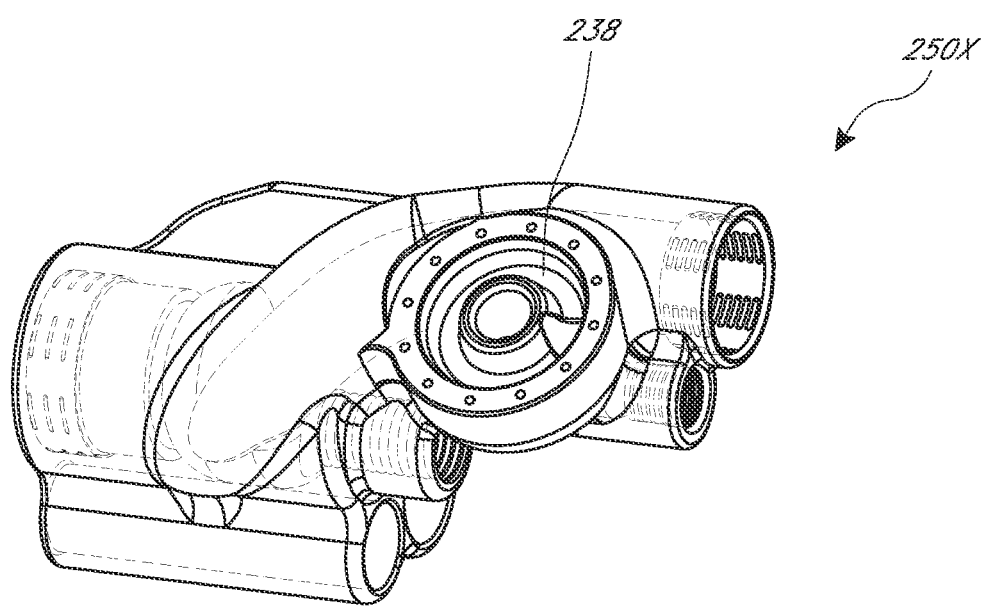
FIG. 5B illustrates a perspective view of a proximal flow connector in accordance with another example embodiment of the present disclosure.

FIG. 5B provides another embodiment of a proximal flow connector 250X having features similar to those of the proximal flow connector 250. The proximal flow connector 250X additionally comprises the liquid recirculation valve 238. Having the liquid recirculation valve 238 on the proximal flow connector 250X advantageously reduces the overall size of the tube assembly 20. As described above, updating the design of the proximal flow connector to incorporate the liquid recirculation valve 238 can be done efficiently on a 3D CAD model.

Figure 4B:
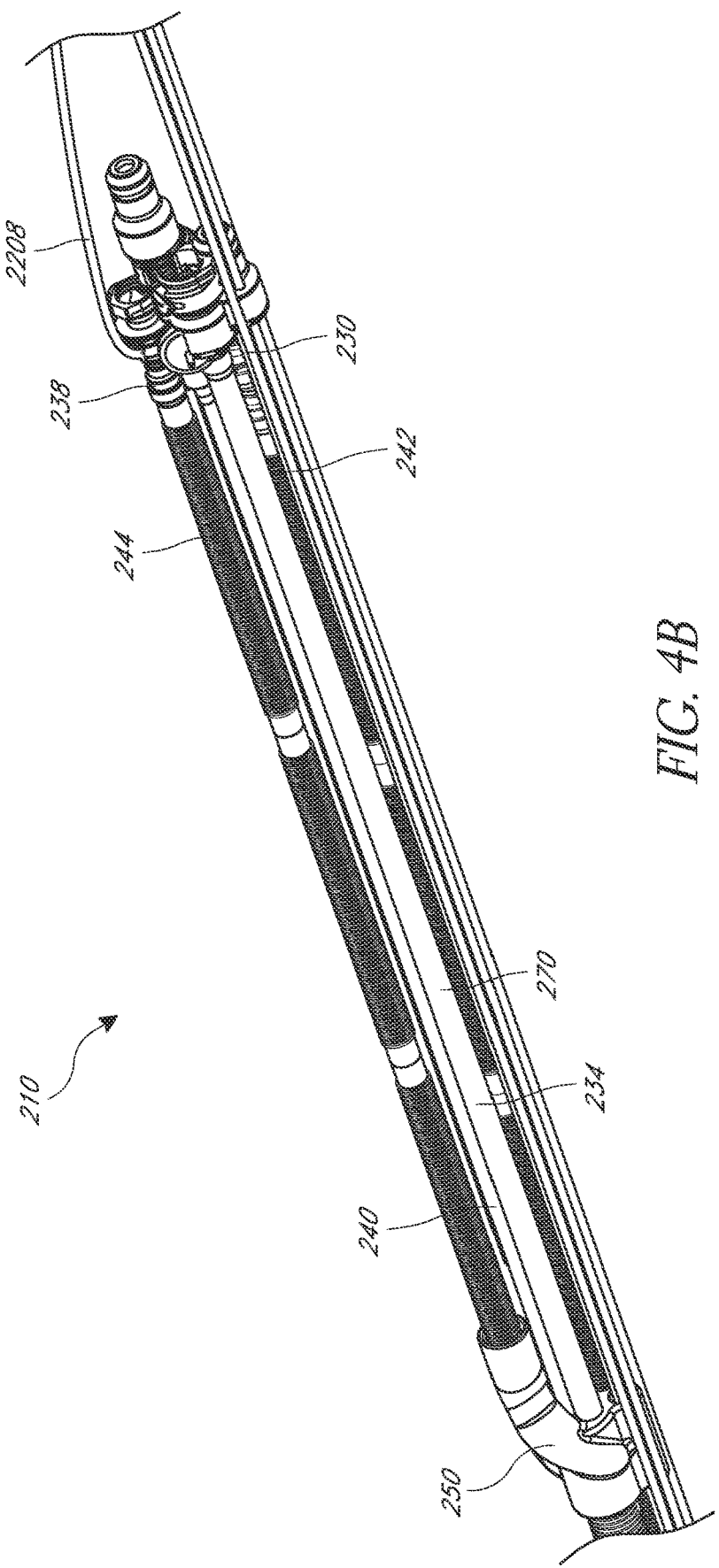
FIG. 4B illustrates a side perspective view of the proximal end of the tube assembly in FIG. 4A.
Figure 4C:
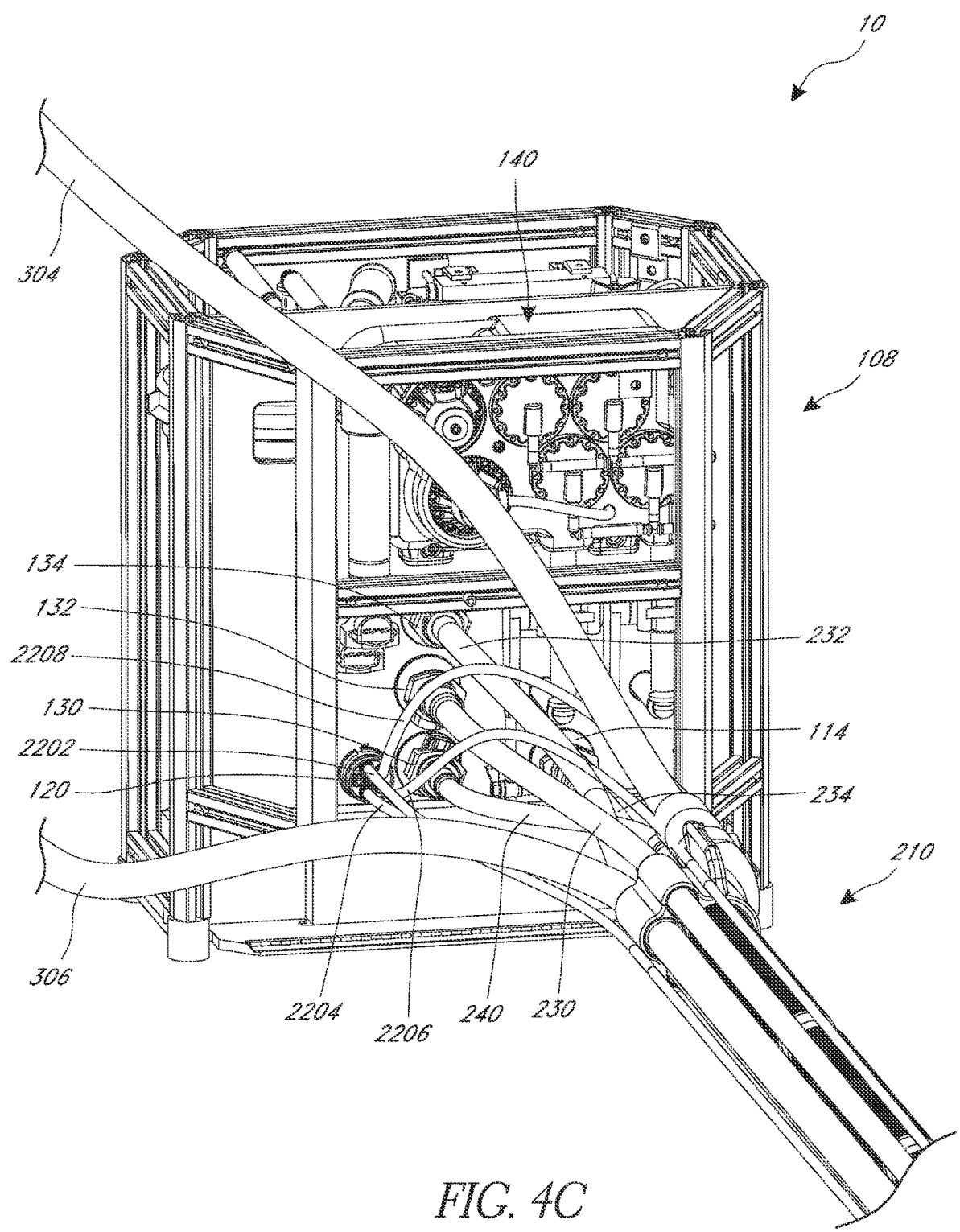
FIG. 4C illustrate a perspective view of the proximal end of the tube assembly in FIG. 4A connected to the driver assembly in FIG. 2A.

Turning to a proximal end 210 of the tube assembly 20 as illustrated in FIG. 4A and FIG. 4B, the proximal end 210 of the tube assembly connects to the driver assembly 10 through an opening 110 of the driver assembly. FIG. 4C illustrate how the proximal end 210 of the tube assembly connects to the driver assembly 10. As shown in FIG. 4C, the liquid delivery tube 234 is in fluid communication with a liquid-delivery port 114 (also shown in FIG. 2C) on the driver assembly 10, the suction tube 230 is in fluid communication with a suction port 132 (also shown in FIG. 2C) on the driver assembly 10, the gas delivery tube 232 is in fluid communication with an gas delivery port 134 (also shown in FIG. 2C) on the driver assembly 10, and the liquid recirculation tube 240 is in fluid communication with a liquid recirculation port 130 (also shown in FIG. 2C) on the driver assembly 10. The proximal end 210 of the tube assembly 20 can further comprise a plurality of pilot tubes configured to be connected to a circuit connection port 120 (also shown in FIG. 2C) on the driver assembly 10. The plurality of pilot tubes can include the suction pilot tube 2202, the gas delivery pilot tube 2204, the liquid delivery pilot tube 2206, the liquid recirculation pilot tube 2208, and the main sensor tube 2210 in one connector to facilitate connection of the control tubes to their respective pilot lines ending at a circuit connection port 120 on the driver assembly 10. The circuit connection port 120 may be eliminated in select embodiments for reduced cost and weight and replaced with a quick disconnect (QD) fitting.

Figure 2A:
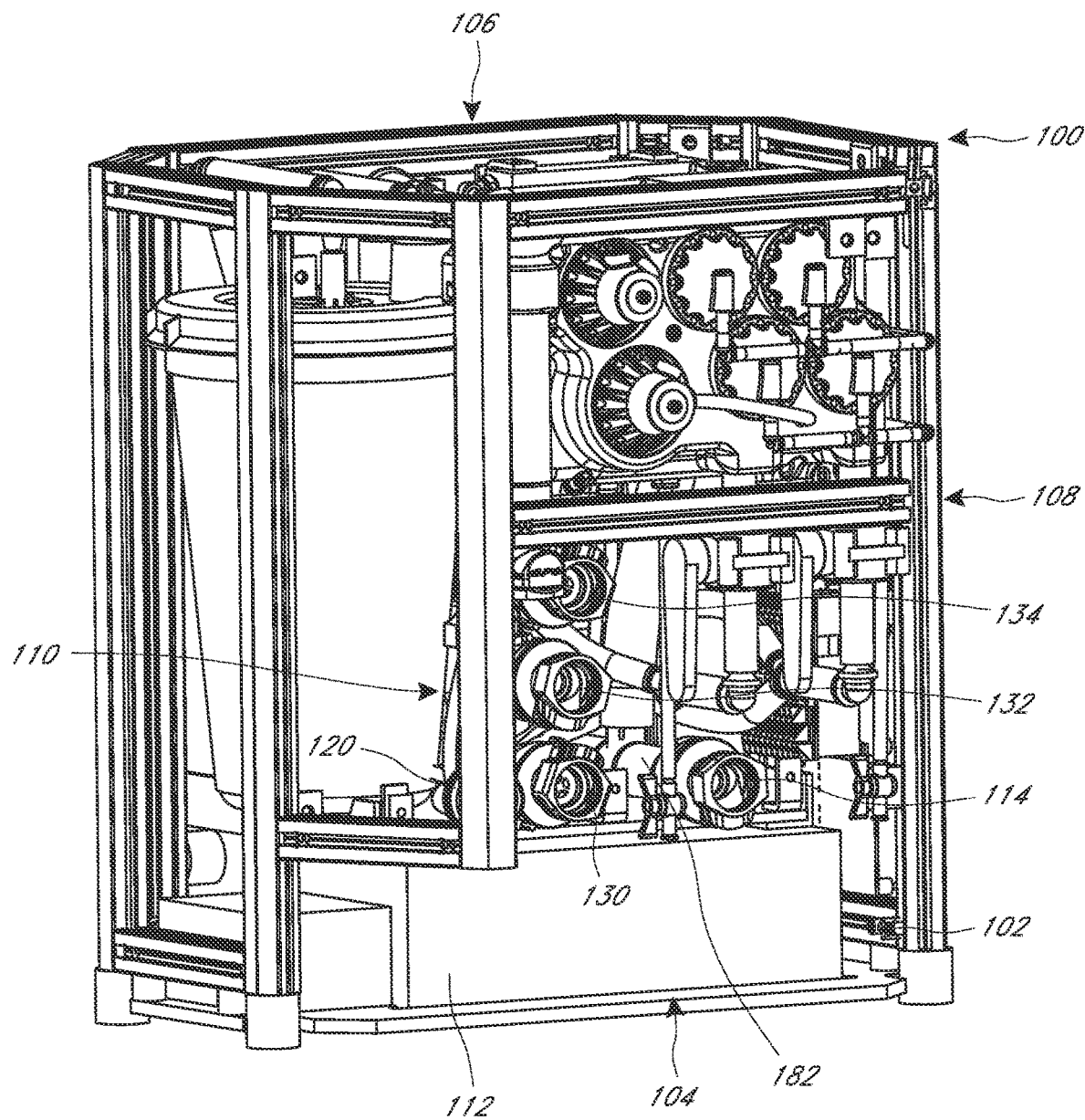
FIG. 2A illustrates a front perspective view of an example embodiment of a driver assembly in FIGS. 1C-1D.

Turning to an example embodiment of the driver assembly 10 as shown in FIG. 2A, the driver assembly 10 can be encased in an octagonal-shaped protective see-through cage-like frame 108. The ability to see through the frame 108 can advantageously provide visual confirmation that the apparatus 1C is running as intended or that the apparatus 1C is malfunctioning. The ability to see through the frame in some embodiments, the octagonal shape of the frame 108 fits into a flyable-sized off-the-shelf cooler. The driver assembly 10 has a front side 104 and a back side 106. The driver assembly 10 also has an upper side 100 and a lower side 102. The cage-like frame 108 has the opening 110 located on the front side 104 of the driver assembly towards the lower side 102 of the driver assembly, leaving exposed on the front side 104 a power source 112 located at the lower side 102 of the driver assembly, the liquid delivery port 114, the circuit connection port 120, the liquid recirculation port 130, the suction port 132, and the gas delivery port 134. It is contemplated that the apparatus 1C can be operated by both a DC power source, such as batteries and back up batteries using a back-up battery switch, and an AC power source, such as by plugging into a power socket, in accordance with an embodiment of the present disclosure. Dual power source allow the apparatus to be used for potentially unlimited amount of time when there is a power socket near the patient and for when there is a power outage or no AC power outlet. In certain arrangements, at least one hour of continuous operation is possible on battery power and an additional hour on back up battery power. In certain arrangements, batteries can be hot swap removed and charged using a quick charge method in one hour and can be hot swapped back into the machine without interruption to the ventilation procedure if an AC power outlet is not in close proximity to the ventilator or during transport.

Figure 2B:
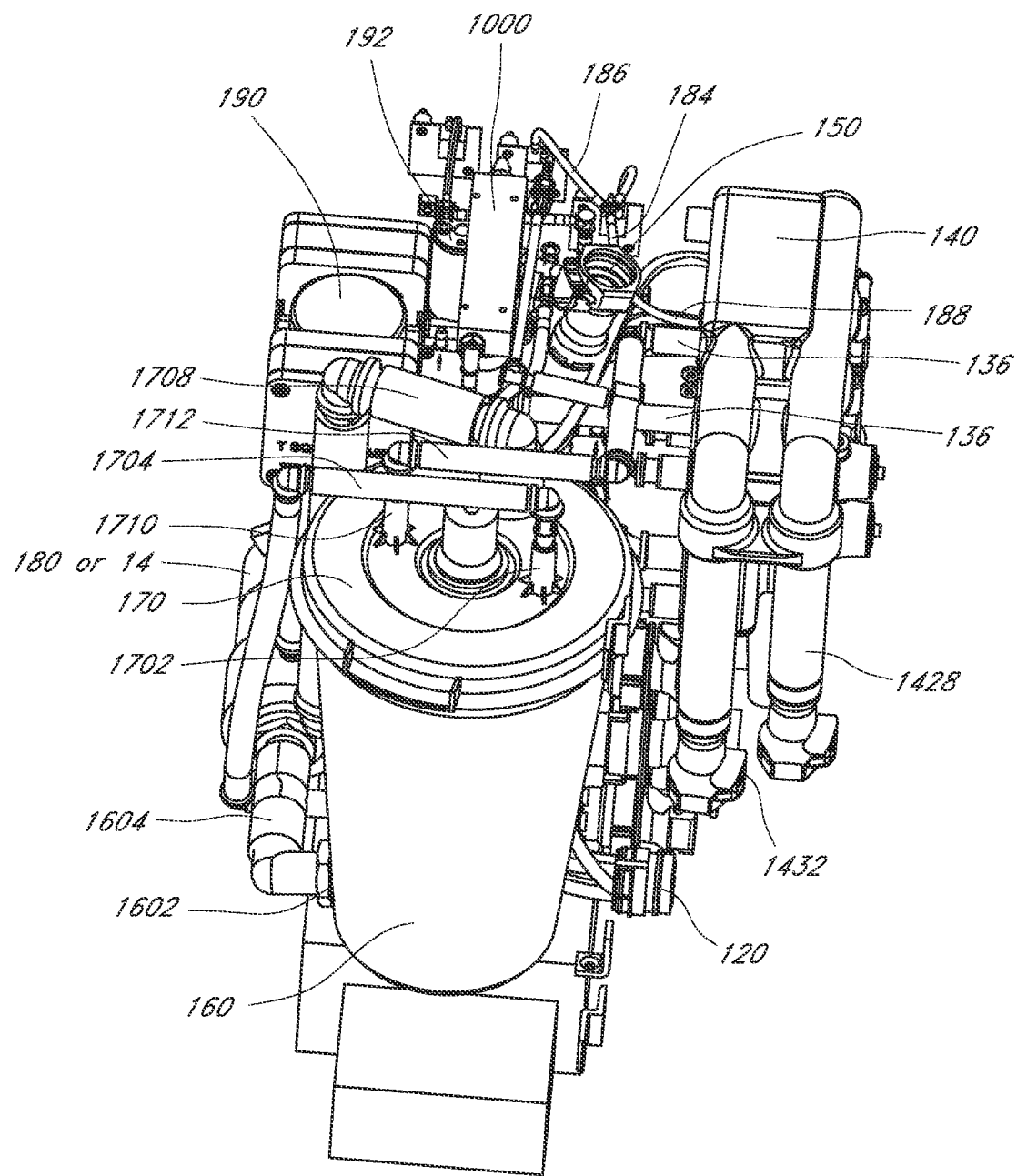
FIG. 2B illustrates a top perspective view of the driver assembly in FIGS. 1C and 1D without a protective frame.
Figure 2C:
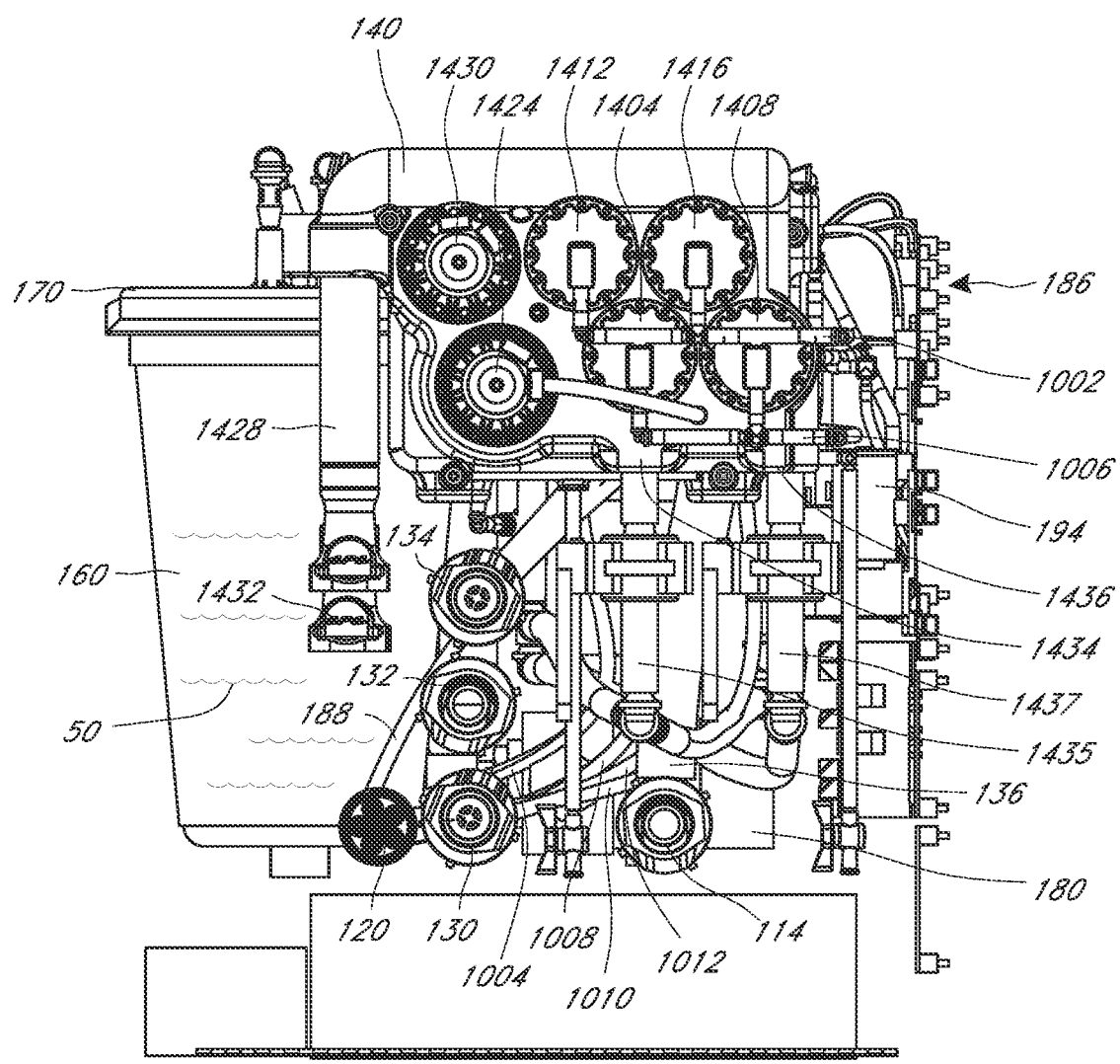
FIG. 2C illustrates a front view of the driver assembly in FIGS. 1C and 1D without the protective frame.

With continued reference to FIGS. 2C and 4C, the main sensor tube 2210 can be operatively coupled to the control unit 186 located within the driver assembly 10 via the circuit connection port 120. The control unit 186 can comprise a state controller and a plurality of boards with pressure/vacuum sensing chips mounted on them. The control unit 186 can be configured to decide whether the apparatus should be in the inhale phase or the exhale phase according to information from the pressure sensor 400 via the main sensor tube 2210. The apparatus 1C can be configured to avoid response lags, inaccuracies in pressure sending due to elevation changes of the driver assembly relative to the patient when there is a liquid column in the main sensor tube 2210. One of ordinary skill in the art may appreciate that other forms of communication between the pressure sensor 400 and the control unit 186 can be used. The control unit 186 outputs instructions to control the flow of the liquid and gas between the tube assembly 20 and the endotracheal tube 40 by controlling opening and closing of the one or more two-way valves 2620, 2622, 2624, 238 described above and shown in FIGS. 5B and 7A. In the illustrated embodiment, opening and closing the valves 2620, 2622, 2624, 238 can be done by smaller pilot valves 1018, 1020, 1022, 1024 (shown in FIG. 1D) and/or three way solenoid valves (also controlled by the control unit 186 and described below; shown in FIG. 10B) located in the driver assembly 10. The pilot valves and solenoid can be four pairs of 2-way valves. The pilot valves can also be four 3-way valves.

In an exemplary embodiment, valves described herein may include a diaphragm. FIG. 12 illustrates an exemplary contoured diaphragm to create a sealing surface for the valve. As shown, the valve is normally open, and closes with the application of pressure. However, the valve may be normally closed. The valve may also be opened with pressure and/or opened or closed with a vacuum. As shown, having a normally open valve that closes with a change in pressure permits one of the pressure sources to be removed from the system. For instance, the vacuum pump may be removed, and a single pump used to control the valves. In this case, the valve may be controlled by applying a greater than atmospheric pressure to close the valve, and applying atmospheric pressure or simply opening the line to atmosphere to open the valve. As illustrated in the cross section of FIG. 12A, the valve includes a diaphragm in a normally open configuration that permits to and from flow between a first opening and a second opening. As shown, the first and second openings are in a common plane and positioned on the same side of the diaphragm. The valve diaphragm in a relaxed or normal configuration is in contact with the plane containing the first and second opening at an outer perimeter of the diaphragm and out of contact with the plane on an interior region of the diaphragm. For example, the diaphragm may be curved or dome shaped. The valve may include a control opening on an opposite side of the diaphragm from the first and second opening. The control opening configured to supply pressure or vacuum or remove pressure or vacuum to control the position of the diagraph, such as in either a closed or open configuration.

When the pressure in the airway $P_{aw}$ 440 is below a predetermined maximum threshold pressure, the apparatus 1C can operate in the inhale phase to deliver the gas and/or the cooled liquid 50 to the lungs of the patient 2 with the gas delivery (No. 5) valve 2622 and/or the liquid delivery (No. 6) valve 2624 open and the suction (No. 10) valve 2620 and the recirculation (No. 8) valve 238 closed. In certain example embodiments, in the threshold pressure can be approximately 30 cm water (cm $H_2O$). In certain embodiments, the threshold pressure can be greater than or less than approximately 30 cm water (cm $H_2O$). For example, as described below, in certain embodiments a band around the chest can be used in combination with an embodiment of the apparatus described herein. In such embodiments, it is anticipated that a higher threshold pressure can be used. Once the pressure sensor 400 detects the predetermined maximum threshold pressure, the apparatus 1C switches to the exhale phase to withdraw the gas and the liquid 50 from lungs of the patient 2 via the endotracheal tube 40 with the suction valve 2620 open and the gas delivery valve 2622 and the liquid delivery valve 2624 closed until some preset vacuum, or minimum threshold pressure, is reached. In certain example embodiments, in the preset vacuum can be approximately negative 30 cm water (cm $H_2O$). In certain embodiments, the threshold pressure can be greater than or less than approximately negative 30 cm water (cm $H_2O$). The recirculation valve 238 is also open during the exhale phase to allow the liquid 50 to flow in the closed loop 2618 as shown in FIG. 6B and back to the canister 160. The preset vacuum causes the apparatus 1C to switch back to the inhale phase. As described above, the predetermined threshold pressure can be achieved in a variety of circumstances.

In some embodiments, the device can be equipped with an optional second control 187 (shown in FIG. 1D) configured for use with CPR by syncing the second control 187 with the manual or automated CPR. The second control 187 can be a small bag such as a blood pressure cuff that is pressurized by a band or piston of the automated CPR or goes between hands of a human CPR provider and the patient's chest. In certain embodiments, the second control 187 can be a tension sensor in a band type and/or automated CPR device (such as Zoll AutoPulse®), or driven by the pressure of a piston-cylinder arrangement (such as Michigan Instruments "Thumper") or other pneumatic, force, or pressure sensing means of determining synchronization with an automated or manual CPR procedure. The predetermined threshold pressure and/or the preset vacuum can be adjusted and/or set by the user of the apparatus.

The liquid delivery tube 234 of the tube assembly can be operatively coupled to a canister 160 (shown in FIGS. 2A-2D) located within the driver assembly 10 which can comprise a reservoir of liquid and/or a pump for delivering the fluid from the canister 160 to the liquid delivery tube 243. In a similar manner, the suction tube 230 and the liquid recirculation tube 240 of the tube assembly can be operatively coupled to the canister 160. As shown in FIG. 2B, the canister 160 is air-sealed with a canister lid 170. The canister 160 can be located behind and to the left of the circuit manifold 140. The canister 160 can be located at other locations on other embodiments. The canister 160 contains the liquid 50 and has a liquid delivery opening 1602 near a bottom of the canister 160. The liquid delivery opening 1602 is in fluid communication with a turbine pump 180 (shown in FIG. 2C) via a turbine pump connecting tube 1604, and the turbine pump 180 in turn connects to one end of a liquid delivery pipe 182. An opposite end of the liquid delivery pipe 182 terminates at the liquid delivery port 114 for connecting with the fluid delivery tube 234. When the apparatus 1C is in an inhale phase, the liquid 50 can leave the canister 160 under a pressure (discussed below) to be delivered to the patient 2. Similar to the turbine pump 18 in FIG. 1B, the turbine pump 180 can pump the liquid 50 from the canister 160 to the liquid delivery pipe 182 and eventually to the heat exchange assembly 200 faster and could aerate the fluid 50 as it goes through the turbine. Additional liquid may be added through a refill port 150 which is also coupled to the turbine pump 180.

The canister lid 170 can also have a liquid recirculation opening 1702, a suction opening 1706, and a pressure control opening 1710. The liquid recirculation opening 1702 is in fluid communication with a liquid recirculation return tube 1704, which in turn connects to the liquid recirculation port 130 for connecting to the liquid recirculation tube 240. The suction opening 1706 is in fluid communication with a canister suction tube 1708, which in turn connects to the suction port 132 for connecting with the suction tube 230. The pressure control opening 1710 connects to the canister pressure control tube 1712. When the apparatus 1C is in an exhale phase, the fluid 50 in the liquid recirculation return tube 1704 and a mixture of the gas and the fluid 50 withdrawn from the lungs of the patient 2 are returned to the canister 160. An advantage of returning the gas withdrawn from the patient into the sealed canister is to control exhaled air being released into the room and capture exhaled air which is toxic, flammable (such as anesthetics), or contains infectious bacteria or viruses. Keeping the exhaled air contained protects medical personnel or first aid providers when rescuing biological or chemical event victims using a fluid for lung lavage. Liquid samples may also be saved in the canister 160 for analysis. Air samples can be taken from element 1428.

Turning to FIG. 2B, which illustrates the driver assembly 10 in FIG. 2A without the protective frame 108, the driver assembly 10 further comprises a pressure/vacuum circuit manifold 140. The pressure/vacuum circuit manifold 140 can be located toward the front side 104 of the driver assembly. One of ordinary skill in the art may appreciate that the manifold 140 can be placed at other locations. The pressure/vacuum circuit manifold 140 can be an integral circuit that houses a plurality of valves, shown in greater detail in FIG. 3B. An embodiment of the present disclosure having the one-part circuit manifold 140 has the advantage of providing efficient flow paths and reducing the size of the driver assembly, making the apparatus more portable. It is contemplated that the one-part circuit manifold 140 can be 3D printed to save cost and time for making the manifold. The printed flow paths in a 3D printed manifold can be readily optimized for flow characteristics. With 3D modeling, it will also be easy to change and update designs of the manifold, or make customized configurations thereof. Conventional machining and molding may not even be feasible due to the complex flow paths of the manifold 140 and would result in less optimal flow.

Figure 3A:
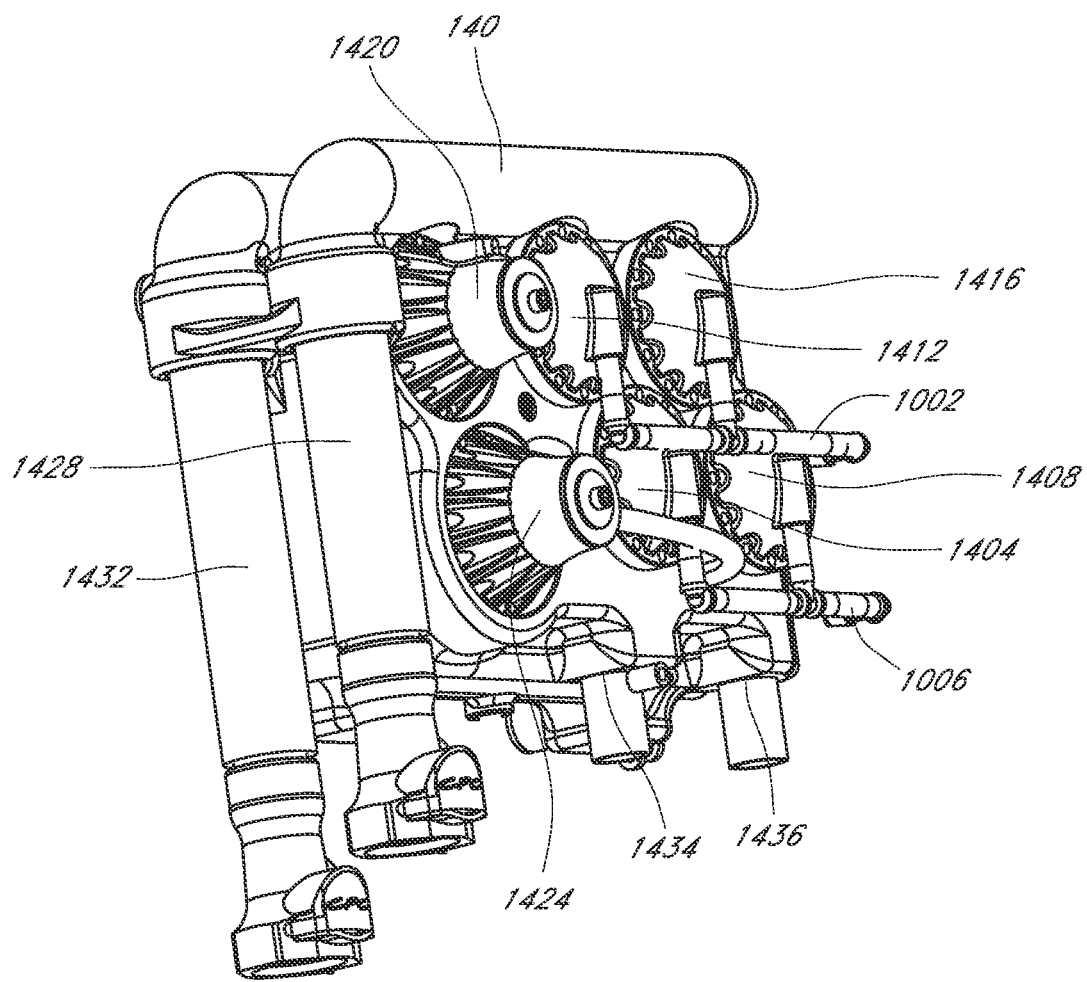
FIG. 3A illustrates an isolated perspective view of a circuit manifold with connecting parts in accordance with an example embodiment of the present disclosure.
Figure 3B:
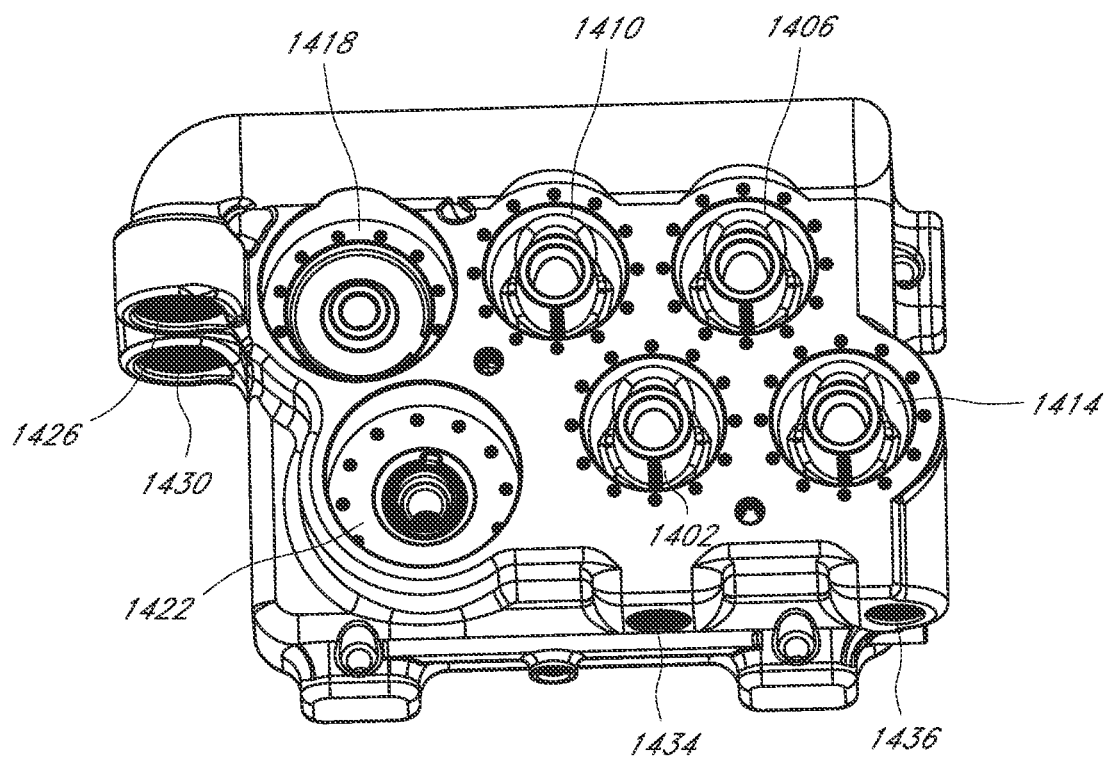
FIG. 3B illustrates a front perspective view of the circuit manifold in FIG. 3A.

An isolated perspective view of the manifold 140 with its connecting parts are shown in FIG. 3A. The manifold 140 can comprise a manifold air inlet 1426 connected to a manifold air inlet tube 1428 and a manifold air outlet 1430 connected to a manifold air outlet tube 1432. The manifold air inlet tube 1428 provides convenient connection and disconnection to any prescribed gas, such as oxygen or an anesthetic gas depending on the needs of the patient 2. The manifold air outlet tube 1432 provides quick connection and disconnection of device for containing the exhaled gasses as may be required for diagnosis or user safety.

As shown in the block diagram illustrating operations of the apparatus 1C in FIG. 1D, the manifold 140 can control gas inflow from the manifold air inlet 1426 to a breathing tube 136, which is in fluid communication with the gas delivery port 134 and the gas delivery tube 232 to delivery gas to the patient 2. In addition, the circuit manifold 140 can connect to the canister pressure control tube 1712 to provide negative or positive pressure in the canister 160 so that the liquid 50 and gas withdrawn from the patient 2 can reenter the air-sealed canister 160 or to assistant in its delivery to the patient.

Figure 3C:
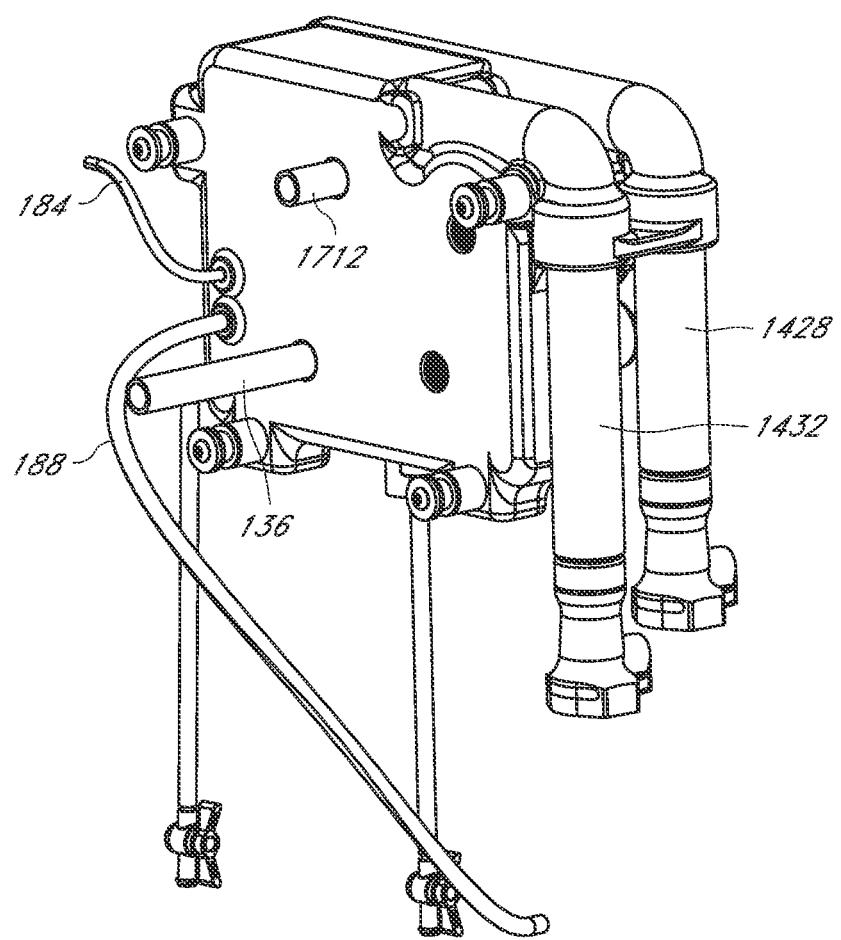
FIG. 3C illustrates back perspective view of the circuit manifold in and its connecting parts FIGS. 3A-3B.

FIG. 3C also shows that the circuit manifold 140 can connect to a sensor drain and a breather drain to remove the fluid that builds up in the manifold 140. These drains prevent sensors and the diaphragm pump 190 from contacting water and the breathing liquid, such as PFC. Also as shown in FIG. 2B, an incoming line 188 and an outgoing line 184 join pneumatically in a chamber inside the manifold 140. The lines 188, 184 also serve as a liquid trap to protect pressure/vacuum sensors in the apparatus 1C. Liquid can also be trapped in an additional volume above the liquid in the canister 160 and be removed through a canister pressure control tube 1712 during the exhale phase.

Turning to the valves on the manifold 140, the manifold 140 can house four piloted pneumatic valves, a No. 9 valve 1402, a No. 15 valve 1406, a No. 16 valve 1410, a No. 17 valve 1414. The manifold 140 can also house a pressure relief valve 1418, and a vacuum relief valve 1422 (shown in FIG. 3B). The No. 17 valve 1414 is covered by a first valve cap 1416. The No. 15 valve 1406 is covered by a second valve cap 1408. The No. 9 valve 1402 is covered by a third valve cap 1404. The No. 16 valve 1410 is covered by a fourth valve cap 1412. The pressure relief valve 1418 is covered by a pressure relief cap 1420 and the vacuum relief valve 1422 is covered by a vacuum relief cap 1424. As described above, these relief valves are optional and protect safety of the patient when abnormal $P_{aw}$ 440 is detected or when the apparatus malfunctions. The relief valves can also serve the function of enhancing reliability and portability of the device by eliminating or reducing the need for sensors or controls on a main diaphragm pump 190, which is described below. As described above, any of the relief values may be removed and over or under pressure handled with controls of the respective pump directly.

Figure 3D:
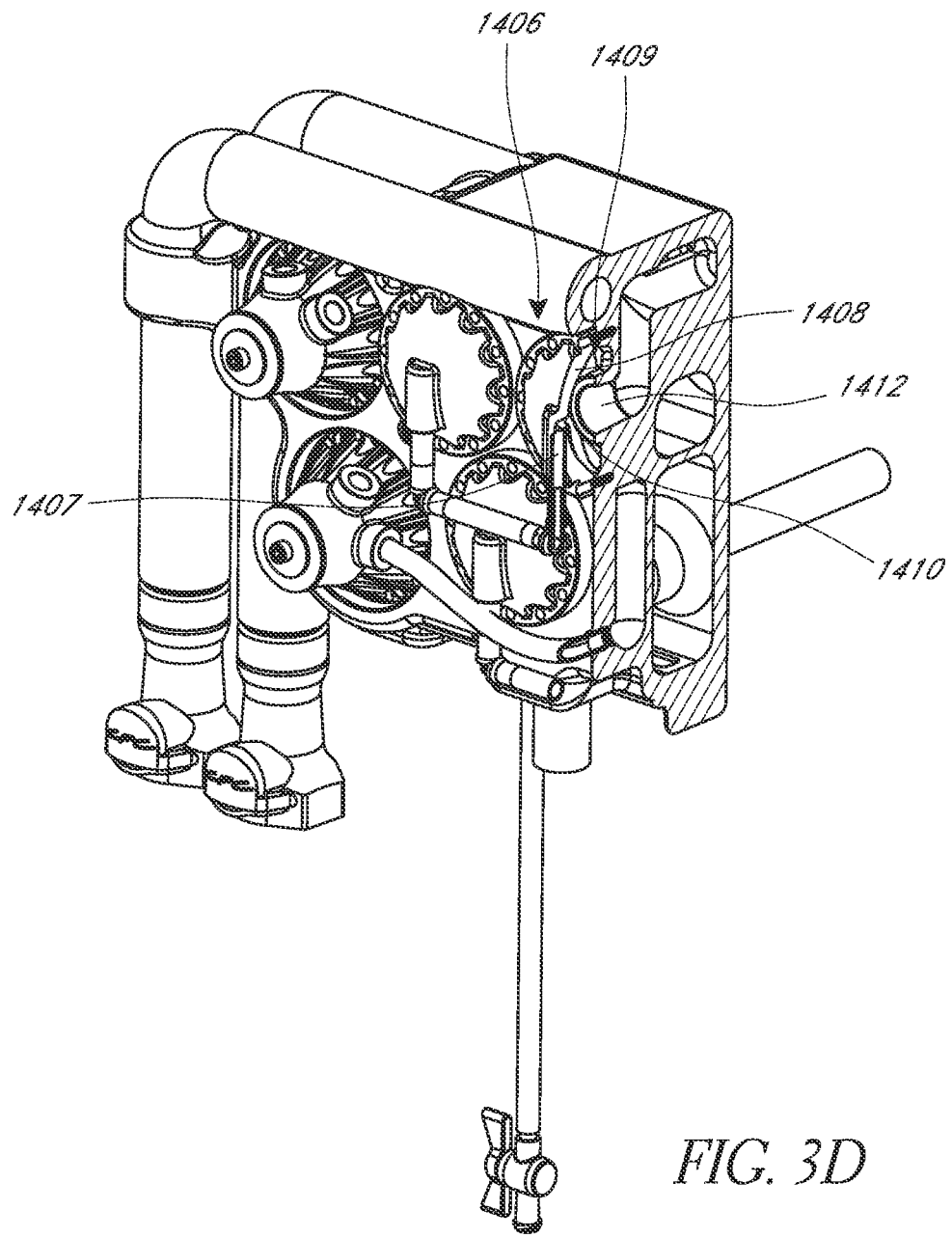
FIG. 3D illustrates a cross-section of a pneumatic piloted valve located on the circuit manifold in FIGS. 3A-3C.

FIG. 3D illustrates a cross-section of an exemplary pneumatic piloted valve, the No. 15 valve 1406. The valve 1406 comprises a diaphragm 1410, such as a thin rubber sheet, clamped between a dome 1409 and a passage 1412. When pressure is exerted downward from above 1407 the second valve cap 1408 by a pilot valve, the diaphragm 1410 is flattened to block the passage 1412, closing the No. 15 valve

1406. When vacuum is exerted downward from above 1407, the second valve cap 1416 by a pilot valve, the diaphragm 1410 is lifted up and away from the passage 1412, opening the No. 15 valve 1406.

In the illustrated embodiment, the opening and closing of the valves 1402, 1406, 1410, 1414 can cause the apparatus to switch between a pressure mode and a vacuum mode depending on whether an exhaust side of the diaphragm pump 190 goes to the atmosphere or to pressurize connected tubes, and vice versa on an vacuum side of the diaphragm pump 190 (shown I FIGS. 2B and 2D) as described above. More specifically as shown in FIG. 2C, a pressure line 1435 can connect the diaphragm pump 190 to the manifold 140 at a pressure port 1434 and a vacuum line 1437 can connect the diaphragm pump 190 to the manifold 140 at a vacuum port 1436. The No. 9 valve 1402, the No. 15 valve 1406, the No. 16 valve 1410 and the No. 17 valve 1414 on the manifold 140 are also connected to the diaphragm pump 190 and function similarly as the valves 1402B, 1406B, 1410B, 1414B in FIG. 1B so that the diaphragm pump 190 can exert a pressure in the inhale phase and a vacuum in the exhale phase.

In some embodiments, manually variable gate valves 1904 (shown FIG. 1D) are placed between the diaphragm pump 190 and the valves 1402, 1406, 1410, 1414, to control cadence of the machine via restricting flow. The opening and closing of the valves 1402, 1406, 1410, 1414, that is, the switching of the apparatus 1C between the inhale phase and the exhale phase, are in turn also controlled by the smaller pilot valves 1018, 1020, 1022, 1024 (described below). As described above and shown in FIG. 2B, the circuit manifold 140 also connects to the canister pressure control tube 1712. The pump 190 applies negative pressure in the canister 160 via the canister pressure control tube 1712 when the apparatus 1C is in the exhale phase so that the liquid 50 and gas withdrawn from the patient 2 can reenter the air-sealed canister 160 from the canister suction tube 1708. The pump 190 provides pressure to the canister 160 via the canister pressure control tube 1712 when the apparatus 1C is in the inhale phase to provide pressure in addition to that of the turbine pump 180 so that the liquid 50 can be delivered to the patient 2. The diaphragm pump 190 does not interact with the liquid 50 directly, keeping the design of the driver assembly 10 simple. The pump 190 can also lose any excess vacuum or pressure to atmosphere via the pressure and vacuum relief valves 1418, 1422 on the manifold 140 when more pressure or vacuum is produced than the patient needs. In some embodiments, the diaphragm pump 190 comprises a brushless motor to avoid fire and explosion hazards when gas removed from the lungs contain flammable gas, which may cause sparks in the presence of a brushed motor. All three pumps can be of brushless construction to prevent sparks in a flammable atmosphere. All switches in the embodiments described herein can be either electronic or of glass vacuum envelop isolated magnetic reed switch construction to prevent arching into a flammable atmosphere The diaphragm pump 190 is also connected via check valves (shown FIG. 1D) to a solenoid valve assembly 1000 comprising the valves 1018, 1020, 1022, 1024 (which are controlled by the control unit 186 and described below). In some embodiments, one or more auxiliary pumps 192, 194 (shown in FIGS. 1D, 2B and 2C) may be used. One of the boards of the control unit 186 can command the auxiliary pump 192 to shut off when a maximum control pressure is reached. Another one of the boards can command the auxiliary pump 194 to shut off when a maximum control vacuum is reached. The auxiliary pumps 192, 194 provide booster pressure in addition to a threshold pressure of the diaphragm pump 190 set by users in order to facilitate mode switching and/or positive opening/closing of the piloted valves. Specifically, the diaphragm pump 190 economically provides the bulk of pressure or vacuum to the valves 1018, 1020, 1022, 1024. The lower volume/higher pressure auxiliary pump 192 and higher pressure auxiliary pumps 194 can top off the bulk pressure/vacuum. The solenoid valve assembly 1000 is in turn connected to the caps/domes of valves 238, 1402, 1406, 1410, 1414, 2620, 2622, 2624 to control the captive diaphragms in those valves.

FIG. 1D illustrates an embodiment in which the solenoid valve assembly 1000 comprises four pairs of two-way solenoid valves. For each pair of valves, one valve receives pressure from the diaphragm pump 190 and the higher pressure auxiliary pump 192 on an input side and outputs pressure on an output side when the apparatus 1C is in the inhale phase. The other valve receives vacuum from the diaphragm pump 190 and the higher vacuum auxiliary pump 194 on the input side and outputs vacuum on the output side when the apparatus 1C is in the exhale phase.

As shown in FIG. 1D, the No. 15 valve 1406 and No. 16 valve 1410 on the manifold 140 and No. 10 valve 2620 on the patient circuit connect to an output side of a first pair of solenoid valves 1018 in the solenoid valves assembly 1000 via a first pressure/vacuum ("P/V") control line 1002. The output side of the first pair of solenoid valves 1018 also connects to a suction pilot line 1004 ending in the circuit connection port 120 to provide pilot pressure vacuum to the No. 10 valve 2620. The suction pilot line 1004 connects to the suction pilot tube 2202 of the tube assembly 20 (in FIG. 4A) and the suction pilot tube 2202 controls the opening and closing of the suction (No. 10) valve 2620. The No. 9 valve 1402 and the No. 17 valve 1414 on the manifold 140 also connect to an output side of a second pair of solenoid valves 1020 in the solenoid valves assembly 1000 via a second P/V control line 1006. The output side of the second pair of solenoid valves 1020 also connects to a gas delivery pilot line 1008 ending in the circuit connection port 120. The gas delivery pilot line 1008 connects to the gas delivery pilot tube 2204 of the tube assembly 20 (in FIG. 4A) and the gas delivery pilot tube 2204 in turn controls the opening and closing of the gas delivery (No. 5) valve 2622. An output side of a third pair of solenoid valves 1022 on the solenoid valves assembly 1000 connects to a liquid delivery pilot line 1010 and an output side of a fourth pair of solenoid valves 1024 connects to a liquid recirculation pilot line 1012 respectively, both pilot lines also terminating at the circuit connection port 120. The liquid delivery pilot line 1010 connects to the liquid delivery pilot tube 2206 of the tube assembly 20 (in FIG. 4A) and the liquid delivery pilot tube 2206 controls the opening and closing of the liquid delivery (No. 6) valve 2624. The liquid recirculation pilot line 1012 connects to the liquid recirculation pilot tube 2208 of the tube assembly 20 (in FIG. 4A) and the liquid recirculation pilot tube 2208 controls the opening and closing of the liquid recirculation (No. 8) valve 238. The valves in the solenoid valves assembly 1000 can be 0-18V N.C. (normally closed when not energized) solenoid valves. Combination of the pairs of solenoid valves and the pneumatic valves form pilot-piloted valves, whereby energizing one of the pair of solenoid pilot valves opens their corresponding pneumatic piloted valve and energizing the other one of the pair of solenoid pilot valves closes their corresponding pneumatic piloted valves.

Figure 2D:
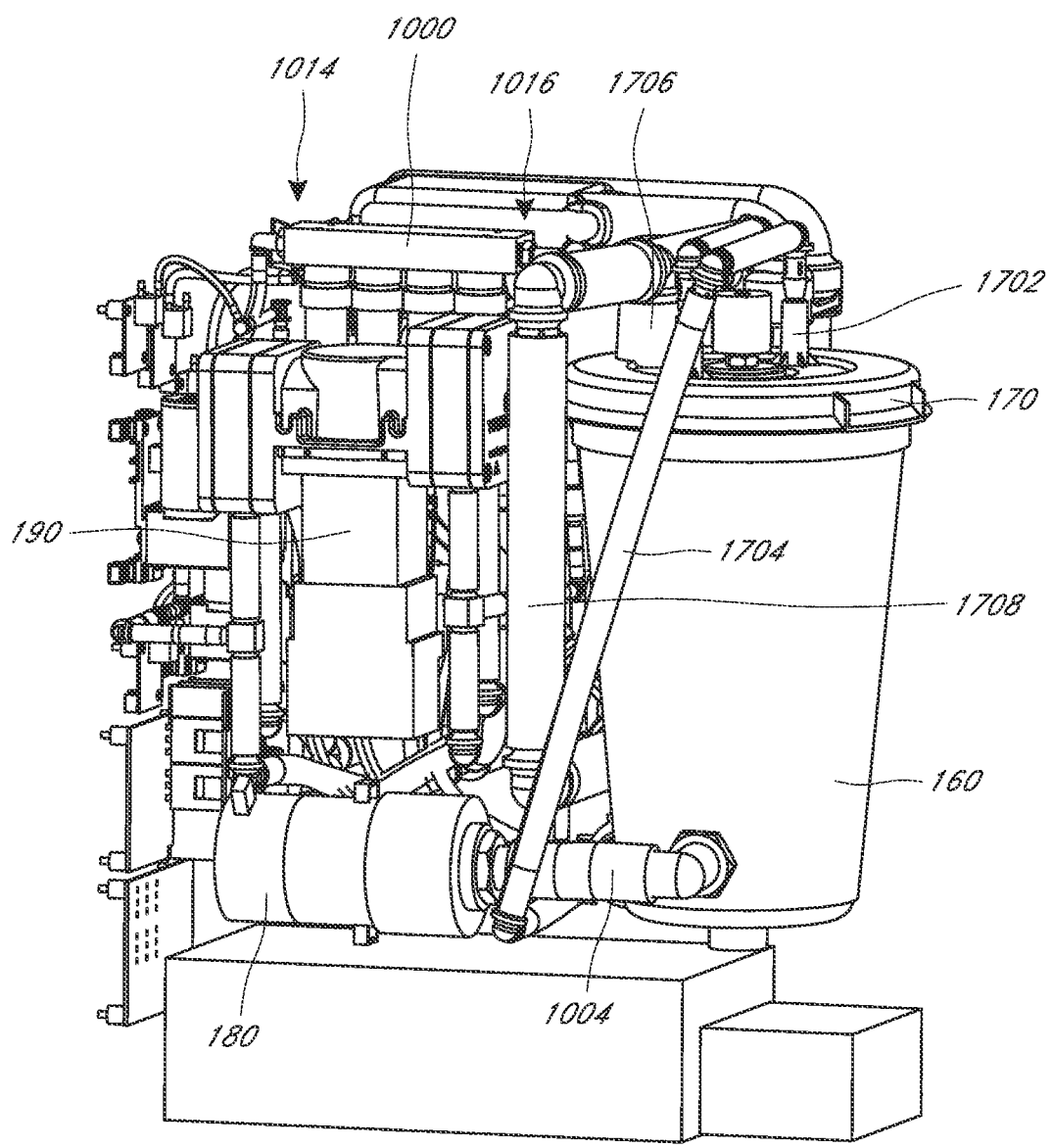
FIG. 2D illustrates a back view of the driver assembly in FIGS. 1C and 1D without the protective frame.
Figure 10A:
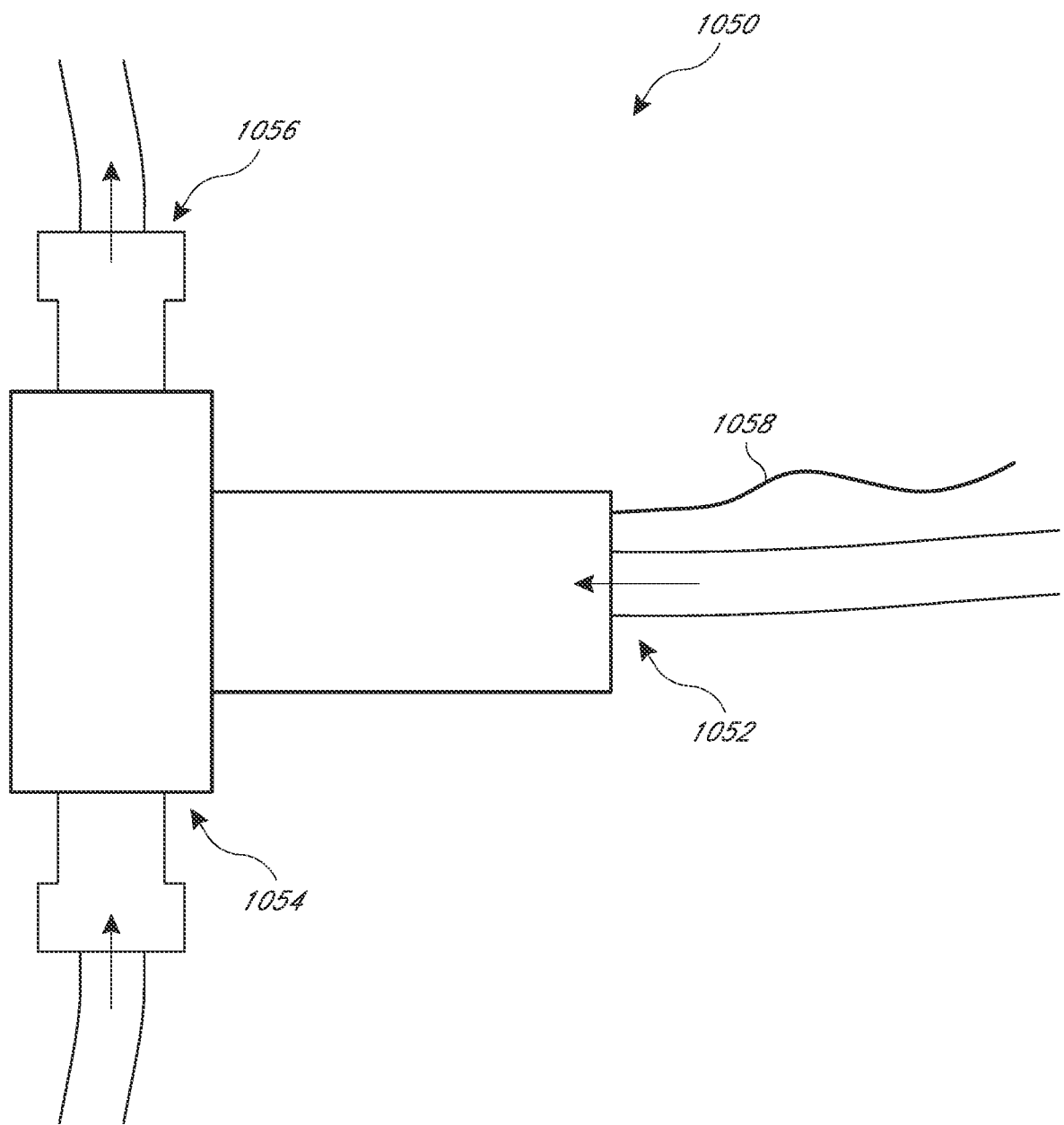
FIG. 10A is a schematic illustration of a three-way solenoid valve in accordance with an embodiment of the present disclosure.
Figure 10B:
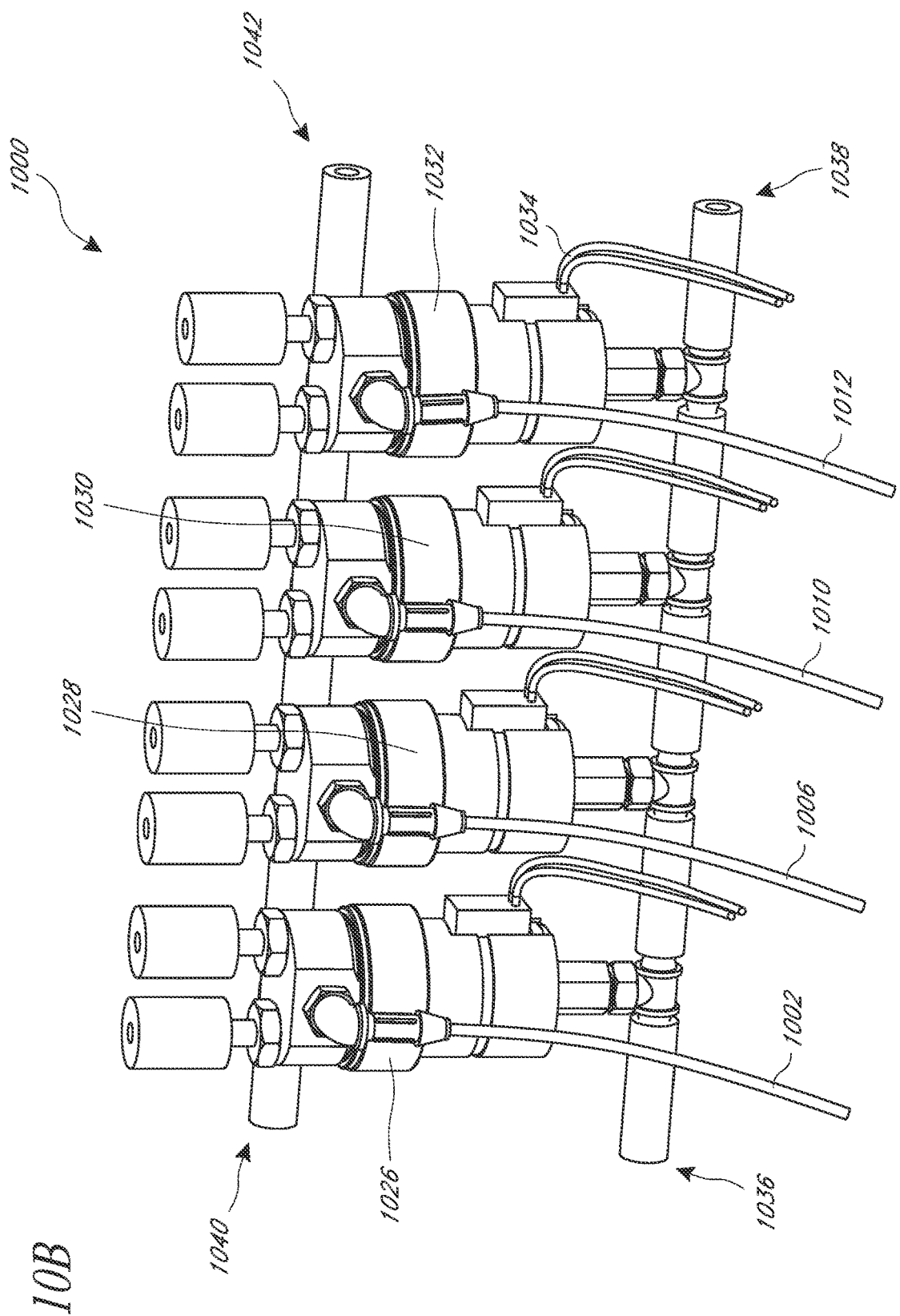
FIG. 10B illustrates a perspective view of a solenoid valve assembly comprising four three-way solenoid valves in accordance with an embodiment of the present disclosure.

In accordance with another embodiment of the present disclosure, such as shown in FIG. 2D, the solenoid valve assembly 1000 can comprise four 3-way custom-made solenoid valves instead of eight two-way solenoid valves. The 3-way solenoid valves advantageously promote portability, reliability, and economy by reduction in total parts count, lower cost per finished ventilator unit, lower power consumption, reduced volume, and reduced weight. FIG. 10A illustrate schematically a 3-way solenoid valve 1050. The 3-way solenoid valve 1050 receives pressure on a pressure inflow side 1052 when the apparatus 1C is in the inhale phase and receives vacuum on a vacuum inflow inside 1054 when the apparatus 1C is in the exhale phase. The 3-way solenoid valve 1050 output pressure or vacuum depending on the state of the apparatus 1C at an outflow side 1056. The 3-way solenoid valve 1050 receives state-switching signals from a signal wire 1058.

As shown in FIG. 2D, the diaphragm pump 190 and the auxiliary pumps 192, 194, if any, can connect to the solenoid valves assembly 1000 comprising four 3-way solenoid valves at a pressure side 1014 and an vacuum side 1016 of the solenoid valves assembly 1000. The solenoid valves assembly 1000 comprising the four 3-way solenoid valves, 1026, 1028, 1030, 1032 are more specifically shown in FIG. 10B. The 3-way solenoid valves 1026, 1028, 1030, 1032 are similar to the 3-way valve 1050 of FIG. 10A. Each valve comprises a pressure inflow side receiving pressure 1036 from the diaphragm pump 190 protected by the check valves (shown in FIG. 1D) and pressure 1038 from the pressure auxiliary pumps 192. Each valve also comprises a vacuum inflow side receiving vacuum 1040 from the diaphragm pump 190 protected by the check valves (shown in FIG. 1D) and vacuum 1042 from the vacuum auxiliary pumps 194. Each valve further comprises an outflow side providing pressure or vacuum depending on signals from signal wires 1034. More specifically, output of the first 3-way solenoid valve 1026 controls the pneumatic No. 15 valve 1406, the No. 16 valve 1410 and the suction (No. 10) valve 2620 via the first P/V control line 1002. Output of the second 3-way solenoid valve 1028 controls the pneumatic No. 9 valve 1402, the No. 17 valve 1414 and the gas delivery (No. 5) valve 2622 via the second P/V control line 1006. Output of the third 3-way solenoid valve 1030 controls the pneumatic liquid delivery (No. 6) valve 2624 via the liquid delivery pilot line 1010. Output of the fourth 3-way solenoid valve 1032 controls the pneumatic liquid recirculation (No. 8) valve 238 via the liquid recirculation pilot line 1012.

An embodiment of the present disclosure having pilot-piloted valves allow small solenoid valves to control larger pneumatically actuated valves, further reducing an overall size, power consumption, and weight of the driver assembly and making it more portable. Another advantage of this embodiment is that the first pair of 2-way solenoid valves 1018 or the first 3-way valve 1026 synchronize the opening and closing of the No. 15 valve 1406 and No. 16 valve 1410 on the manifold 140 (shown in FIG. 3B) and the suction (No. 10) valve 2620 (shown in FIG. 7A) so that the vacuum is applied to the canister 160 (shown in FIGS. 2A-2C) at the same time as to the suction tube 230 (shown in FIG. 4B) when the apparatus 1C is in the exhale phase. Likewise, the second pair of 2-way solenoid valves 1020 or the second 3-way valve 1028 synchronize the opening and closing of the No. 9 valve 1402 and the No. 17 valve 1414 on the manifold 140 (shown in FIG. 3B) and the gas delivery (No. 5) valve 2622 (shown in FIG. 7A) so that the gas flows through both the breathing tube 136 (shown in FIG. 2C) and the gas delivery tube 232 (shown in FIGS. 4A and 4C) when the apparatus 1C is in the inhale phase. In accordance with another embodiment of the present disclosure, the pressure/ vacuum control tubes and lines of the apparatus 1C can be color coded to make it easy for users to perform a quick safety check to make sure that all the tubes and lines are connected correctly before using the apparatus 1C or during potential malfunctioning of the apparatus 1C.

In accordance with another embodiment of the present disclosure as described above, the valves 2620, 2622, 2624, 238 may be normally opened or closed, and therefore do not require a two state application of pressure/vacuum to control respective valves. In this case, opening and closing the valves 2620, 2622, 2624, 238 can be done by smaller pilot valves 1018, 1020, 1022, 1024. The pilot valves may define an alternative valve assembly 1000A. Each valve may be controlled by the diaphragm pump 190. When pressure is applied by the diaphragm pump 190, the higher pressure auxiliary pump 192 applies pressure on an input side, which outputs pressure on an output side. This pressure is used to close valves 2620, 2622, 2624, 238, depending on the inhale/exhale cycle. Therefore, as shown, the multiple sets of two valve controls of assembly 1000 can be replaced with multiple single valve controls having either an open or closed configuration. This alternative is illustrated in the exemplary alternative 1000A assembly in the blown out portion of FIG. 1D.

Figure 8A:
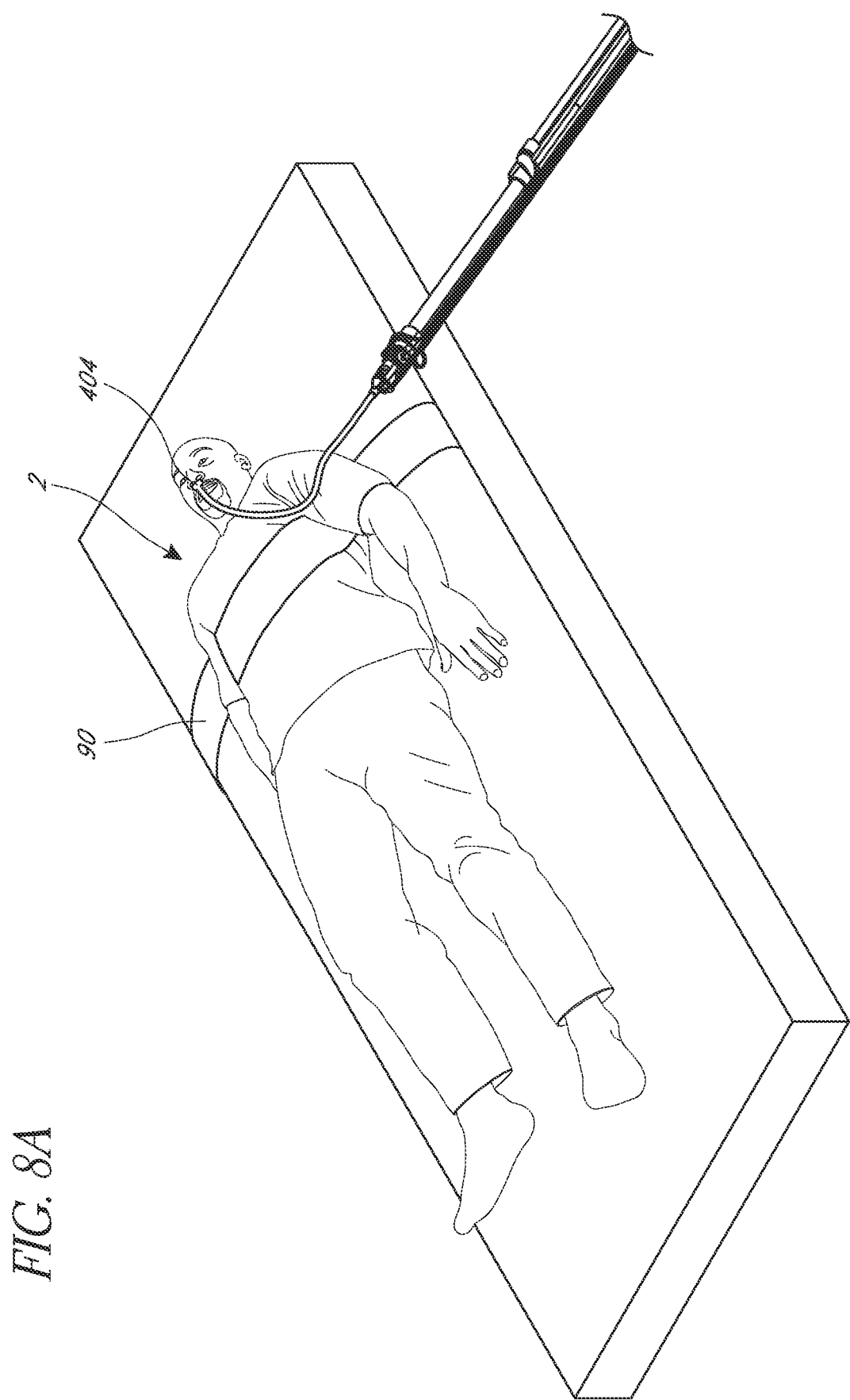
FIG. 8A illustrates a perspective view of a use of an example apparatus with an automatic CPR device on the chest of a patient in accordance with an embodiment of the present disclosure.
Figure 8B:
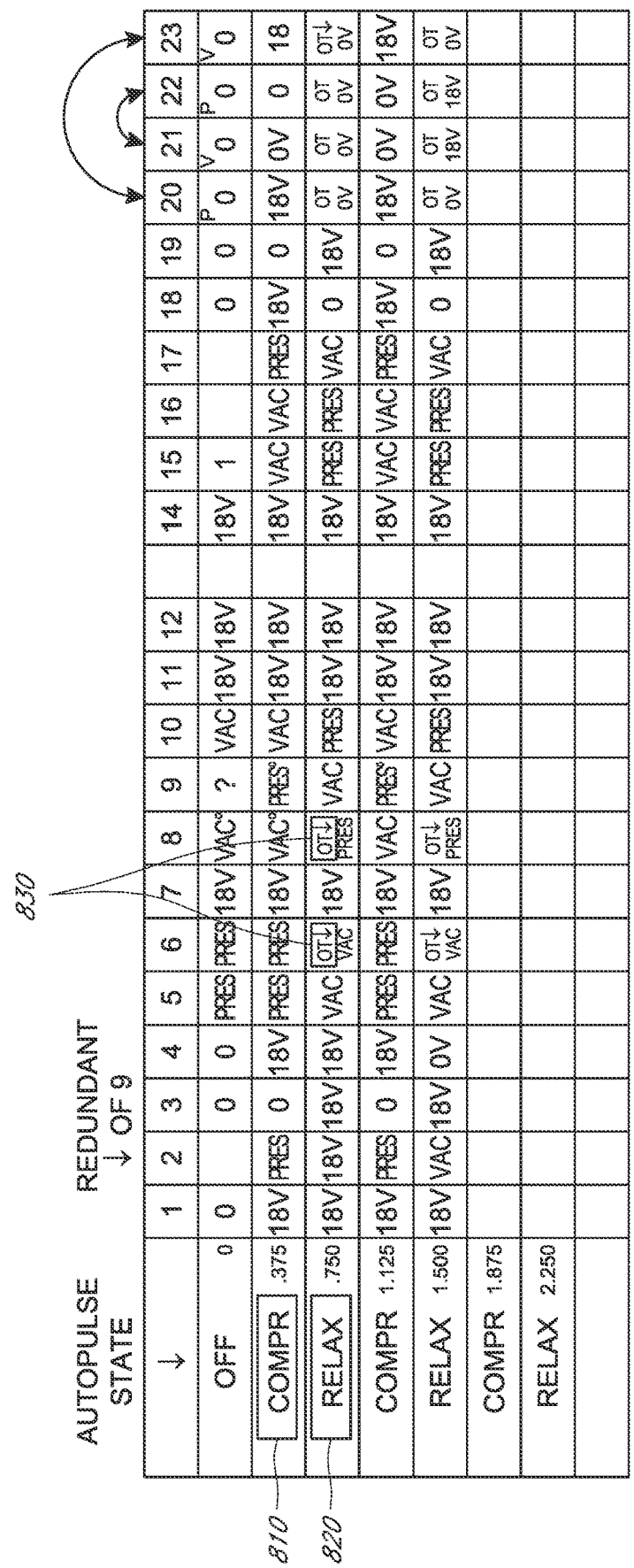
FIG. 8B is a timing table for the apparatus and an AutoPulse® CPR device as shown in FIG. 8A.

FIG. 8A illustrates an embodiment of use of the apparatus 1A, 1B or 1C on a patient with an automated CPR device, such as a Zoll AutoPulse® 80 or other manual or automated CPR device on the chest in accordance with an embodiment of the present disclosure. FIG. 8B is a table illustrating an example embodiment of the timing of opening and closing of all the valves on the apparatus 1A, 1B or 1C at different states of the AutoPulse® 80. For example, when an automated CPR device or a human administering CPR 80 switches to a COMPRESS state 810, the gas delivery (No. 5 valve) valve 2622, the No. 9 valve 1402 and the No. 17 valve 1414 can be closed so that no air is delivered to the patient 2. The suction (No. 10) valve 2620 can open immediately so that air or oxygen and the liquid 50 are sucked out of the lungs of the patient 2. On starting a RELAX cycle, the liquid delivery (No. 6) valve 2624 can have a small time delay 830 in opening and the liquid recirculation (No. 8) valve 238 can have a small time delay 830 in closing in accordance with an embodiment of the present disclosure. In one embodiment, the time delay is approximately 90 milliseconds. This time delay can be adjustable and can be used to create an initial puff of gas to precede liquid flow through to enhance oxygenation based on clinical observation hence PLV. In certain embodiments, the user can adjust the time delay via the user input of the control unit. In certain embodiments, in the inhale phase, a valve in the gas delivery passage allows gas to flow an adjustable number of milliseconds (or other time interval) prior to a delayed opening of a valve in the liquid delivery passage, which in turn can shut off the valve in the gas delivery passage from back pressure or in certain embodiments the valve can be closed in response to an electronic timer. The suction phase or the inhale phase can be delayed momentarily relative to the phase of the CPR to create extra pressure or vacuum respectively in the thoracic cavity of the patient 2 during manual or automated CPR, thus increasing blood flow to the vital organs. As soon as the automated CPR device, or a human administering CPR 80 switches a RELAX state 820 and before the pressure in the patient's airway reaches the preset threshold value, the gas delivery (No. 5 valve) 2622, the liquid delivery (No. 6) valve 2624, the No. 9 valve 1402 and the No. 17 valve 1414 can be open to deliver air or oxygen and the fluid 50 to the patient 2, while the suction (No. 10) valve 2620 and the liquid recirculation (No. 8) valve 238 are closed so that flows in the suction tube 230 and the fluid recirculation tube 240 are closed. The RELAX state 820 may last for approximately 0.375 second allowing blood flow into the chambers of the heart except optional "deep breath" parts of the cycle, or alternately a "breathe" part of the manual CPR cycle included to help oxygenate the patient. When the threshold pressure is reached in the patient's airway, the AutoPulse® 80 automatically switches back to a COMPRESS state 810 for approximately the next 0.375 second allowing blood flow out of the chambers of the heart excepting optional "deep breath" parts of the cycle, or alternately the "breathe" part of the manual CPR cycle included to help oxygenate the patient for example by getting fresh air into the lungs. The cycle of compression states and relax states can be repeated for as long as needed. In addition, the AutoPulse® 80 is just one way of providing CPR to the patient 2. It is contemplated that compression to the patient's chest can also be achieved by other automated devices such as the "Thumper®" (Michigan Instruments Inc), manually by pulling on an inelastic adjustable band around the chest of the patient, or by any other method of increasing pressure in the heart/lungs known or obvious to one of ordinary skill in the art. One of ordinary skill in the art may contemplate from the disclosure herein other timing schedules of the AutoPulse® states or of opening and closing of the valves in the apparatus. In accordance with one embodiment of the present disclosure, separate timing of valves controlling delivery of the fluid and valves controlling delivery of air or oxygen or other gas may also be contemplated by one of ordinary skill in the art to adjust the exact proportional bend of gases and the liquid.

Figure 11:
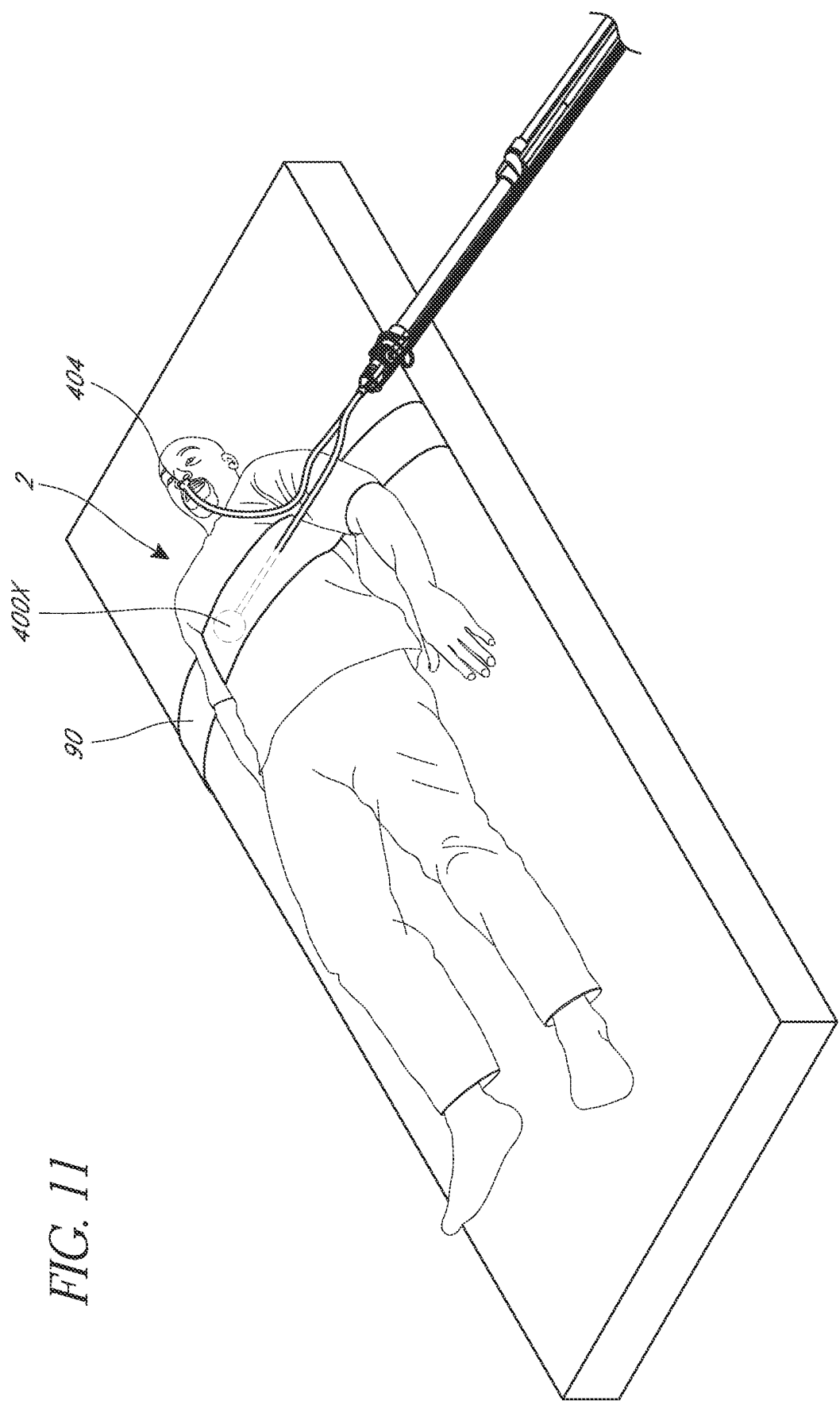
FIG. 11 is a schematic illustration of an example embodiment apparatus used in connection with an embodiment of an inelastic band.

In certain embodiments, for example, as shown in FIG. 11, the apparatus 1A, 1B, 1C can be used in combination with a band 90, which can be an inelastic and/or adjustable band (such as a belt) in certain embodiments, positioned around the patient's chest. A pressure sensor 400X can be coupled to the band, for example, placed underneath the band 90, instead of or in addition to being placed on the endotracheal tube. The band 90 can advantageously providing for an elegant method of registering pressure set points, but can also advantageously limit stretching of the lungs to prevent volutrauma. The lungs may be more susceptible to injury by over-stretching than by high pressure alone. Limiting the stretching of the lungs by the band may advantageously create a higher $P_{aw}$ that is easier for the apparatus to register. In this way, monitoring the $P_{aw}$ may permit a maximum $P_{aw}$ to safely be reached in the patient with reduced fear of potential over-inflation by over-stretching as compared to treatment without a band. This embodiment can be advantageously used on injured, premature, or diseased lungs or other anatomies that must be limited in extension. As with many features and aspects described in this disclosure, the use of a band 90 around the patient's chest can also find utility and be advantageous when used in combination with conventional gas ventilation device, and/or other apparatuses configured for ventilation, TLV and/or PLV and need not be used in combination with the features of the embodiments described herein.

In accordance with certain embodiments of the present disclosure, the embodiments of the fluid of the apparatus 1A, 1B, 1C can be cooled or heated by directly mixing the fluid with cold or hot water. In such embodiments, the apparatus 1A, 1B, 1C does not need to include a heat exchange assembly. In such embodiments, if a hydrophobic fluid is used, the fluid and water mixture can form an emulsion which lasts for around 30 minutes. The cold or hot water may be introduced into the canister containing the fluid immediately before connecting the apparatus to a patient. Alternatively, the cold or hot water may be introduced via a connection tube coupled to the proximal end of the endotracheal tube to be mixed with the fluid before entering the lungs of the patient.

In accordance with an embodiment of the present disclosure, the apparatus comprises a driving assembly, a tube assembly and a hot water bath assembly. The hot water bath assembly provides hot water to a heat exchange assembly in the tube assembly in order to warm a liquid that is delivered to lungs of a patient.

As described above, the embodiments described above with reference to apparatus 1A, 1B, 1C can be provided with adjustable timing. That is, in certain embodiments, the user via for example user interface can adjust the timing and/or duration of the inhale phase, the exhale phase, delivery of gas to lungs, and/or delivery to liquid to the lungs. The volume and/or pressure of gas and/or liquid delivered during these phases can also be adjusted by the user. This adjustability can provide several purposes and provide several advantages. For example, in certain embodiments, adjusting the delay of liquid delivery relative to gas delivery in the inhale phase can provide an elegant and robust method of varying the gas/liquid ratio provided to the patient in an apparatus that can also function as a conventional ventilator if there is no liquid present in the reservoir. In addition, in certain embodiments, the timing of either the gas delivery and/or liquid delivery and/or extraction event (e.g., application of vacuum) can be used to enhance blood flow, particularly in the absence of an adequate or any heartbeat. For example, momentarily delaying the release of the lungs contents while pressurizing the lungs in CPR can cause a slight temporary pressure on the heart which can serve to pump blood. In a similar manner, momentarily blocking entry of fluid into the lungs in the "relax" phase of CPR can cause a momentary negative pressure on the heart can cause the heart's chambers to fill with blood to a greater volume than without such steps. Accordingly, in certain embodiments, the adjustability described above (e.g., the delay of exhale and/or inhale relative to the CPR) can be used to apply additional pressure or vacuum to enhance blood flow, particularly in the absence of adequate or any heartbeat. In certain embodiments, the apparatus 1A, 1B, 1C can include a manual override to adjust the timing and/or duration of the inhale phase, the exhale phase, delivery of gas to lungs, and/or delivery to liquid to the lungs. In certain embodiments, the apparatus 1A, 1B, 1C can adjust the timing and/or duration of the inhale phase, the exhale phase, delivery of gas to lungs, and/or delivery to liquid to the lungs based on additional signals or through a feedback loop based on for example measured pressure, tension in adjustable band 90 and/or application of pressure to a patient's lungs during a cardiopulmonary resuscitation procedure.

The embodiments described above with reference to apparatus 1A, 1B, 1C can be provided with a fluid containment and/or filter for containing and/or filtering gas and/or liquid removed from the lungs of the patient. In one embodiment, the fluid containment and/or filter is connected to the apparatus by a quick disconnect and can be in communication with the suction passage.

In some embodiments, the protective cage-like frame 108 of the driver assembly 10 in FIG. 1C can be of a shape and size such that the driver assembly 10 fits snugly into an off-the-shelf ice cooler. It is contemplated that this driver assembly 10 can be cheaply and safely transported using the off-the-shelf ice cooler, for example, in the trunk of a car or an overhead cabinet of an airplane. In certain embodiments, the illustrated frame 108 of FIG. 1C can include open frame constructions, which aids the user in accessing the components within the frame 108 and/or the frame 08 can include see through panels or coverings.

Figure 1E:
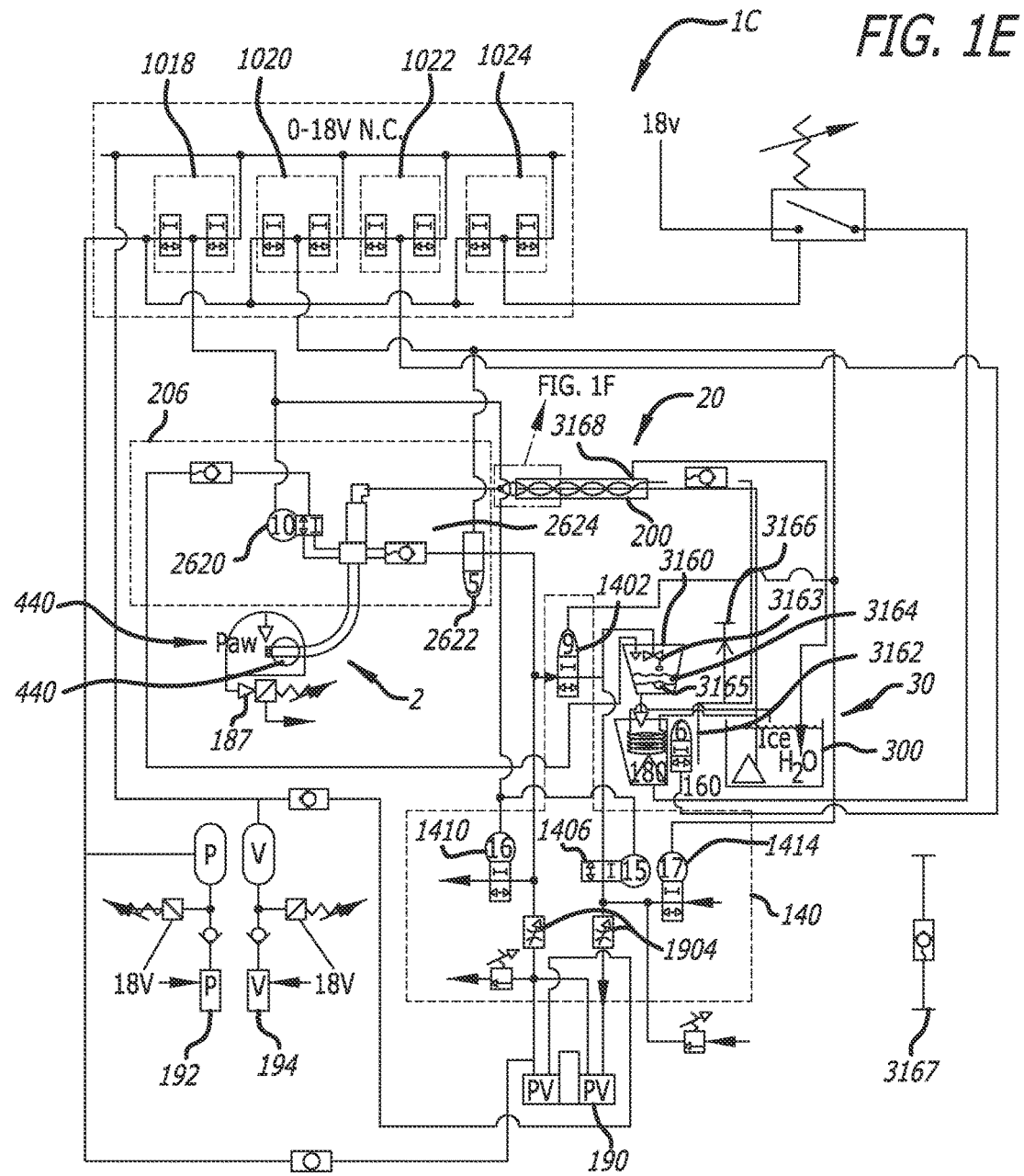
FIG. 1E is a block schematic diagram of an improved device according to embodiments described herein.
Figure 1F:
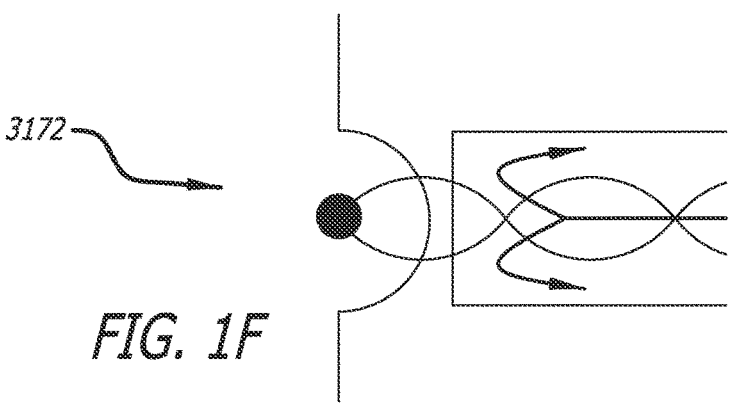
FIG. 1A illustrates a schematic diaphragm of an apparatus in accordance with an example embodiment of the present disclosure.
FIG. 1 F is an enlarged section view of a close-up of region F of FIG. 1E showing the terminus of a cooling fluid tube and the exit of the cooling fluid into the jacket of the fluid delivery device, and it's travel rearward (opposite the flow of breathable liquid) to the exit at 3168 where the cooling fluid is conducted back to the ice bath.

Additional embodiments may incorporate alternatives for specific or general purposes as shown in FIG. 1E. Note shown in the figure for brevity is alternative valve assembly 1000A though it is equally applicable in this case. FIG. 1E provide exemplary changes and additions relative to FIG. 1D device for purposes of economy, portability, and ease of use. The patient fluid delivery/heat exchanger device 200 is configured here to conduct breathable liquid in the forward (toward the patient) direction via multiple corrugated tubes wound in helix fashion about a flexible core tube 3168 shown in FIG. 1F, which conducts coolant liquid toward the patient terminating approximately an inch or two, before the molded or 3D printed end block 2602. The coolant fluid then progresses rearward transferring heat from or to the incoming breathable liquid and any gasses which may have been added to it. There may optionally be two or more separate entry ports for the breathable liquid so that the device can be used with the "loop back" method if desired. Note that the option of controlling the breathable liquid turbine 180 is shown. Pressure switch 3169 is configured to interrupt or reduce power to the turbine 180 via a pressure signal herein illustrated as originating at valve 1024 such that the turbine slows or ceases during the exhale or extraction of fluid phase, conserving power and extending the use life of the turbine. Also in this embodiment, an "upper" (as depicted in FIG. 1E) reservoir has been added to receive fluid. Optionally, this reservoir is a transparent material with volume markings, or has a transparent window with volume markings so that the amount of liquid used by the patient may be known. A "lower (as depicted in FIG. 1E) reservoir is configured with a heat exchanger to provide additional cooling/warming as required. In addition to adding additional heat exchanger surface to the system for greater heat transfer, this serves the purpose of cooling the turbine to improve its reliability and service life. In this case the coolant fluid, which may be water ice or water ice with added alcohol or salt to reduce temperature, flows through the coil 3172 (shown in FIG. 1F) cooling or warming the contents of the lower reservoir. The cooling fluid may be obtained via branching off from the main coolant supply to the patient fluid delivery device 200 as shown. Those skilled in the art will recognize that use of the returning coolant from the Patient Fluid Delivery/Heat Exchanger device 200 may also be used as well as connecting the coil to the return path of breathable liquid from the patient and placing it in the Ice Bath 300. It will also be recognized by those skilled in the field that the cooling fluid may be replaced by a warming fluid to add heat to the patient. Fluid may be rapidly warmed by means of an integral heater or a microwave device. For efficiency and to protect the device, a float valve is used at the terminus of the vacuum line which provides suction to the reservoir. The float valve may be configured as a polymer ball captured inside a perforated cup such that if the reservoir is overfilled, the polymer ball will float atop the liquid and occlude the suction port. Additional enhancements are also illustrated at 3164, where a layer of light fluid (i.e. less dense than the breathable liquid being used) covers the surface of the breathable liquid. This has proven useful in slowing consumption of the breathable liquid. To aid the operator in knowing the volume of covering liquid, a float 3165 may be added. This float has a density between that of the breathable liquid and that of the covering liquid. It has been found in practice that many ordinary polymers meet the requirement of densities between commonly available PFC liquids and that of water, which may be used as a low cost covering liquid. Also shown is Filling Aid 3167. Filling Aid may be connected to the Fill Port shown, 3166. Note that fill port is a normally closed "quick connect" type port as commonly available in commerce and engineering from such firms as CPC and others which are opened via connecting to the appropriate mating valve so that minimal or no spillage or leakage results even when under pressure or vacuum. Note that the Fill Aid 3167 is two ended so that if connected via one end, breathable liquid may be drawn in to the system during the exhale phase, or drained from the system during the inhale phase if connected via the other end due to the orientation of the check valve.

Figure 13:
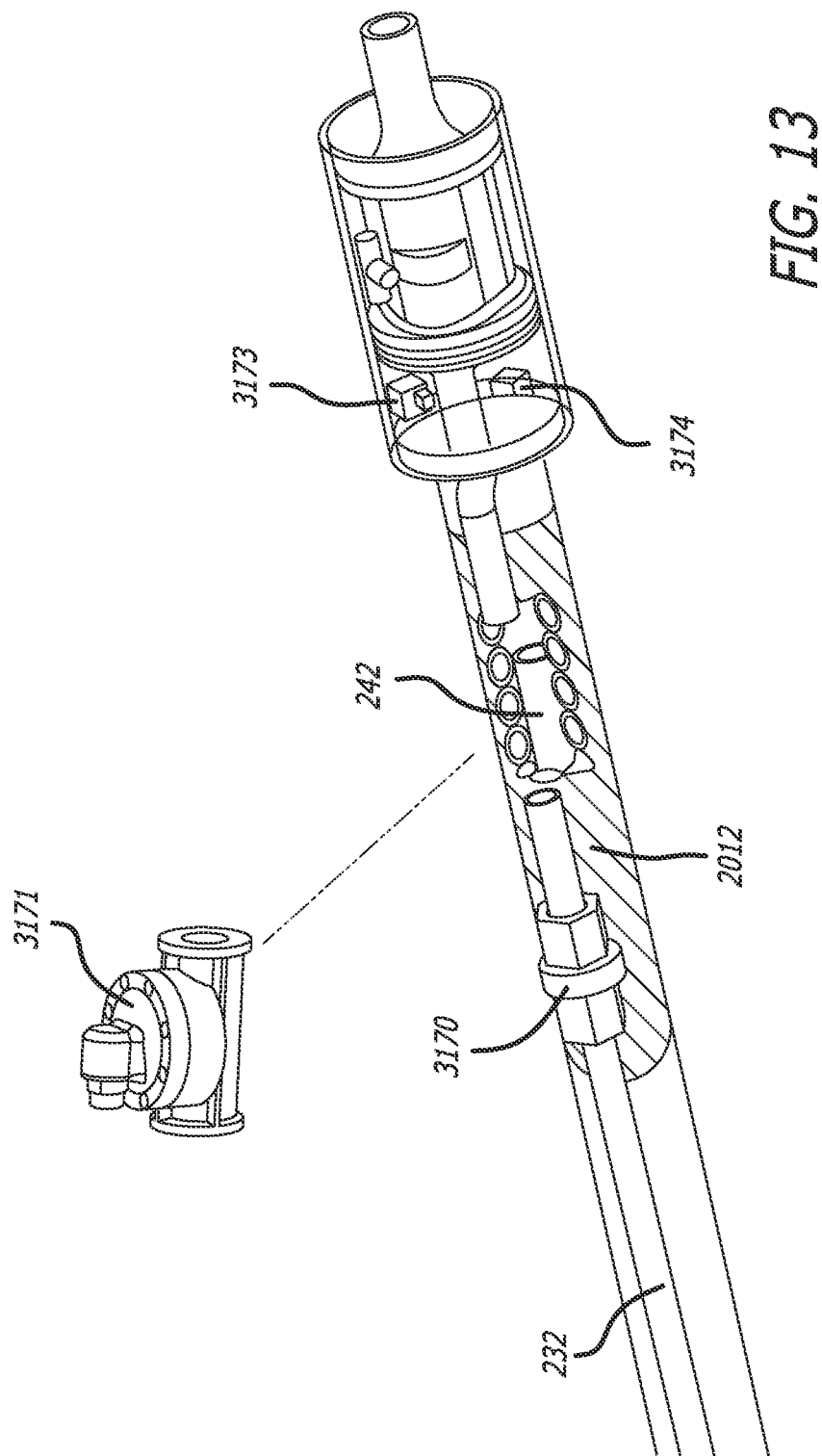
FIG. 13 illustrates an exemplary improved delivery device in cutaway showing a helical heat exchanger built of 6 heat exchanger tubes wound helically around a core that is made by the coolant inlet tube, and optional inline diaphragm valve consistent with FIG. 12.

FIG. 13 shows an exemplary improved patient fluid delivery device in cutaway view for instruction. In this case shown, the heat exchanger/breathable liquid delivery device is constructed of 6 preferably corrugated tubes for carrying breathable liquid of generally helical shape. The helix may be substantially coaxial with the Cold Water Inlet Pipe 242, which is shown terminating in an open end. Also note that in this embodiment, check valve 3170 may augment or replace any that may be within middle portion 2604 and said Middle Portion may be absent entirely. Proximal portion 2602 may be absent or reduced, the valves 2620, 2622, and 2624 may be replaced with inline valves.

In a preferred embodiment, there are 6 helical heat exchanger tubes which meet at a plenum inside the molded or 3D printed distal end such that they may also be used with the loop-back system described earlier if appropriate, or used with all 6 or more, or fewer helical tubes conducting breathable liquid or breathable liquid with some amount of gas or bubbles only in the forward direction. The evacuation tube could be a separate tube not shown here. This separate evacuation tube may connect to a Y fitting at the distal end of the device connecting to an endotracheal tube and include its own valve as 3171 (in this case it would correspond to 2620 of FIG. 1E) and its own check valve as 3170 (shown in FIG. 1E downstream of "Valve 10" 2620. It may also be configured as a heat exchanger and or may have some portion of its length constructed of a thermal conducting material placed in the ice bath 300 for additional cooling.

Exemplary embodiments described herein may benefit from disposable components. For example, the system may be subdivided into attachable component parts such that those having patient contacting surfaces may be removed and replaced, thereby improving cleaning and/or sterility between uses. System components may also be designed to separate or otherwise be shaped or configured to improve the ability to clean and/or sterilize component parts by other methods. For example, the disclosed snorkel may have multiple versions so that it can be interchangeable such that it can be used as a wet or dry or combination snorkel. This component may be disposable and replaceable between users. For the patient contacting surfaces, the components are preferably made of a biocompatible material or include a biocompatible coating or surface layer. The system may therefore be configured to be cleaned and sterilized in place before transport or in the field before use. The system may also be cleanable or disinfectable in the field either by accessing component parts or by replacing disposable components that may be provided in a kit for field use or together as a total system.

Exemplary embodiments may also include component parts configured to improve serviceability and accessibility of other component parts. For example, components may snap, screw, or otherwise easily be removed or separated to provide access or replacement of failed or worn parts.

Exemplary embodiments may also include internal filters to prevent bacterial infection or growth of undesirable substances. Therefore, fluid lines, including gas and liquid lines may include filters, chemicals, or other mechanism to reduce bacterial growth and limit a spread of infection.

Exemplary embodiments may also include apertures, windows, transparent or semi-transparent portions to visualize an interior portion of the system. For example, to track liquid levels, the reservoir could be transparent, translucent, or combinations thereof or otherwise have a port for viewing a liquid level. Other measurement mechanisms may be used such as a float gauge to monitor a liquid level within the system.

Exemplary embodiments described herein may be manufactured by use of 3D printing. A number of components described herein may not include conventional linear passages or easily machined component parts, including ports, valves, attachment portions, tubes, etc. As described herein, proximal portion of distal flow connector, or parts of the circuit manifold may be such unconventional configurations. Portions of the heat exchanger and endotracheal tube may similarly benefit therefrom.

Exemplary embodiments include a liquid cooler for a liquid or partial liquid breathing apparatus constructed as a vessel for pressure or vacuum through which a breathable liquid flows, comprising one or more coiled corrugated tubes through which cooling fluid flows.

Exemplary embodiments include an apparatus for providing liquid to a lung, comprising: a delivery device configured to deliver a fluid to the lung; a liquid delivery passage, a gas delivery passage, and a suction passage, the liquid delivery, the gas delivery, and the suction passages in fluid communication with the delivery device; a fluid reservoir in fluid communication with the liquid delivery passage; a vacuum source in communication with the suction passage; a gas source in communication with the gas delivery passage; a pressure sensor; one or more valves configured to control flow through the liquid delivery, the gas delivery, and the suction passages when the apparatus switches between an inhale phase and an exhales phase; and a control unit operatively connect to the pressure sensor and the one or more valves, the control unit configured to, in response to a signal from the pressure sensor, switch the apparatus between an inhale phase in which the fluid is delivered to the delivery device by either a liquid from the fluid reservoir through the liquid delivery passage and to the delivery device or a gas from the gas source to the gas delivery passage to the delivery device and an exhale phase in which a delivered fluid is withdrawn from the delivery device into the suction passage.

Exemplary embodiments include a fluid delivery device for a liquid or partial ventilator comprising: a central tube for conducting liquid from a proximal end of the tube forward toward a patient and open internally to the device at a distal end thereof such that cooling or warming fluid flows through the central tube away from the patient; one or more helical tubes coaxial to the central tube, the one or more helical tubes conduct breathable liquid toward the patient, the one or more helical tubes in contact with the central tube; one or more tubes which conduct gas to the patient; and one or more tubes which conduct extracted fluids away from the patient.

Exemplary embodiments include an apparatus for providing liquid to a lung, comprising: a delivery device configured to deliver a fluid to the lung, the delivery device having a liquid delivery passage, a gas delivery passage and a suction passage, a fluid reservoir in fluid communication with the liquid delivery passage; a vacuum source in communication with the suction passage; a gas source in communication with the gas delivery passage; a pressure sensor; one or more valves configured to control flow through the liquid delivery, the gas delivery and the suction passages when the apparatus switches between an inhale phase and an exhale phase; a control unit operatively connected to the pressure sensor and the one or more valves, the control unit configured to, in response to a signal from the pressure sensor, switch the apparatus between the inhale phase in which a fluid is delivered to the delivery device by either a liquid from the fluid reservoir through the liquid delivery passage and to the delivery device or a gas from the gas source to the gas delivery passage to the delivery device and an exhale phase in which a delivered fluid is withdrawn from the delivery device into the suction passage; a tube assembly comprising a liquid delivery tube, a gas delivery tube, a suction tube, and a heat exchanger extending along a length of the tube assembly; and a heat reservoir in fluid communication with the heat exchanger, and the heat exchanger comprises one or more corrugated tubes wound in a helical fashion about a central cooling liquid supply tube contained within the fluid delivery device.

Exemplary embodiments include an apparatus for providing liquid to a lung, comprising: a delivery device configured to deliver a fluid to the lung; a liquid delivery passage, a gas delivery passage and a suction passage, the liquid delivery, the gas delivery and the suction passages in fluid communication with the delivery device; a fluid reservoir in fluid communication with the liquid delivery passage; a vacuum source in communication with the suction passage; a gas source in communication with the gas delivery passage; a pressure sensor; a one or more valves configured to control flow through the liquid delivery, the gas delivery and/or the suction passages when the apparatus switches between an inhale phase and an exhale phase; a control unit operatively connected to the pressure sensor, mechanical force sensor, or manual switch, and the one or more valves, the control unit configured to, in response to a signal from the pressure sensor, mechanical force sensor, or manual switch, to switch the apparatus between an inhale phase in which the liquid from fluid reservoir is delivered through the liquid delivery passage and to the delivery device and/or gas can be delivered from the gas source to the gas delivery passage to the delivery device and an exhale phase in which liquid and/or gas can be withdrawn from the delivery device into the suction passage.

Exemplary embodiments may also include any combination of exemplary features. For example, the apparatus may further comprise a liquid cooler having one or more coiled corrugated tubes through which cooling fluid flows; the coiled tubes may be a in helical configuration about delivery and/or retrieval tubes according to embodiments described herein. The delivery device may include a cooling jacket that may be defined a closed coil loop or by a single sheet. The apparatus may further include a secondary cooler or warmer for the withdrawn delivered fluid in the suction passage, the secondary cooler or warmer comprising another liquid to cool or warm the withdrawn delivered fluid extracted from a subject; a primary cooler having a distal end connected to the delivery device, wherein the primary cooler is configured to introduce cooling liquid proximally and co-axially with the delivery device via a flexible tube which extends distally toward a subject and from which coolant then flows proximally in the opposing direction of a flow of breathable liquid within an outer fluid jacket of the delivery device; a temperature sensor that may be positioned in a liquid path near to a subject when the apparatus is in use, the temperature sensor used to modulate liquid being delivered from the apparatus; a heat exchanger in the suction passage, wherein modulation is effected via slowing or interrupting a flow of thermal liquid, diverting a flow of thermal liquid, and combinations thereof from the heat exchanger; a pressure sensing switch coupled to a pump or turbine, the pressure sensing switch terminates or reduces power to the pump or turbine that supplies breathable liquid, during the exhale phase; an ice bath having water and ice with a chemical to depress a solid to liquid phase change of ice; and/or any combination thereof.

Exemplary embodiments may also include any combination of exemplary features. For example, the device may further comprise a bifurcation in an inlet such that the one or more helical tubes are divided into a forward and rearward circuit; a filling device having a "quick disconnect" valve activated by connecting to a mating part which compresses an internal spring and opens a fluid path; a turbine and a sparging device near the turbine to admit gasses into a stream of breathable liquid from the delivery device; a variable timing device so that a portion of the inhaled fluid which is gas may be controlled; a spring that may be used to bias that valve so that only one of pressure or vacuum need be applied to determine a state of the valve; a feedback loop in communication with a pulse oximeter or photoplethysmic device for modulating gasses introduced into a patient from the delivery device; comprising an integral heater placed in a fluid line of the device; one or more reservoir canisters having a transparent window and volumetric markings to permit a user to observe an ingress or egress of breathable liquid from the one or more reservoir canisters; the filling device is reversible for use in either filling or draining breathable liquid; a manifold comprising a transparent 3D printed component with a surface applied of biocompatible epoxy; a single primary entrance point for gasses to the delivery device are controlled, treated, or mixed; a single primary exit point for gasses from the device wherein the gasses are contained; and/or any combination thereof.

Exemplary embodiments may also include any combination of exemplary features. For example, the one of the one or more valves may comprise: at least one 3D printed valve that is constructed containing a compliant seal device that capture a diaphragm and wherein the diaphragm is constructed larger in diameter than a female receptacle of the 3D printed valve causing a bowing effect on the diaphragm increasing a flow path during an open condition of the valve wherein an opening and closing of the valve is effected via pressure or vacuum applied to one side of the diaphragm; one of the one or more valves may comprise a diaphragm which fits into a cylinder such that the cylinder is smaller in diameter than the diaphragm resulting in the diaphragm taking a convex or concave shape; one of the one or more valves may be a control valve of a transparent 3D printed component with a surface applied of biocompatible urethane; and/or any combination thereof.

Exemplary embodiments may also include any combination of exemplary features. For example, the delivery device is an endotracheal tube; the pressure sensor is operatively connected to a portion of the endotracheal tube; the source of liquid in fluid communication with the liquid delivery passage comprises an oxygenated liquid; the one or more valves configured to control flow through the liquid delivery, the gas delivery and/or the suction passages when the apparatus switches between an inhale phase and an exhale phase comprise a liquid delivery valve, a gas delivery valve, and a suction valve; the liquid delivery valve, the gas delivery valve, and the suction valve are positioned within the liquid delivery, the gas delivery and the suction passages respectively; and/or the liquid delivery, the gas delivery and the suction passages are positioned within a hub that is connected to a proximal end of the delivery device.

Exemplary embodiments may also include any combination of additional features, such as, for example a tube assembly comprising a liquid delivery tube, a gas delivery tube, a suction tube, and a heat exchanger extending along a length of the tube assembly, the liquid delivery tube in fluid communication with the liquid delivery tube, the gas delivery tube in fluid communication with the gas delivery passage, the suction tube in fluid communication with the suction passage. In this case, the apparatus may also include a heat reservoir in fluid communication with the heat exchanger. The heat exchanger may comprise a liquid delivery tube and a liquid recirculation tube extending along at least a length of the tube assembly. Heated or cooled fluid may be recirculated through the liquid delivery tube and the liquid recirculation tube during inhale and exhale phases. The liquid delivery tube and the liquid recirculation tube may form a double helix. The delivery line and a return line may be formed from corrugated tubes.

Exemplary embodiments may also include the control unit configured to deliver liquid to the lungs through the delivery device only when the apparatus is in the inhale phase and to withdraw liquid from the lung through the delivery device only when the apparatus is in the exhale phase. The inhale phase may be triggered when the control unit receives a pressure signal equal to a preset vacuum and the exhale phase is triggered when the control unit receives a pressure signal equal to a threshold pressure or is triggered by a mechanical force sensor or manual switch. The control unit may include a manual override to control the inhale phase and/or exhale phase. The control unit may include a sensor that detects application of pressure or mechanical force to a patient's lungs or chest during a cardiopulmonary resuscitation procedure.

Other exemplary features that may be present in any combination include the suction passage is in fluid communication with the fluid reservoir, a recirculation tube passage in fluid communication with the liquid delivery passage and the fluid reservoir, the control unit is configured to recirculate liquid from the liquid delivery passage through the liquid recirculation tube while in the exhale phase, the one or more valves configured to control flow through the liquid, gas supply and/or suction passages when the apparatus switches between the inhale phase and an exhale phase are piloted valves, the piloted valves configured control flow through the liquid, gas supply and/or suction passages when the apparatus switches between the inhale phase and an exhale phase are connected to pilot tubes, the pilot tubes are connected to solenoid valves that are actuated by the control unit, the fluid reservoir is connected to a pump by pressure line and a vacuum line, a valve positioned in the pressure line and a valve positioned in the vacuum line, the valve positioned in the pressure line and a valve positioned in the vacuum line are formed in an integrally formed manifold, the integrally formed manifold is formed by 3D printing, in the inhale phase the valve in the pressure line is open and the valve in the vacuum line is closed and wherein in the exhale phase the valve in the pressure line is closed and the valve in the vacuum line is opened, in the inhale phase a valve in the gas delivery passage opens allowing gas to flow an adjustable amount of time prior to a delayed opening of a valve in the liquid delivery passage which in turn shuts off the valve in the gas delivery passage, the valve in the gas delivery line is closed by back pressure or by actively closing the valve positioned in the pressure line and the valve positioned in the vacuum line are piloted valves, and/or the piloted valves are controlled by a single multiport solenoid valve.

The apparatus, according to exemplary embodiments may also include a turbine pump positioned between the fluid reservoir and the liquid delivery passage. The turbine pump may be configured to aerate liquid flowing between the fluid reservoir and the liquid delivery passage. The turbine pump may be configured to emulsify a second liquid into the liquid flowing between the fluid reservoir and the liquid delivery passage. The second liquid may be used to cool or heat the first liquid.

Exemplary embodiments may include adjustable timing to switch the apparatus between an inhale phase in which the liquid from the fluid reservoir is delivered through the liquid delivery passage and then to the delivery device and/or gas can be delivered from the gas source to the gas delivery passage to the delivery device and to the exhale phase in which liquid and/or gas can be withdrawn from the delivery device into the suction passage.

Exemplary embodiments include a method for partial liquid ventilation of lungs, comprising detecting a pressure in the lungs; when the pressure reaches a first value, delivering gas into the lungs and subsequently delivering a liquid to the lungs during an inhale phase; and when the pressure reaches a second value, switching to an exhale phase and withdrawing liquid and/or gas from the lungs until the pressure reaches a third value.

The method may include any combination of other exemplary steps or conditions including, for example, the first value is a preset vacuum and the second value is a threshold pressure; heating and/or cooling the liquid and/or gas before the liquid and/or gas is delivered to the lungs; heating and/or cooling the liquid and/or gas before the liquid and/or gas is delivered to the lungs comprises recirculating cool and/or warm liquid during the exhale phase through a tube assembly; delivering liquid in the inhale phase comprises delivering liquid from a fluid reservoir; during the exhale phase recirculating liquid from the fluid reservoir through a tube assembly; during exhale phase returning the withdrawn liquid to the fluid reservoir; switching from the inhale phase to the exhale phase comprising synchronized opening and closing of valves configure to control the flow of gas and/or liquid; delaying the switching from the inhale phase to exhale phase; adjusting the delay in switching from the inhale phase to exhale phase; applying cardiopulmonary resuscitation during the delay between the inhale phase to exhale phase; adjusting a timing between switching to an exhale phase and/or delivering liquid to the lungs after the pressure reaches a first value; adjusting a timing between switching to an exhale phase and/or delivering liquid to the lungs after the airway pressure reaches a first value is used to control the ratio of gas and liquid delivered to the patient; adjusting a timing between switching to an exhale phase and/or delivering liquid to the lungs after the pressure reaches a first value is used to aid pumping blood within the patient; and/or withdrawing liquid and/or gas from the lungs until the pressure reaches a third value comprises applying a vacuum.

Exemplary embodiments also include a method for partial liquid ventilation of lungs, comprising in response to detecting a patient's breathing, delivering gas into the lungs and subsequently delivering a liquid to the lungs during an inhale phase; detecting airway pressure in the lungs; and when the pressure reaches a first value, switching to an exhale phase and withdrawing liquid and/or gas from the lungs until the pressure reaches a second value.

Exemplary embodiments also include a method for partial liquid ventilation of lungs, comprising in response to an application of force to the patient's chest and resulting in the pressure to a patient's lungs during a cardiopulmonary resuscitation, delivering gas into the lungs and subsequently delivering a liquid to the lungs during an inhale phase; detecting airway pressure in the lungs; and when the pressure reaches a first value, switching to an exhale phase and withdrawing liquid and/or gas from the lungs until the pressure reaches a second value.

The exemplary methods may include any combination of additional conditions or steps, including, without limitation, the cardiopulmonary resuscitation comprises manual or automated CPR.

An exemplary embodiment includes a method for liquid ventilation of lungs, comprising aerating a liquid with a turbine pump; and delivering the aerated liquid to the lungs.

An exemplary embodiment includes a method for liquid ventilation of lungs, comprising with a turbine pump mixing a first liquid with a second liquid to create an emulsification of the first and second liquid, wherein the second liquid could be or is at a different temperature than the first liquid; and delivering the emulsification to the lungs.

An exemplary embodiment includes an apparatus for providing liquid and/or gas to a lung, comprising: a delivery device configured to deliver liquid and/or gas to the lung; a liquid delivery passage, a gas delivery passage and a suction passage, the liquid delivery, the gas delivery and the suction passages in fluid communication with the delivery device, a fluid reservoir in fluid communication with the liquid delivery passage; a vacuum source in communication with the suction passage; a gas source in communication with the gas delivery passage; and a one or more valves configured to control flow through the liquid delivery, the gas delivery and/or the suction passages when the apparatus switches between an inhale phase and an exhale phase; wherein the apparatus can be switched between a ventilation mode, a partial liquid ventilation mode and/or a total liquid ventilation mode.

An exemplary embodiment includes an apparatus for providing liquid and/or gas to a lung, comprising: one or more magnetic switches configured to prevent arcing. The exemplary embodiment may include other features, such as, for example, the apparatus is mode configured for conventional gas ventilation, total liquid ventilation and/or partial liquid ventilation and optionally can be switched between modes "on the fly" while ventilating if needed. Conventional gas ventilation mode optionally can be used "stand alone", without the intent of liquid ventilating, to extract liquid from the patient's lungs.

An exemplary embodiment includes an apparatus for providing liquid and/or gas to a lung, comprising: a gas containment and/or filter for containing and/or filtering gas and/or liquid removed from the lung. The exemplary embodiment may include any combination of features including, for example, the gas containment and/or filter is connected to the apparatus by a quick disconnect.

An exemplary embodiment includes an apparatus for providing liquid and/or gas to a lung in combination with a band configured to limit stretching of a patient's lungs.

An exemplary embodiment includes a method for ventilating a lung of a patient, comprising applying a band configured to limit stretching of a patient's lungs; and supplying ventilation to the patient. The method may include any combination of additional steps or conditions, such as, for example, providing liquid ventilation to the patient's lung; applying the band to the patient's lungs comprising limiting extension of the patient anatomy.

It should be emphasized that many variations and modifications may be made to the herein-described embodiments, the elements of which are to be understood as being among other acceptable examples. All such modifications and variations are intended to be included herein within the scope of this disclosure and protected by the following claims. Moreover, any of the steps described herein can be performed simultaneously or in an order different from the steps as ordered herein. Moreover, as should be apparent, the features and attributes of the specific embodiments disclosed herein may be combined in different ways to form additional embodiments, all of which fall within the scope of the present disclosure. Specifically, embodiments described herein include systems and methods for delivering and extracting a fluid from the lungs. The fluid may include liquid, gas, and combinations thereof. Exemplary embodiments describe passages, reservoirs, tubes, canisters or other components as liquid or gas for reference purposes only. These components can be interchangeably used as would be understood by a person of skill in the art for any fluid delivery/retrieval. As such liquid passages, tubes, and reservoirs are not limited to liquid, but can also include any fluid including liquid, gas, and combinations thereof; and gas passages, tubes, and reservoirs are not limited to gas, but can also include any fluid including liquid, gas, and combinations thereof. The disclosure of specific liquid and gas combinations are exemplary only, and not intended to be limiting.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Moreover, the following terminology may have been used herein. The singular forms "a," "an," and "the" include plural referents unless the context clearly dictates otherwise. Thus, for example, reference to an item includes reference to one or more items. The term "ones" refers to one, two, or more, and generally applies to the selection of some or all of a quantity. The term "plurality" refers to two or more of an item. The term "about" or "approximately" means that quantities, dimensions, sizes, formulations, parameters, shapes and other characteristics need not be exact, but may be approximated and/or larger or smaller, as desired, reflecting acceptable tolerances, conversion factors, rounding off, measurement error and the like and other factors known to those of skill in the art. The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide. For example, the terms "approximately", "about", and "substantially" may refer to an amount that is within less than 10% of, within less than 5% of, within less than 1% of, within less than 0.1% of, and within less than 0.01% of the stated amount or characteristic. Numbers preceded by a term such as "about" or "approximately" also include the recited numbers. For example, "about 3.5 mm" includes "3.5 mm. For example, the disclosure expressly contemplates being able a value or range proceeded by a term such as "about" or "approximately" in this disclosure with or without such term.

Numerical data may be expressed or presented herein in a range format. It is to be understood that such a range format is used merely for convenience and brevity and thus should be interpreted flexibly to include not only the numerical values explicitly recited as the limits of the range, but also interpreted to include all of the individual numerical values or sub-ranges encompassed within that range as if each numerical value and sub-range is explicitly recited. As an illustration, a numerical range of "about 1 to 5" should be interpreted to include not only the explicitly recited values of about 1 to about 5, but should also be interpreted to also include individual values and sub-ranges within the indicated range. Thus, included in this numerical range are individual values such as 2, 3 and 4 and sub-ranges such as "about 1 to about 3," "about 2 to about 4" and "about 3 to about 5," "1 to 3," "2 to 4," "3 to 5," etc. As another illustration, a numerical range of "about 1 to about 5" would also include the embodiment of a range of "1 to 5." This same principle applies to ranges reciting only one numerical value (e.g., "greater than about 1") and should apply regardless of the breadth of the range or the characteristics being described. A plurality of items may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. Furthermore, where the terms "and" and "or" are used in conjunction with a list of items, they are to be interpreted broadly, in that any one or more of the listed items may be used alone or in combination with other listed items. The term "alternatively" refers to selection of one of two or more alternatives, and is not intended to limit the selection to only those listed alternatives or to only one of the listed alternatives at a time, unless the context clearly indicates otherwise.

What is claimed is:

1. A device for providing liquid to a lung, comprising:
a delivery device configured to deliver a fluid to the lung, the delivery device having a liquid delivery passage, a gas delivery passage and a suction passage, a fluid reservoir in fluid communication with the liquid delivery passage;
a vacuum source in communication with the suction passage;
a gas source in communication with the gas delivery passage;
a pressure sensor;
one or more valves configured to control flow through the liquid delivery, the gas delivery and the suction passages when the apparatus switches between an inhale phase and an exhale phase;

a control unit operatively connected to the pressure sensor and the one or more valves, the control unit configured to, in response to a signal from the pressure sensor, switch the apparatus between the inhale phase in which a fluid is delivered to the delivery device by either a liquid from the fluid reservoir through the liquid delivery passage to the delivery device or a gas from the gas source through the gas delivery passage to the delivery device and an exhale phase in which a delivered fluid is withdrawn from the delivery device into the suction passage;

a tube assembly comprising a liquid delivery tube, a gas delivery tube, a suction tube, and a heat exchanger extending along a length of the tube assembly; and a heat reservoir in fluid communication with the heat exchanger, wherein the heat exchanger comprises one or more corrugated tubes wound in a helical fashion about a central cooling liquid supply tube contained within the fluid delivery device.

2. The device of claim 1, the delivery device comprising a filling device having a disconnect valve activated by connecting to a mating part which compresses an internal spring and opens a fluid path.

3. The device of claim 2, wherein the filling device is reversible for use in either filling or draining breathable liquid.

4. The device of claim 1, further comprising a turbine and a sparging device near the turbine to admit gasses into a stream of breathable liquid from the delivery device.

5. The device of claim 1, wherein at least one of the one or more valves is a 3D printed valve that is constructed containing a compliant seal device that capture a diaphragm and wherein the diaphragm is constructed larger in diameter than a female receptacle of the 3D printed valve causing a bowing effect on the diaphragm thereby increasing a flow path during an open condition of the valve wherein an opening and closing of the valve is effected via pressure or vacuum applied to one side of the diaphragm.

6. The device of claim 5, wherein a spring is used to bias that valve so that only one of pressure or vacuum need be applied to determine a state of the valve.

7. The device of claim 1, further comprising a variable timing device so that a portion of the inhaled fluid which is gas may be controlled.

8. The device of claim 1, further comprises a feedback loop in communication with a pulse oximeter or photoplethysmic device for modulating gasses introduced into a patient from the delivery device.

9. The device of claim 1, wherein one of the one or more valves comprises a diaphragm which fits into a cylinder such that the cylinder is smaller in diameter than the diaphragm resulting in the diaphragm taking a convex or concave shape.

10. The device of claim 1, further comprising an integral heater placed in a fluid line of the device.

11. The device of claim 1, further comprising one or more reservoir canisters having a transparent window and volumetric markings to permit a user to observe an ingress or egress of breathable liquid from the one or more reservoir canisters.

12. The device of claim 1, wherein the delivery device provides a single primary exit point for gasses from the device wherein the gasses are contained.

13. The device of claim 12, wherein the delivery device provides a single primary entrance point for gasses to the delivery device are controlled, treated, or mixed.

14. The device of claim 1, further comprising a manifold comprising a transparent 3D printed component with a surface applied of biocompatible epoxy.

15. The device of claim 1, wherein the one or more valves comprises a control valve of a transparent 3D printed component with a surface applied of biocompatible urethane.

16. An apparatus comprising:

a delivery device configured to deliver a fluid to a lung;

a liquid delivery passage, a gas delivery passage, and a suction passage, the liquid delivery, the gas delivery, and the suction passages in fluid communication with the delivery device;

a fluid reservoir in fluid communication with the liquid delivery passage;

a vacuum source in communication with the suction passage;

a gas source in communication with the gas delivery passage;

a pressure sensor;

one or more valves configured to control flow through the liquid delivery, the gas delivery, and the suction passages when the apparatus switches between an inhale phase and an exhale phase;

a control unit operatively connected to the pressure sensor and the one or more valves, the control unit configured to switch the apparatus between the inhale phase wherein the fluid is delivered to the delivery device by either a liquid from the fluid reservoir through the liquid delivery passage to the delivery device or a gas from the gas source to the gas delivery passage to the delivery device and an exhale phase wherein a delivered fluid is withdrawn from the delivery device into the suction passage in response to a signal from the pressure sensor; and a heat exchanger in the suction passage, wherein the heat exchanger modulates a temperature of thermal liquid by one or more of slowing or interrupting a flow of the thermal liquid, and diverting a flow of the thermal liquid.

17. The apparatus of claim 16, further comprising a liquid cooler having one or more coiled corrugated tubes through which cooling fluid flows.

18. The apparatus of claim 16, further comprising a secondary cooler or warmer for the withdrawn delivered fluid in the suction passage, the secondary cooler or warmer comprising another liquid to cool or warm the withdrawn delivered fluid extracted from a subject.

19. The apparatus of claim 18, further comprising a primary cooler having a distal end connected to the delivery device, wherein the primary cooler is configured to introduce cooling liquid proximally and co-axially with the delivery device via a flexible tube which extends distally toward a subject and from which coolant then flows proximally in the opposing direction of a flow of breathable liquid within an outer fluid jacket of the delivery device.

20. The apparatus of claim 19, wherein a temperature sensor is positioned in a liquid path near to a subject when the apparatus is in use, the temperature sensor used to modulate liquid being delivered from the apparatus.

21. The apparatus of claim 20, further comprising a pressure sensing switch coupled to a pump or turbine, the pressure sensing switch terminates or reduces power to the pump or turbine that supplies breathable liquid, during the exhale phase.

22. The apparatus of claim 21, further comprising an ice bath having water and ice with a chemical to depress a solid to liquid phase change of ice.

* * * * *